United States Patent
Fukushima et al.

(10) Patent No.: US 9,331,284 B2
(45) Date of Patent: May 3, 2016

(54) POLYMER COMPOUND AND LIGHT-EMITTING DEVICE USING SAME

(75) Inventors: Daisuke Fukushima, Ushiku (JP); Brian Tierney, Cambridgeshire (GB); Natasha Conway, Cambridgeshire (GB); Mary McKiernan, Reading (GB)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 635 days.

(21) Appl. No.: 13/575,348

(22) PCT Filed: Jan. 28, 2011

(86) PCT No.: PCT/JP2011/051707
§ 371 (c)(1),
(2), (4) Date: Sep. 4, 2012

(87) PCT Pub. No.: WO2011/093428
PCT Pub. Date: Aug. 4, 2011

(65) Prior Publication Data
US 2012/0326140 A1 Dec. 27, 2012

(30) Foreign Application Priority Data
Jan. 28, 2010 (JP) .................. 2010-016533

(51) Int. Cl.
*C08G 73/02* (2006.01)
*H01L 51/00* (2006.01)
(Continued)

(52) U.S. Cl.
CPC ............ *H01L 51/0043* (2013.01); *C07C 25/22* (2013.01); *C08G 61/02* (2013.01);
(Continued)

(58) Field of Classification Search
CPC ............. B32B 2457/206; C07C 25/22; C07C 2103/18; C08G 61/02; C08G 61/12; C08G 2261/1412; C08G 2261/411; C08G 2261/148; C08G 2261/3142; C08G 2261/3162; C08G 2261/95; C08G 2261/76; C09K 11/06; C09K 2211/1483; C09K 2211/1458; C09K 2211/1416; C09K 2211/1425; C09K 2211/1433; C09K 2211/1466; H01L 51/0043; H01L 51/0085; H01L 51/5016; Y10T 428/1055
USPC ................. 257/40, E51.026; 528/8; 252/500, 252/301.35; 524/610; 558/290
See application file for complete search history.

(56) References Cited

U.S. PATENT DOCUMENTS
5,777,070 A 7/1998 Inbasekaran et al.
5,821,002 A 10/1998 Ohnishi et al.
(Continued)

FOREIGN PATENT DOCUMENTS
CN 1726243A A 1/2006
EP 2110399 A1 10/2009
(Continued)

OTHER PUBLICATIONS
Extended European Search Report issued Apr. 23, 2013 in European Patent Application No. 11737138.5 to Sumitomo Chemical Co., Ltd., et al.
(Continued)

*Primary Examiner* — Gwendolyn Blackwell
*Assistant Examiner* — Eli D Strah
(74) *Attorney, Agent, or Firm* — Sughrue Mion, PLLC

(57) ABSTRACT

It is an object of the invention to provide a polymer compound that, when used in a light-emitting device, results in excellent luminance life for the obtained light-emitting device. The invention provides a polymer compound comprising a constitutional unit represented by formula (1).

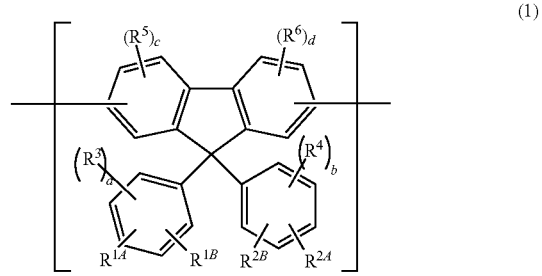

[In formula (1), $R^{1A}$, $R^{1B}$, $R^{2A}$, $R^{2B}$ represent an unsubstituted alkyl group, $R^3$ and $R^4$ represented an unsubstituted or substituted alkyl group, an unsubstituted or substituted alkoxy group, an unsubstituted or substituted aryl group, an unsubstituted or substituted aryloxy group, an unsubstituted or substituted heterocyclic group, an unsubstituted or substituted silyl group, a halogen atom, an alkoxycarbonyl group, a carboxyl or a cyano group, and $R^5$ and $R^6$ represent an unsubstituted or substituted alkyl group, an unsubstituted or substituted alkoxy group or an unsubstituted or substituted aryl group. The letters a, b, c and d each represent an integer of 0 to 3. When multiple $R^3$, $R^4$, $R^5$ and $R^6$ groups are present, they may be the same or different.]

7 Claims, 3 Drawing Sheets

(51) Int. Cl.

| | | |
|---|---|---|
| *C08G 61/12* | (2006.01) | |
| *C09K 11/06* | (2006.01) | |
| *C07C 25/22* | (2006.01) | |
| *C08G 61/02* | (2006.01) | |
| *H01L 51/50* | (2006.01) | |

(52) U.S. Cl.
CPC ............... *C08G 61/12* (2013.01); *C09K 11/06* (2013.01); *B32B 2457/206* (2013.01); *C07C 2103/18* (2013.01); *C08G 2261/148* (2013.01); *C08G 2261/1412* (2013.01); *C08G 2261/3142* (2013.01); *C08G 2261/3162* (2013.01); *C08G 2261/411* (2013.01); *C08G 2261/76* (2013.01); *C08G 2261/95* (2013.01); *C09K 2211/1416* (2013.01); *C09K 2211/1425* (2013.01); *C09K 2211/1433* (2013.01); *C09K 2211/1458* (2013.01); *C09K 2211/1466* (2013.01); *C09K 2211/1483* (2013.01); *H01L 51/0085* (2013.01); *H01L 51/5016* (2013.01); *Y10T 428/1055* (2015.01)

(56) References Cited

U.S. PATENT DOCUMENTS

| | | | |
|---|---|---|---|
| 6,653,438 | B1 | 11/2003 | Spreitzer et al. |
| 8,878,163 | B2 * | 11/2014 | Conway et al. .................. 257/40 |
| 2002/0106531 | A1 | 8/2002 | Naito |
| 2003/0143429 | A1 | 7/2003 | Suzuki et al. |
| 2004/0170839 | A1 | 9/2004 | O'Dell et al. |
| 2004/0170863 | A1 | 9/2004 | Kim et al. |
| 2006/0228576 | A1 | 10/2006 | Burroughes et al. |
| 2007/0252139 | A1 | 11/2007 | Mckiernan et al. |
| 2008/0265755 | A1 | 10/2008 | Yu et al. |
| 2009/0203876 | A1 * | 8/2009 | Grand et al. ................... 528/422 |
| 2009/0315453 | A1 * | 12/2009 | Kobayashi et al. ........... 313/504 |
| 2010/0033086 | A1 * | 2/2010 | Mikami et al. ................ 313/504 |

FOREIGN PATENT DOCUMENTS

| | | | |
|---|---|---|---|
| GB | 2340304 | A | 2/2000 |
| GB | 2454890 | A | 5/2009 |
| JP | 9-45478 | A | 2/1997 |
| JP | 2001-520289 | A | 10/2001 |
| JP | 2002-527553 | A | 8/2002 |
| JP | 2002-280183 | A | 9/2002 |
| JP | 2004-2654 | A | 1/2004 |
| JP | 2004-532325 | A | 10/2004 |
| JP | 2006-505647 | A | 2/2006 |
| JP | 2007-321023 | A | 12/2007 |
| JP | 2008-106125 | A | 5/2008 |
| WO | 99/13692 | A1 | 3/1999 |
| WO | 99/48160 | A1 | 9/1999 |
| WO | 02/092724 | A1 | 11/2002 |
| WO | 03/095586 | A1 | 11/2003 |
| WO | 2004/041902 | A3 | 5/2004 |
| WO | 2006/109083 | A1 | 10/2006 |
| WO | 2007/109518 | A3 | 9/2007 |
| WO | WO 2008111658 | A1 * | 9/2008 ............. C08G 61/12 |
| WO | 2010/065178 | A1 | 6/2010 |

OTHER PUBLICATIONS

Second Office Action issued Aug. 8, 2014 in counterpart Chinese Patent Application No. 201180007200.4 with English translation.
Norio Miyaura and Akira Suzuki, "Palladium-Catalyzed Cross-Coupling Reactions of Organoboron Compounds", Chem. Rev., vol. 95, No. 7, 1995, pp. 2457-2483.
"Library of Polymer Functional Materials vol. 2 Synthesis and Reaction of Polymer (2)", Kyoritsu Shuppan Co., Ltd., pp. 432-433 with partial English translation.
Takakazu Yamamoto, "Electrically Conducting and Thermally Stable $\pi$-Conjugated Poly(arylene)s Prepared by Organometallic Processes", Prog. Polym. Sci., vol. 17, 1992, pp. 1153-1205.
Andrew C. Grimsdale, et al., "Correlation Between Molecular Structure, Microscopic Morphology, and Optical Properties of Poly(tetraalkylindenofluorene)s", Adv. Funct. Mater., vol. 12, No. 10, Scheme 1, 2002, pp. 729-733.
Sepas Setayesh, et al., "Polyfluorenes with Polyphenylene Dendron Side Chains: Toward Non-Aggregating, Light-Emitting Polymers", J. Am. Chem. Soc., vol. 123, Scheme 5, 2001, pp. 946-953.
Translation of the International Preliminary Report on Patentability mailed Sep. 27, 2012 in International Application No. PCT/JP2011/051707 to Sumitomo Chemical Co., Ltd.
Examination Report issued Dec. 1, 2014 in counterpart Taiwanese Patent Application No. 100103278 with translation.
Search Report issued May 25, 2011 in GB Patent Application No. 1101559.1.
Notice of Reasons for Rejection issued Apr. 30, 2014 in counterpart Japanese Patent Application No. P2011-016932 with translation.
Notice of Reasons for Rejection issued Apr. 30, 2014 in counterpart Japanese Patent Application No. P2011-016911 with translation.
First Office Action issued Nov. 26, 2013 in counterpart Chinese Patent Application No. 201180007200.4 with English translation.
Office Action issued Aug. 16, 2012 in U.S. Appl. No. 13/016,847 to Fukushuima.
Ken-Tsung Wong, et al, "Ter(9,9-diarylfluorene)s: Highly Efficient Blue Emitter with Promising Electrochemical and Thermal Stability", J. Am. Chem. Soc., 2002, vol. 124, pp. 11576-11577.
Communication dated Oct. 21, 2015 from the Intellectual Property Office of the United Kingdom in counterpart application No. 1101559.1.

* cited by examiner

POLYMER COMPOUND AND LIGHT-EMITTING DEVICE USING SAME

CROSS REFERENCE TO RELATED APPLICATIONS

This application is a National Stage of International Application No. PCT/JP2011/051707 filed Jan. 28, 2011, claiming priority based on Japanese Patent Application No. 2010-016533 filed Jan. 28, 2010, the contents of all of which are incorporated herein by reference in their entirety.

TECHNICAL FIELD

The present invention relates to a polymer compound, and more specifically to a fluorene-based polymer compound and a light-emitting device using it.

BACKGROUND ART

Light-emitting devices such as organic electroluminescence elements have been an object of interest in recent years as their properties including low-voltage driving and high luminance render them suitable for use in displays and the like. Light-emitting materials and charge transport materials are used in the production of light-emitting devices.

Polymer compounds that allow formation of organic layers by dissolution in solvents and coating are being studied as light-emitting materials and charge transport materials, and as such polymer compounds there have been proposed polymer compounds that comprise constitutional units derived from fluorene having alkyl group substituents (PTL 1).

CITATION LIST

Patent Literature

[PTL 1] Japanese Patent Public Inspection No. 2001-520289

SUMMARY OF INVENTION

Technical Problem

However, when the polymer compounds mentioned above have been used to fabricate light-emitting devices, the luminance life of the light-emitting devices has been less than adequate.

It is therefore an object of the present invention to provide a polymer compound that, when used in a light-emitting device, results in excellent luminance life for the obtained light-emitting device.

Solution to Problem

In order to achieve the aforestated object, the invention provides, firstly, a polymer compound comprising a constitutional unit represented by formula (1).

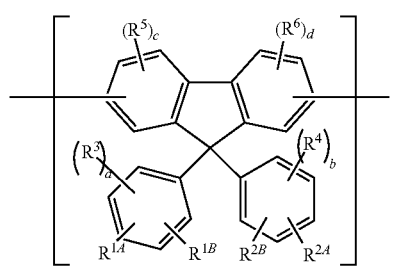

(1)

[in formula (1), $R^{1A}$, $R^{1B}$, $R^{2A}$ and $R^{2B}$ each independently represent an unsubstituted alkyl group; $R^3$ and $R^4$ each independently represent an unsubstituted or substituted alkyl group, an unsubstituted or substituted alkoxy group, an unsubstituted or substituted aryl group, an unsubstituted or substituted aryloxy group, an unsubstituted or substituted monovalent heterocyclic group, an unsubstituted or substituted silyl group, a halogen atom, an alkoxycarbonyl group, a carboxyl group or a cyano group; $R^5$ and $R^6$ each independently represent an unsubstituted or substituted alkyl group, an unsubstituted or substituted alkoxy group or an unsubstituted or substituted aryl group; the letters a, b, c and d each independently represent an integer of 0 to 3; when multiple $R^3$, $R^4$, $R^5$ and $R^6$ groups are present, they may be the same or different.]

In formula (1), $R^{1A}$ is preferably a primary or secondary unsubstituted alkyl group. Also, $R^{2A}$ is preferably a primary or secondary unsubstituted alkyl group.

In formula (1), at least one of a combination of $R^{1A}$ and $R^{1B}$ and a combination of $R^{2A}$ and $R^{2B}$ is a combination of mutually differing groups.

The constitutional unit represented by formula (1) is preferably a constitutional unit represented by formula (2).

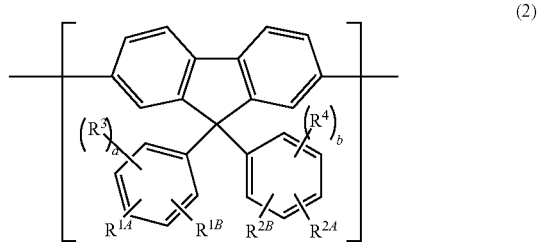

(2)

[In formula (2), $R^{1A}$, $R^{1B}$, $R^{2A}$, $R^{2B}$, $R^3$, $R^4$, a and b have the same meanings specified above.]

More preferably in formulas (1) and (2), a and b each independently represent 0 or 1, and $R^3$ and $R^4$ each independently represent an unsubstituted alkyl group.

The constitutional unit represented by formula (2) is preferably a constitutional unit represented by formula (3).

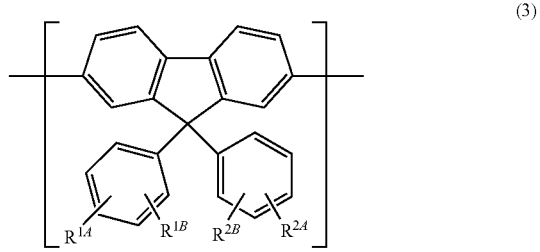

(3)

[In formula (3), $R^{1A}$, $R^{1B}$, $R^{2A}$ and $R^{2B}$ have the same meanings specified above.]

The constitutional unit represented by formula (3) is more preferably a constitutional unit represented by formula (4) above.

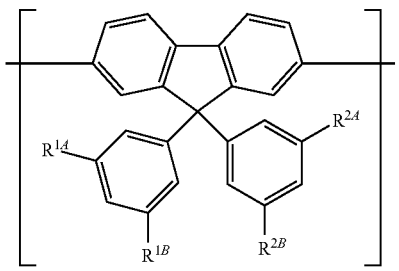

(4)

[In formula (4), $R^{1A}$, $R^{1B}$, $R^{2A}$ and $R^{2B}$ have the same meanings specified above.]

The polymer compound of the invention preferably further comprises one or more constitutional units selected from the group consisting of constitutional units represented by formula (6) and constitutional units represented by formula (7).

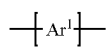

(6)

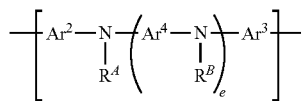

(7)

[in formula (6), $Ar^1$ represents an unsubstituted or substituted arylene group or an unsubstituted or substituted divalent heterocyclic group; this is with the proviso that the constitutional unit represented by formula (6) is a constitutional unit having a different structure from the constitutional unit represented by formula (1);

in formula (7), $Ar^2$, $Ar^3$ and $Ar^4$ each independently represent an unsubstituted or substituted arylene group, an unsubstituted or substituted divalent aromatic heterocyclic group or an unsubstituted or substituted divalent group in which two aromatic rings are linked by a single bond; $R^A$ and $R^B$ each independently represent a hydrogen atom, an unsubstituted or substituted alkyl group, an unsubstituted or substituted aryl group or an unsubstituted or substituted monovalent heterocyclic group; the letter e represents 0 or 1.]

In this case, the constitutional unit represented by formula (6) is preferably a constitutional unit represented by formula (8), a constitutional unit represented by formula (9), a constitutional unit represented by formula (10) or a constitutional unit represented by formula (11).

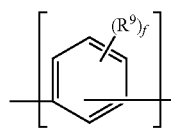

(8)

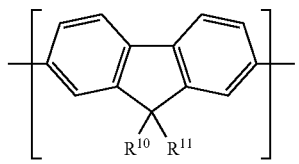

(9)

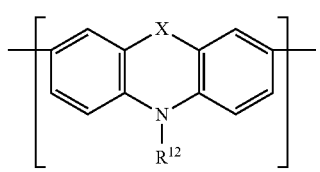

(10)

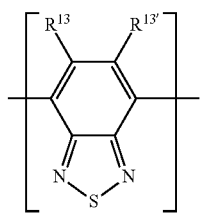

(11)

[in formula (8), $R^9$ represents an unsubstituted or substituted alkyl group, an unsubstituted or substituted alkoxy group, an unsubstituted or substituted aryl group, an unsubstituted or substituted aryloxy group, an unsubstituted or substituted monovalent heterocyclic group, an unsubstituted or substituted silyl group, a halogen atom, an alkoxycarbonyl group, a carboxyl group or a cyano group; the letter f represents an integer of 0 to 4; when multiple $R^9$ groups are present, they may be the same or different;

in formula (9), $R^{10}$ and $R^{11}$ each independently represent a hydrogen atom, an unsubstituted or substituted alkyl group or an unsubstituted or substituted aryl group; this is with the proviso that the constitutional unit represented by formula (9) is a constitutional unit having a different structure from the constitutional unit represented by formula (1); in formula (10), $R^{12}$ represents an unsubstituted or substituted alkyl group, an unsubstituted or substituted aryl group or an unsubstituted or substituted monovalent heterocyclic group; X represents a single bond, —O—, —S— or —C($R^c$)$_2$—; $R^c$ represents an unsubstituted or substituted alkyl group or an unsubstituted or substituted aryl group; the two $R^c$ groups may be the same or different;

in formula (11), $R^{13}$ and $R^{13'}$ each independently represent a hydrogen atom, an unsubstituted or substituted alkyl group, an unsubstituted or substituted alkoxy group, an unsubstituted or substituted aryl group, an unsubstituted or substituted aryloxy group, an unsubstituted or substituted monovalent heterocyclic group, an unsubstituted or substituted silyl group, a halogen atom, an alkoxycarbonyl group, a carboxyl group or a cyano group.]

Such a polymer compound preferably includes one or more constitutional units selected from the group consisting of constitutional units represented by formula (12) and constitutional units represented by formula (13).

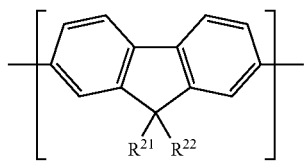

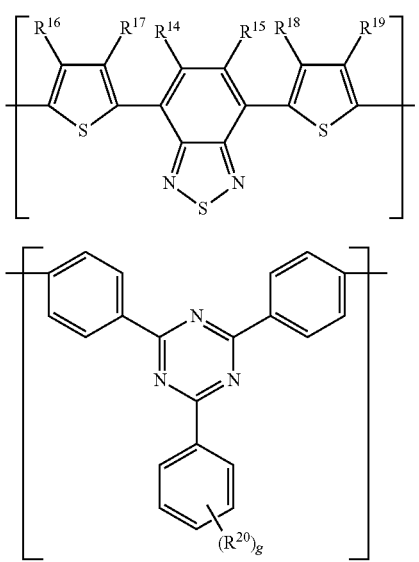

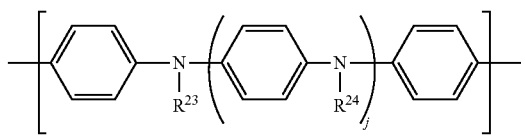

[in formula (12), $R^{14}$, $R^{15}$, $R^{16}$, $R^{17}$, $R^{18}$ and $R^{19}$ each independently represent a hydrogen atom, an unsubstituted or substituted alkyl group, an unsubstituted or substituted alkoxy group, an unsubstituted or substituted aryl group, an unsubstituted or substituted aryloxy group, an unsubstituted or substituted monovalent heterocyclic group, an unsubstituted or substituted silyl group, a halogen atom, an alkoxycarbonyl group, a carboxyl group or a cyano group; in formula (13), $R^{20}$ represents an unsubstituted or substituted alkyl group, an unsubstituted or substituted alkoxy group, an unsubstituted or substituted aryl group, an unsubstituted or substituted aryloxy group, an unsubstituted or substituted monovalent heterocyclic group, an unsubstituted or substituted silyl group, a halogen atom, an alkoxycarbonyl group, a carboxyl group or a cyano group; the letter g represents an integer of 0 to 5, when multiple $R^{20}$ groups are present, they may be the same or different.]

The constitutional unit represented by formula (7) is preferably a constitutional unit represented by formula (14).

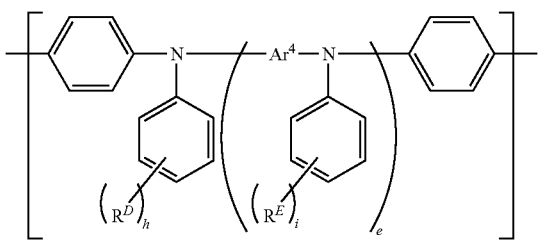

[in formula (14), $Ar^4$ and e have the same meanings specified above; $R^D$ and $R^E$ each independently represent an unsubstituted or substituted alkyl group, an unsubstituted or substituted alkoxy group, an unsubstituted or substituted aryl group, an unsubstituted or substituted aryloxy group, an unsubstituted or substituted monovalent heterocyclic group, an unsubstituted or substituted silyl group, a halogen atom, an alkoxycarbonyl group, a carboxyl group or a cyano group; the letters h and i each independently represent an integer of 0 to 5; when multiple groups are present for $R^D$ and $R^E$, they may be the same or different.]

The polymer compound of the invention preferably further comprises one or more constitutional units selected from the group consisting of constitutional units represented by formula (15) and constitutional units represented by formula (16).

[in formula (15), $R^{21}$ represents a crosslinkable group; $R^{22}$ represents a hydrogen atom, a crosslinkable group, an unsubstituted or substituted alkyl group or an unsubstituted or substituted aryl group; this is with the proviso that the constitutional unit represented by formula (15) is a constitutional unit having a different structure from the constitutional unit represented by formula (1), the constitutional unit represented by formula (6) and the constitutional unit represented by formula (9);

in formula (16), $R^{23}$ represents a crosslinkable group; $R^{24}$ represents a crosslinkable group, an unsubstituted or substituted alkyl group or an unsubstituted or substituted aryl group; the letter j represents 0 or 1; this is with the proviso that the constitutional unit represented by formula (16) is a constitutional unit having a different structure from the constitutional unit represented by formula (7) and the constitutional unit represented by formula (14).]

A particularly preferred example of the polymer compound of the invention is one comprising a constitutional unit represented by formula (1), and at least one constitutional unit selected from the group consisting of a constitutional unit represented by formula (6) and a constitutional units represented by formula (7).

The invention provides, secondly, a composition comprising at least one material selected from the group consisting of hole transport materials, electron transport materials and light-emitting materials, and the aforementioned polymer compound of the invention.

The invention provides, thirdly, a composition comprising the aforementioned polymer compound of the invention and a solvent.

The invention provides, fourthly, a film comprising the aforementioned polymer compound of the invention.

The invention provides, fifthly, a light-emitting device comprising electrodes consisting of an anode and a cathode, and a layer comprising the aforementioned polymer compound of the invention formed between the electrodes.

The invention provides, sixthly, a compound represented by formula (a).

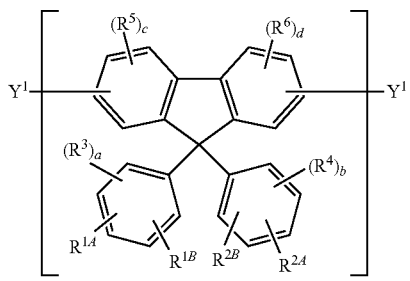

(a)

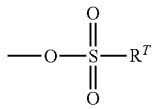

(a-1)

(a-2)

(a-3)

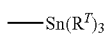

(a-4)

[in formula (a), $R^{1A}$, $R^{1B}$, $R^{2A}$ and $R^{2B}$ each independently represent an unsubstituted alkyl group; $R^3$ and $R^4$ each independently represent an unsubstituted or substituted alkyl group, an unsubstituted or substituted alkoxy group, an unsubstituted or substituted aryl group, an unsubstituted or substituted aryloxy group, an unsubstituted or substituted monovalent heterocyclic group, an unsubstituted or substituted silyl group, a halogen atom, an alkoxycarbonyl group, a carboxyl group or a cyano group; $R^5$ and $R^6$ each independently represent an unsubstituted or substituted alkyl group, an unsubstituted or substituted alkoxy group or an unsubstituted or substituted aryl group; the letters a, b, c and d each independently represent an integer of 0 to 3; when multiple $R^3$, $R^4$, $R^5$ and $R^6$ groups are present, they may be the same or different; $Y^1$ is a halogen atom, a methoxy group, a boric acid ester residue, a boric acid residue, a group represented by formula (a-1), a group represented by formula (a-2), a group represented by formula (a-3) or a group represented by formula (a-4); Two $Y^1$ groups may be the same or different;

in formulas (a-1) and (a-4), $R^T$ represents an unsubstituted or substituted alkyl group or an unsubstituted or substituted aryl group; multiple $R^T$ groups in formula (a-4) may be the same or different;

in formulas (a-2) and (a-3), $X_A$ represents a halogen atom.]

Advantageous Effects of Invention

The polymer compound of the invention having the specific structure described above, when used for fabrication of a light-emitting device, results in excellent luminance life for the obtained light-emitting device. The polymer compound of the invention is therefore useful as an electronic component material, such as a light-emitting material or charge transport material. Thus, the polymer compound and light-emitting device of the invention are useful for liquid crystal display backlights, curved or flat light sources for illumination, segment type display devices, dot matrix flat panel displays, and the like.

DESCRIPTION OF EMBODIMENTS

Figure 1:
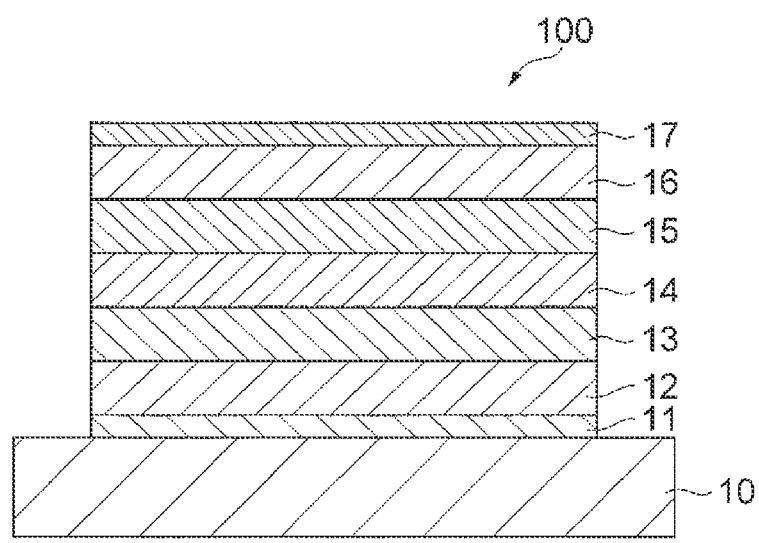
FIG. 1 is a schematic cross-sectional view showing an embodiment of a light-emitting device of the invention.

Preferred embodiments of the invention will now be explained.

The terms used throughout the present specification will be explained first. Throughout the present specification, the term "constitutional unit" refers to a unit of which at least one is present in the polymer compound. The term "n-valent heterocyclic group" (where n is 1 or 2) means a group derived by removing n hydrogen atoms from a heterocyclic compound (especially an aromatic heterocyclic compound). The term "heterocyclic compound" refers to an organic compound with a ring structure, wherein the elements composing the ring are not only carbon atoms but also include a heteroatom such as an oxygen atom, sulfur atom, nitrogen atom, phosphorus atom or boron atom. The term "arylene group" refers to an atomic group derived by removing 2 hydrogens from an aromatic hydrocarbon. The term "aryl group" refers to an atomic group derived by removing one hydrogen from an aromatic hydrocarbon, and it includes groups with fused rings, and directly bonded independent benzene rings or two or more fused rings.

[Polymer Compound]

A polymer compound according to a preferred embodiment will now be explained.

(Constitutional Unit Represented by Formula (1))

The polymer compound of the invention comprises a constitutional unit represented by formula (1) above.

In formula (1), $R^{1A}$, $R^{1B}$, $R^{2A}$ and $R^{2B}$ each independently represent an unsubstituted alkyl group. The unsubstituted alkyl groups represented by $R^{1A}$, $R^{1B}$, $R^{2A}$ and $R^{2B}$ may be straight-chain, branched or cyclic. The number of carbon atoms of each unsubstituted alkyl group will usually be 1-20, preferably 1-15, more preferably 1-10, even more preferably 1-8 and particularly preferably 1-6.

In formula (1), $R^{1A}$ and $R^{2A}$ are each preferably a primary or secondary unsubstituted alkyl group.

In formula (1), $R^{1A}$ and $R^{2A}$ are preferably each independently a primary or secondary unsubstituted alkyl group such as methyl group, ethyl group, n-propyl group, isopropyl group, n-butyl group, isobutyl group, n-pentyl group, isoamyl group, n-hexyl group, cyclohexyl group, n-heptyl group, n-octyl group, 2-ethylhexyl group, n-nonyl group, n-decyl group, 3,7-dimethyloctyl group or n-dodecyl group. More preferred among these are primary unsubstituted alkyl groups such as methyl group, ethyl group, n-propyl group, n-butyl group, n-pentyl group, n-hexyl group, n-heptyl group, n-octyl group, 2-ethylhexyl group, n-nonyl group, n-decyl group, 3,7-dimethyloctyl group and n-dodecyl group, and more preferably are primary straight-chain unsubstituted alkyl groups such as methyl group, ethyl group, n-propyl group, n-butyl group, n-pentyl group, n-hexyl group, n-heptyl group and n-octyl group.

In formula (1), $R^{1B}$ and $R^{2B}$ are preferably each independently a primary or tertiary unsubstituted alkyl group such as methyl group, ethyl group, n-propyl group, n-butyl group, t-butyl group, n-pentyl group, 1,1-dimethylpropyl group, n-hexyl group, n-heptyl group, n-octyl group, 2-ethylhexyl group, n-nonyl group, n-decyl group, 3,7-dimethyloctyl group, n-dodecyl group or 1-adamantyl group. More preferred among these are primary unsubstituted alkyl groups such as methyl group, ethyl group, n-propyl group, n-butyl group, n-pentyl group, n-hexyl group, n-heptyl group, n-octyl group, 2-ethylhexyl group, n-nonyl group, n-decyl group, 3,7-dimethyloctyl group and n-dodecyl group, and more preferably are primary straight-chain unsubstituted alkyl groups such as methyl group, ethyl group, n-propyl group, n-butyl group, n-pentyl group, n-hexyl group, n-heptyl group and n-octyl group.

From the viewpoint of solubility of the polymer compound in organic solvents, either or both the combination of $R^{1A}$ and $R^{1B}$ and/or the combination of $R^{2A}$ and $R^{2B}$ is a combination of mutually differing groups. More preferably, $R^{1A}$ and $R^{1B}$ are different groups, and $R^{2A}$ and $R^{2B}$ are different groups.

From the viewpoint of ease of synthesis of the monomer to obtain a polymer compound, either or both the combination of $R^{1A}$ and $R^{1B}$ and/or the combination of $R^{2A}$ and $R^{2B}$ is a combination of identical groups. More preferably, $R^{1A}$ and $R^{1B}$ are identical groups and $R^{2A}$ and $R^{2B}$ are identical groups.

In formula (1), $R^3$ and $R^4$ each independently represent unsubstituted or substituted alkyl group, unsubstituted or substituted alkoxy group, unsubstituted or substituted aryl group, unsubstituted or substituted aryloxy group, an unsubstituted or substituted monovalent heterocyclic group, unsubstituted or substituted silyl group, a halogen atom, alkoxycarbonyl group, carboxyl group or cyano group. Preferred among these are unsubstituted or substituted alkyl group, unsubstituted or substituted alkoxy group, unsubstituted or substituted aryl group and alkoxycarbonyl groups, more preferred are unsubstituted or substituted alkyl group and unsubstituted or substituted alkoxy groups, even more preferred are unsubstituted or substituted alkyl groups, and most preferred are unsubstituted alkyl groups.

The unsubstituted alkyl groups represented by $R^3$ and $R^4$ may be straight-chain, branched or cyclic. The number of carbon atoms will usually be 1-20, preferably 1-15, more preferably 1-10, even more preferably 1-8 and particularly preferably 1-6.

The unsubstituted alkyl groups represented by $R^3$ and $R^4$ may be methyl group, ethyl group, n-propyl group, isopropyl group, n-butyl group, isobutyl group, tert-butyl group, n-pentyl group, isoamyl group, n-hexyl group, cyclohexyl group, n-heptyl group, n-octyl group, 2-ethylhexyl group, n-nonyl group, n-decyl group, 3,7-dimethyloctyl group, lauryl group or the like. Preferred among these are methyl group, ethyl group, n-propyl group, isopropyl group, n-butyl group, isobutyl group, tert-butyl group, n-pentyl group, isoamyl group, n-hexyl group, n-octyl group, 2-ethylhexyl group and 3,7-dimethyloctyl groups, more preferred are methyl group, n-butyl group, tert-butyl group, n-hexyl group and n-octyl groups and even more preferred are methyl group, n-butyl group and n-hexyl groups, for a satisfactory balance between solubility of the polymer compound in organic solvents and the life of the obtained light-emitting device.

The substituted alkyl groups represented by $R^3$ and $R^4$ may be straight-chain, branched or cyclic. The number of carbon atoms is usually 1-20, preferably 1-15 and more preferably 1-10, not including the number of carbon atoms of substituents.

The substituted alkyl groups represented by $R^3$ and $R^4$ may include alkyl groups substituted with halogen atoms, such as trifluoromethyl group, pentafluoroethyl group, perfluorobutyl group, perfluorohexyl group and perfluorooctyl group, alkyl groups substituted with aryl groups, such as phenylmethyl group and 4-(4-hexylphenyl)butyl group, and alkyl groups substituted with alkoxy groups such as ethyloxymethyl group and ethyloxyethyl group.

The unsubstituted or substituted alkoxy groups represented by $R^3$ and $R^4$ may be straight-chain, branched or cyclic. The number of carbon atoms is usually 1-20, preferably 1-15 and more preferably 4-10, not including the number of carbon atoms of substituents.

Unsubstituted or substituted alkoxy groups represented by $R^3$ and $R^4$ include methoxy group, ethoxy group, n-propyloxy group, isopropyloxy group, n-butyloxy group, isobutyloxy group, tert-butyloxy group, n-pentyloxy group, n-hexyloxy group, cyclohexyloxy group, n-heptyloxy group, n-octyloxy group, 2-ethylhexyloxy group, n-nonyloxy group, n-decyloxy group, 3,7-dimethyloctyloxy group, lauryloxy group, trifluoromethoxy group, pentafluoroethoxy group, perfluorobutoxy group, perfluorohexyloxy group, perfluorooctyloxy group, methoxymethyloxy group, 2-methoxyethyloxy group and 2-ethoxyethyloxy group. To satisfactorily improve the balance between solubility of the polymer compound in organic solvents and heat resistance, n-butyloxy group, n-pentyloxy group, n-hexyloxy group, n-octyloxy group, 2-ethylhexyloxy group, n-decyloxy group, 3,7-dimethyloctyloxy group and 2-ethoxyethyloxy groups are preferred.

The number of carbon atoms of an unsubstituted or substituted aryl group represented by $R^3$ and $R^4$ will usually be 6-60, preferably 6-48, more preferably 6-20 and even more preferably 6-10, not including the number of carbon atoms of substituents.

Unsubstituted or substituted aryl groups represented by $R^3$ and $R^4$ include phenyl group, 1-naphthyl group, 2-naphthyl group, 1-anthracenyl group, 2-anthracenyl group, 9-anthracenyl group, 1-pyrenyl group, 2-pyrenyl group, 4-pyrenyl group, 2-perylenyl group, 3-perylenyl group, 2-fluorenyl group, 3-fluorenyl group, 4-fluorenyl group, 1-biphenylenyl group, 2-biphenylenyl group, 2-phenanthrenyl group, 9-phenanthrenyl group, 2-phenylphenyl group, 3-phenylphenyl group, 4-phenylphenyl group, and these groups having a hydrogen atom replaced with alkyl group, alkoxy group, alkyloxycarbonyl group, acyl group, N,N-dialkylamino group, N,N-diarylamino group, cyano group, nitro group, chlorine atom, fluorine atom or the like. In order to satisfactorily improve the balance between solubility of the polymer compound in organic solvents and heat resistance, phenyl groups substituted with phenyl group and alkyl group are preferred.

Alkyl-substituted phenyl groups include 2-methylphenyl group, 3-methylphenyl group, 4-methylphenyl group, 3-n-butylphenyl group, 4-n-butylphenyl group, 4-tert-butylphenyl group, 3-n-hexylphenyl group, 4-n-hexylphenyl group, 4-n-octylphenyl group, 3,5-dimethylphenyl group, 3-n-hexyl-5-methylphenyl group and 3,5-dihexylphenyl group.

The number of carbon atoms of an unsubstituted or substituted aryloxy group represented by $R^3$ and $R^4$ will usually be 6-60 and preferably 7-48, not including the number of carbon atoms of substituents.

Unsubstituted or substituted aryloxy groups represented by $R^3$ and $R^4$ include phenoxy group, 1-naphthyloxy group, 2-naphthyloxy group, 1-anthracenyloxy group, 9-anthracenyloxy group, 1-pyrenyloxy group, and these groups having a hydrogen atom replaced with alkyl group, alkoxy group, alkyloxycarbonyl group, acyl group, N,N-dialkylamino group, N,N-diarylamino group, cyano group, nitro group, chlorine atom, fluorine atom or the like.

The number of carbon atoms of an unsubstituted or substituted monovalent heterocyclic group represented by $R^3$ and $R^4$ will usually be 4-60 and preferably 4-20, not including the number of carbon atoms of substituents.

Unsubstituted or substituted monovalent heterocyclic groups represented by $R^3$ and $R^4$ include thienyl group, pyrrolyl group, furyl group, pyridyl group, piperidyl group, quinolyl group, isoquinolyl group, pyrimidyl group, triazinyl group, and these groups having a hydrogen atom replaced with alkyl group, alkoxy group or the like. Preferred among these are thienyl group, pyridyl group, quinolyl group, isoquinolyl group, pyrimidyl group, triazinyl group, and these groups having a hydrogen atom replaced with alkyl group or alkoxy group, and more preferred are pyridyl group, pyrimidyl group, triazinyl group, and these groups having a hydrogen atom replaced with alkyl group or alkoxy group.

Substituted silyl groups represented by $R^3$ and $R^4$ include silyl groups substituted with 1-3 groups selected from the group consisting of unsubstituted alkyl group, unsubstituted or substituted aryl group and unsubstituted or substituted monovalent heterocyclic groups. The definitions and examples of unsubstituted alkyl group, unsubstituted or substituted aryl group and unsubstituted or substituted monovalent heterocyclic groups are the same as above. The number of carbon atoms of an substituted silyl group will usually be 1-60 and is preferably 3-48.

Substituted silyl groups represented by $R^3$ and $R^4$ include trimethylsilyl group, triethylsilyl group, tri-n-propylsilyl group, tri-isopropylsilyl group, dimethyl-isopropylsilyl group, tert-butyldimethylsilyl group, triphenylsilyl group, tri-p-xylylsilyl group, tribenzylsilyl group, diphenylmethylsilyl group, tert-butyldiphenylsilyl group and dimethylphenylsilyl group.

Halogen atoms represented by $R^3$ and $R^4$ include fluorine atom, chlorine atom, bromine atom and iodine atom, with fluorine atom being preferred.

The number of carbon atoms of an alkoxycarbonyl group represented by $R^3$ and $R^4$ will usually be 2-60 and is preferably 2-10. Alkoxycarbonyl groups include methoxycarbonyl group, ethoxycarbonyl group, n-propyloxycarbonyl group, isopropyloxycarbonyl group, n-butyloxycarbonyl group and tert-butyloxycarbonyl group.

$R^5$ and $R^6$ in formula (1) each independently represent unsubstituted or substituted alkyl group, unsubstituted or substituted alkoxy group or unsubstituted or substituted aryl group.

The definitions and examples of unsubstituted or substituted alkyl group, unsubstituted or substituted alkoxy group or unsubstituted or substituted aryl groups represented by $R^5$ and $R^6$ are the same as the definitions and examples of unsubstituted or substituted alkyl group, unsubstituted or substituted alkoxy group or unsubstituted or substituted aryl groups represented by $R^3$ and $R^4$, respectively.

In formula (1), a and b each independently represent an integer of 0 to 3, preferably an integer of 0 to 2, more preferably 0 or 1 and particularly preferably 0.

In formula (1), c and d each independently represent an integer of 0 to 3, preferably 0 or 1 and more preferably 0.

The constitutional unit represented by formula (1) is preferably a constitutional unit represented by formula (2), more preferably a constitutional unit represented by formula (3), even more preferably a constitutional unit represented by formula (4), formula (4A) or formula (4B), especially preferably a constitutional unit represented by formula (4) or a constitutional unit represented by formula (4B), and particularly preferably a constitutional unit represented by formula (4).

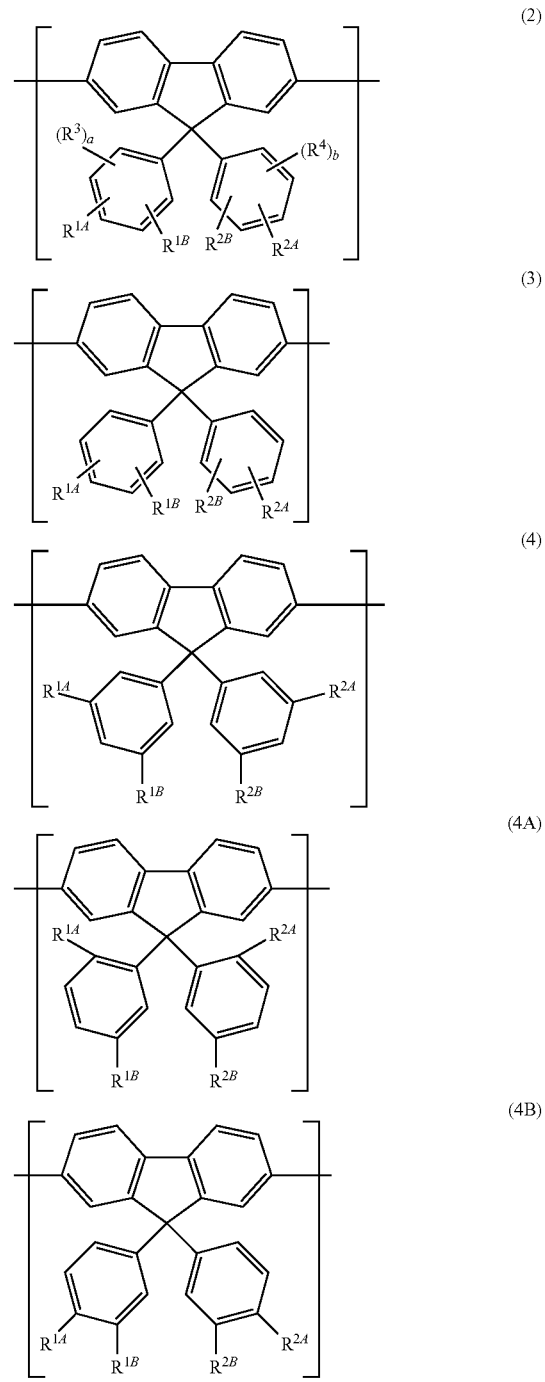

[In formulas (2), (3), (4), (4A) and (4B), $R^{1A}$, $R^{1B}$, $R^{2A}$, $R^{2B}$, $R^3$, $R^4$, a and b have the same meanings specified above.]

Constitutional units represented by formula (1) include constitutional units represented by the following formulas (1A-1) to (1A-4), (1B-1) to (1B-4), (1C-1) to (1C-6), (1D-1) to (1D-4), (1E-1) to (1E-8), (1F-1) to (1F-12), (1G-1) to (1G-7), (1H-1) to (1H-10), (1J-1) to (1J-6), (1K-1) to (1K-4), (1L-1) to (1L-3), (1M-1) to (1M-2), (1N-1) to (1N-23), (1P-1) to (1P-33) and (1Q-1) to (1Q-6).

Of these, in order to further lengthen the luminance life of the obtained light-emitting device, there are preferred constitutional units represented by the following formulas (1A-1) to (1A-4), (1B-1) to (1B-4), (1C-1) to (1C-6), (1D-1) to (1D-4), (1E-1) to (1E-8), (1F-1) to (1F-12), (1G-1) to (1G-7), (1H-1) to (1H-10), (1J-1) to (1J-6), (1K-1) to (1K-4), (1L-1) to (1L-3), (1M-1) to (1M-2) and (1N-1) to (1N-23), there are more preferred constitutional units represented by the following formulas (1A-1) to (1A-4), (1B-1) to (1B-4), (1C-1) to (1C-6), (1D-1) to (1D-4), (1E-1) to (1E-8), (1F-1) to (1F-12), (1G-1) to (1G-7), (1H-1) to (1H-10), (1J-1) to (1J-6), (1K-1) to (1K-4), (1L-1) to (1L-3) and (1N-4)-(1N-17), there are even more preferred constitutional units represented by the following formulas (1A-1) to (1A-4), (1B-1) to (1B-4), (1C-1) to (1C-6), (1D-1) to (1D-4), (1E-1) to (1E-8), (1F-1) to (1F-12), (1G-1) to (1G-7), (1H-1) to (1H-10), (1J-1) to (1J-6), (1K-1) to (1K-4) and (1L-1) to (1L-3), there are especially preferred constitutional units represented by the following formulas (1A-1) to (1A-4), (1B-1) to (1B-4), (1C-1) to (1C-6), (1D-1) to (1D-4), (1E-1) to (1E-8) and (1F-1) to (1F-12), there are particularly preferred constitutional units represented by the following formulas (1C-1) to (1C-6), (1D-1) to (1D-4), (1E-1) to (1E-8) and (1F-1) to (1F-12), and there are most preferred constitutional units represented by the following formulas (1F-1) to (1F-12).

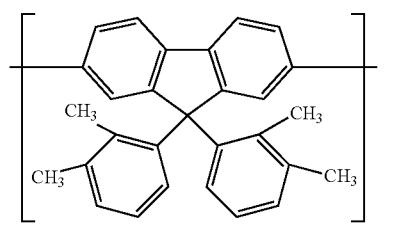

(1A-1)

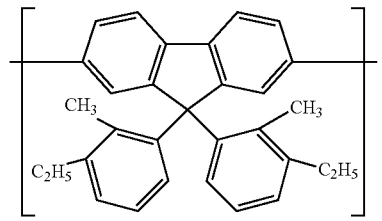

(1A-2)

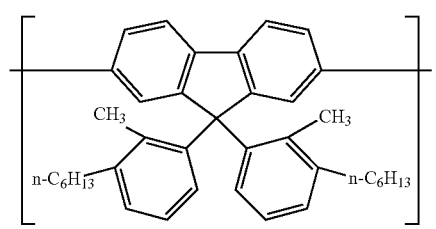

(1A-3)

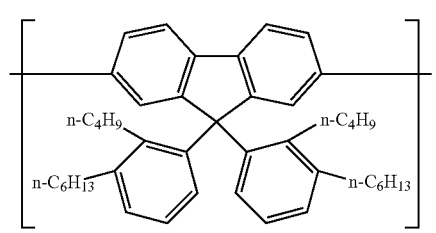

(1A-4)

-continued

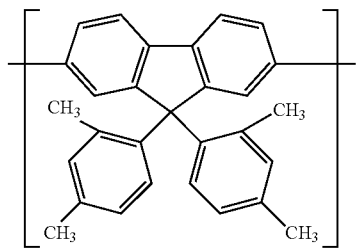

(1B-1)

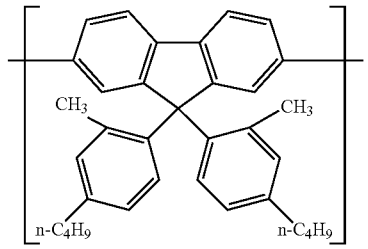

(1B-2)

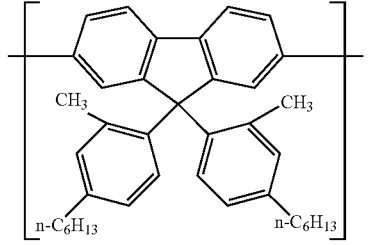

(1B-3)

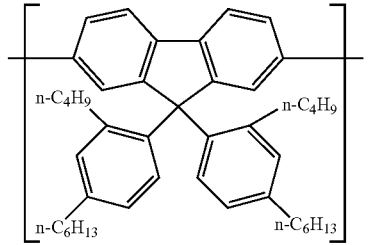

(1B-4)

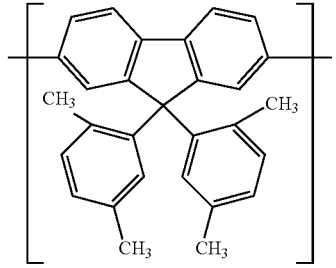

(1C-1)

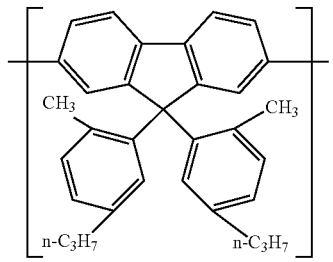

(1C-2)

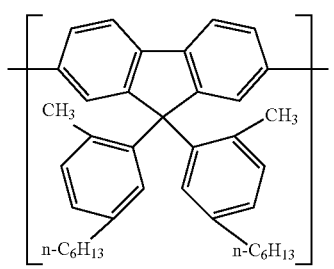 (1C-3)
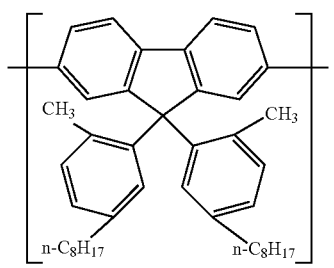 (1C-4)
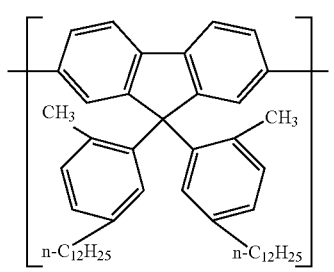 (1C-5)
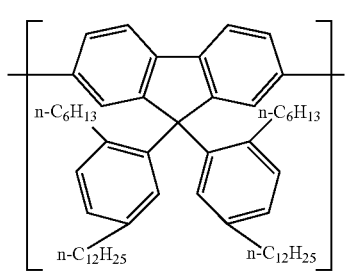 (1C-6)
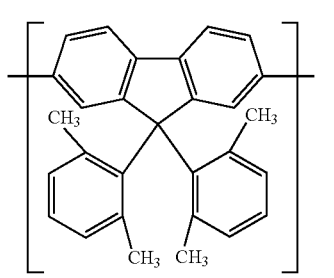 (1D-1)
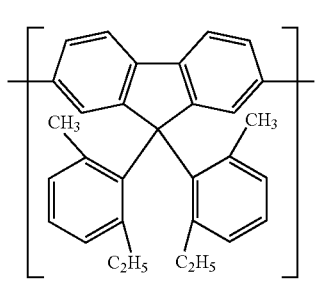 (1D-2)
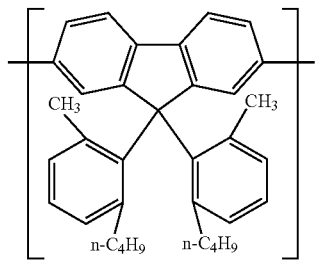 (1D-3)
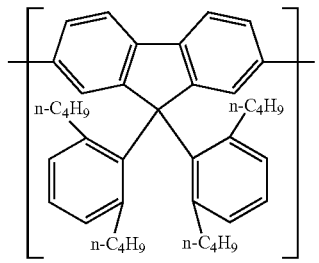 (1D-4)
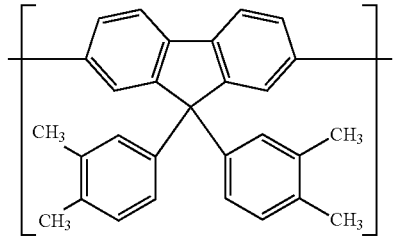 (1E-1)
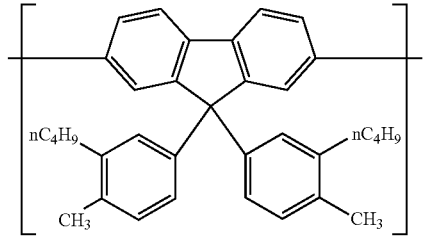 (1E-2)
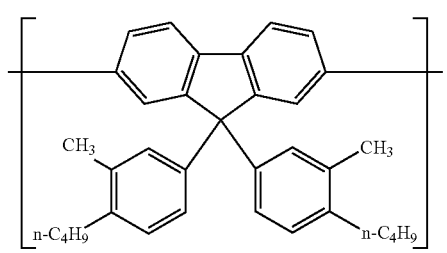 (1E-3)
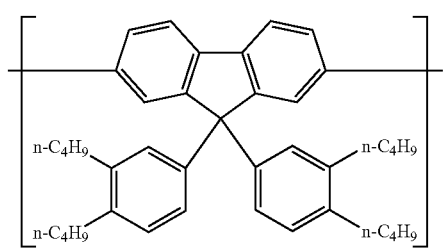 (1E-4)

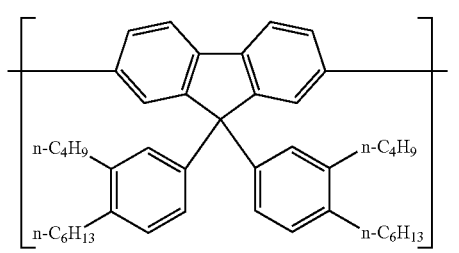 (1E-5)
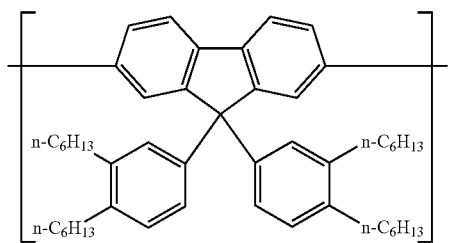 (1E-6)
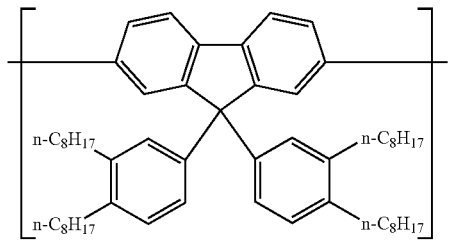 (1E-7)
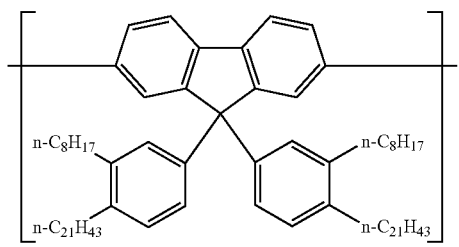 (1E-8)
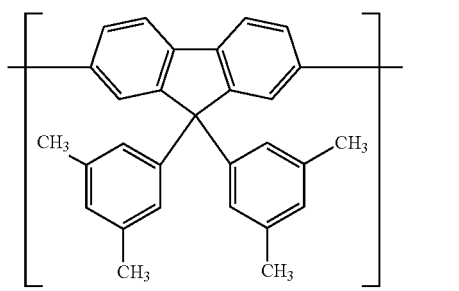 (1F-1)
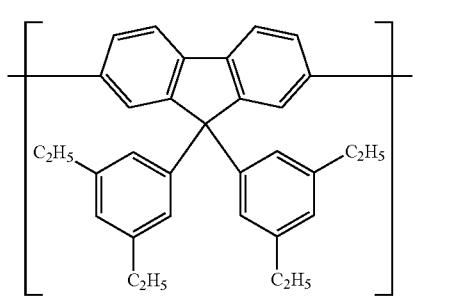 (1F-2)
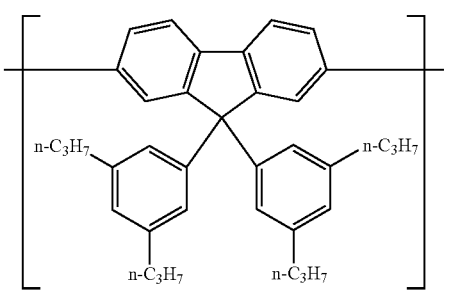 (1F-3)
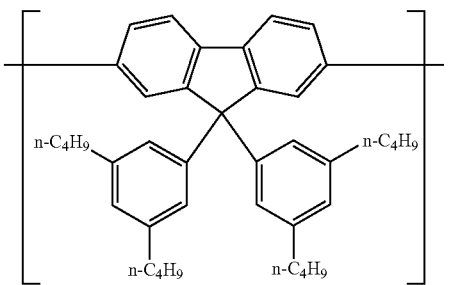 (1F-4)
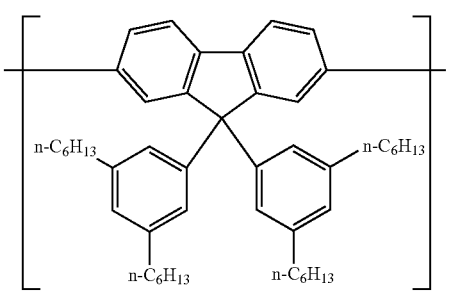 (1F-5)
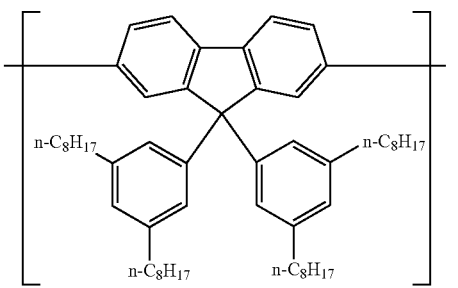 (1F-6)
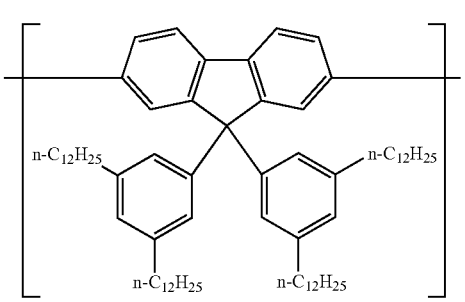 (1F-7)

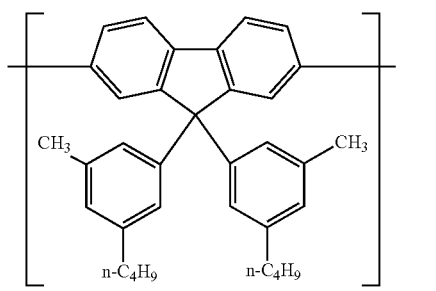
(1F-8)
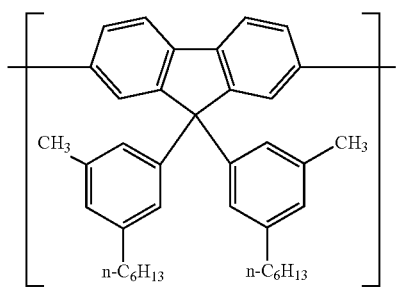
(1F-9)
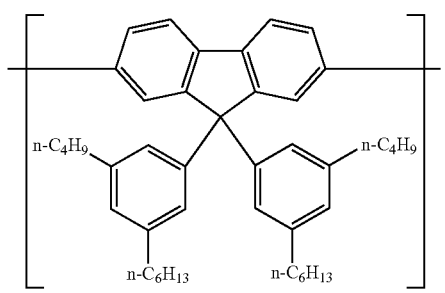
(1F-10)
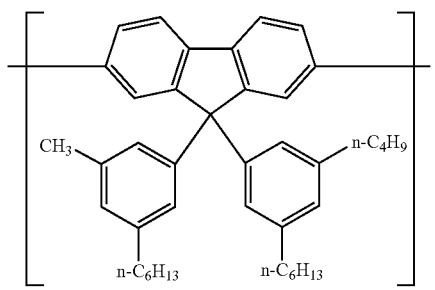
(1F-11)
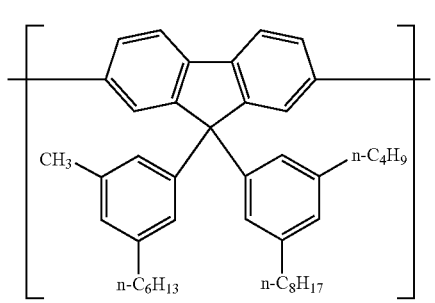
(1F-12)
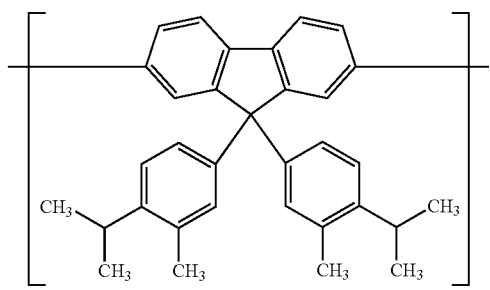
(1G-1)
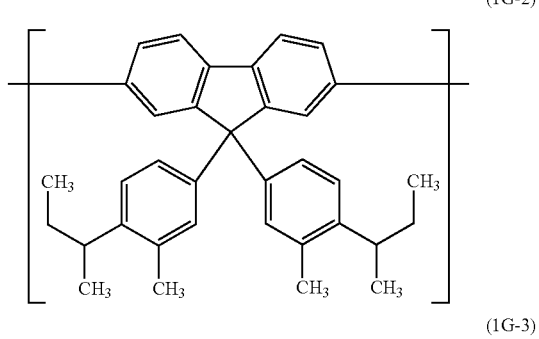
(1G-2)
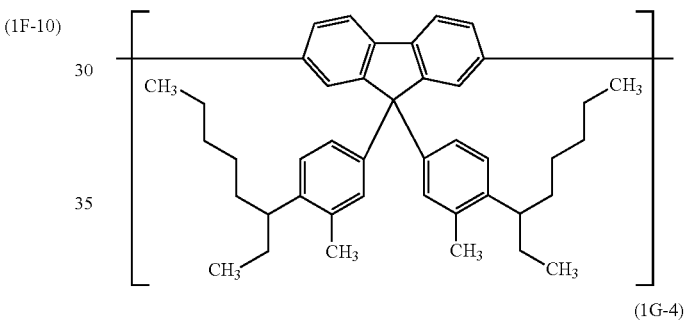
(1G-3)
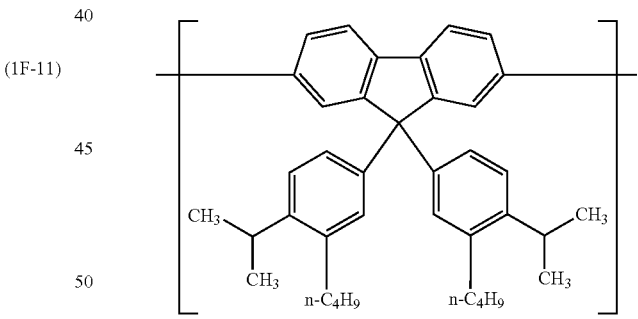
(1G-4)
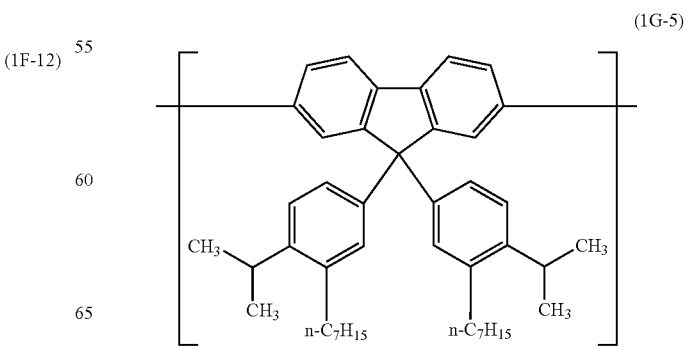
(1G-5)

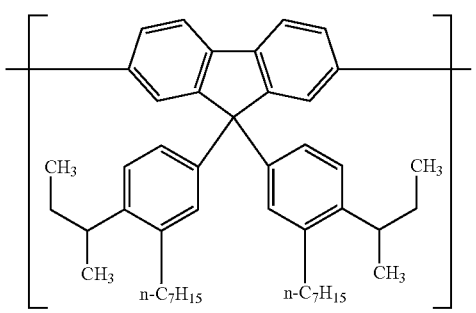
(1G-6)
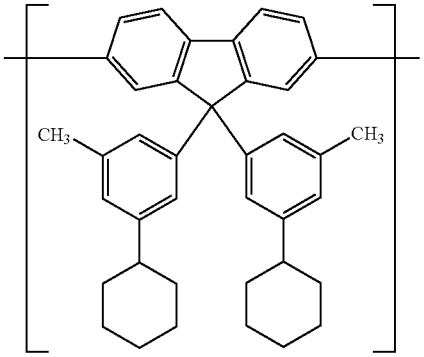
(1H-3)
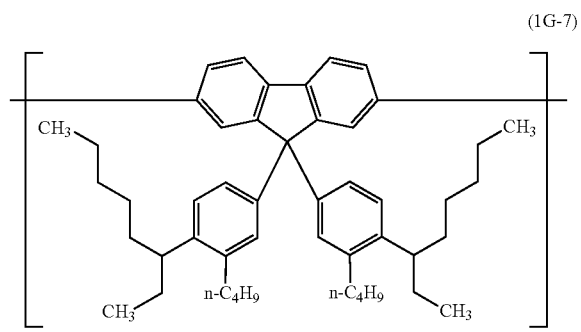
(1G-7)
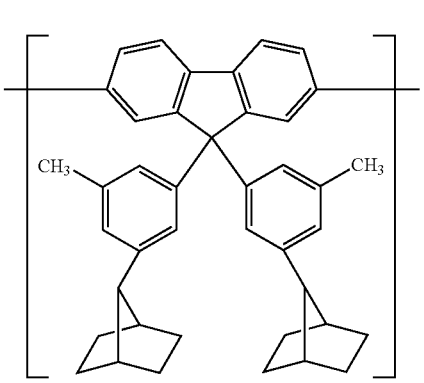
(1H-4)
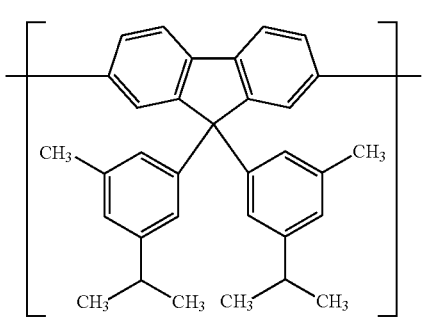
(1H-1)
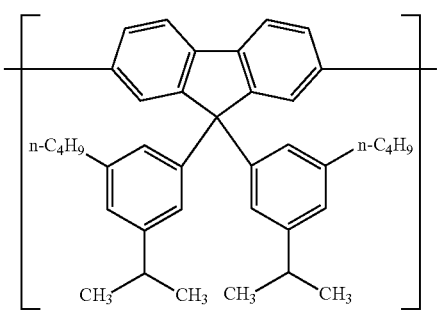
(1H-5)
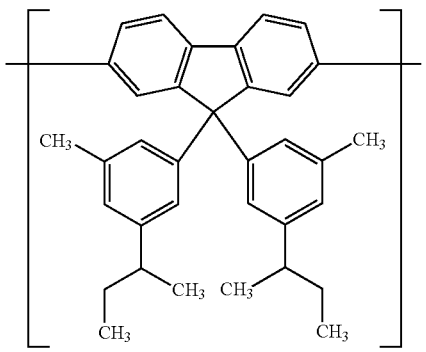
(1H-2)
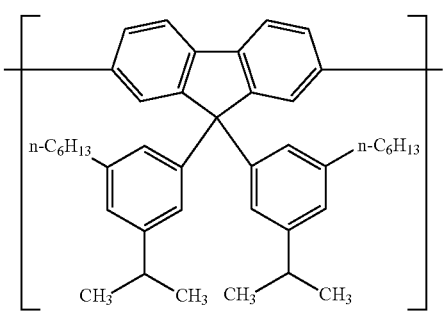
(1H-6)

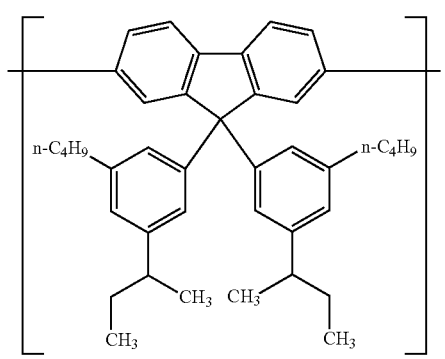
(1H-7)
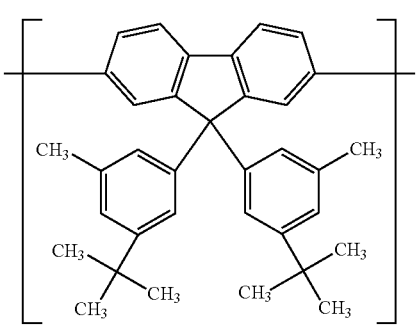
(1J-1)
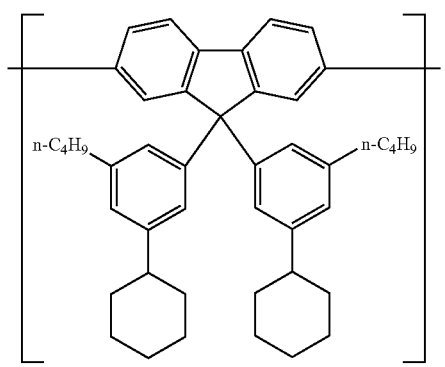
(1H-8)
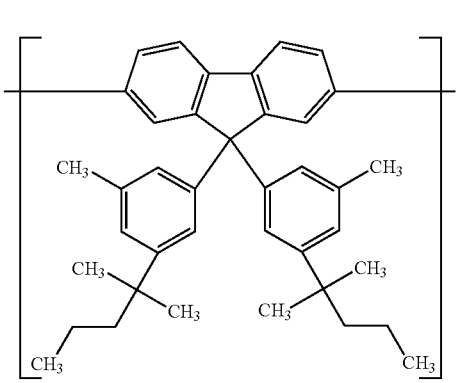
(1J-2)
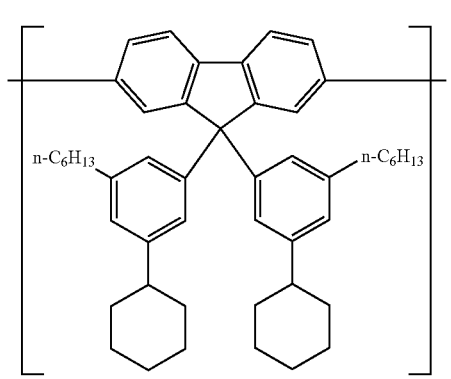
(1H-9)
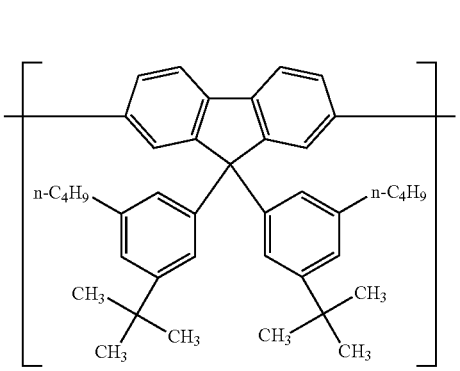
(1J-3)
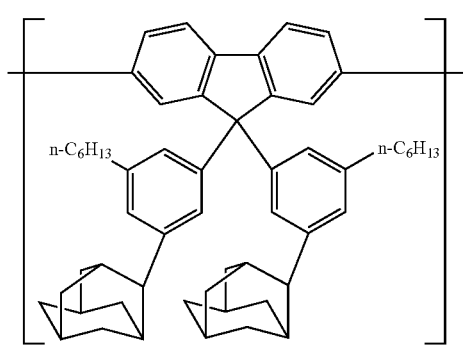
(1H-10)
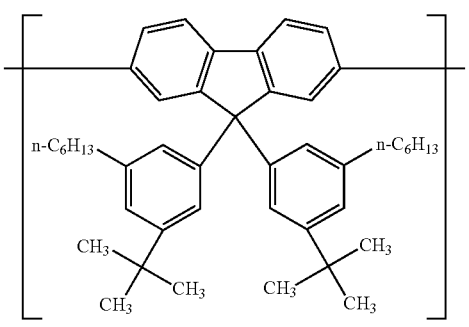
(1J-4)

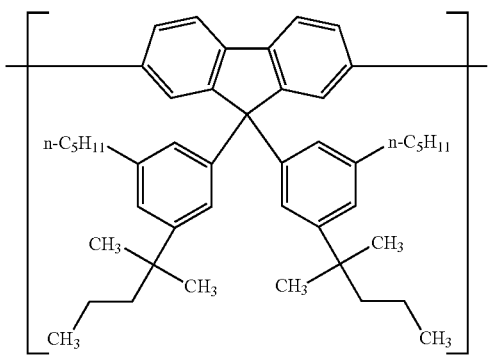
(1J-5)
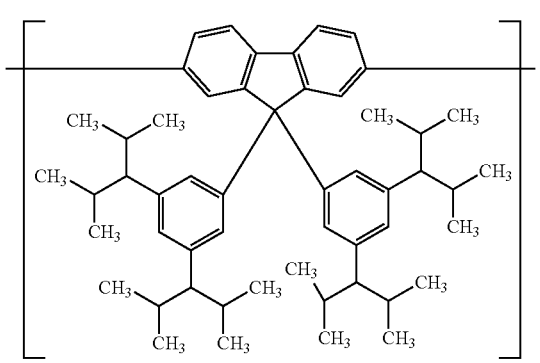
(1K-3)
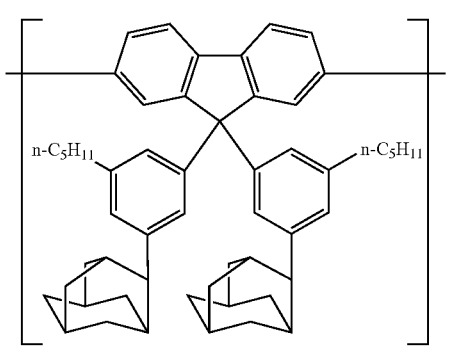
(1J-6)
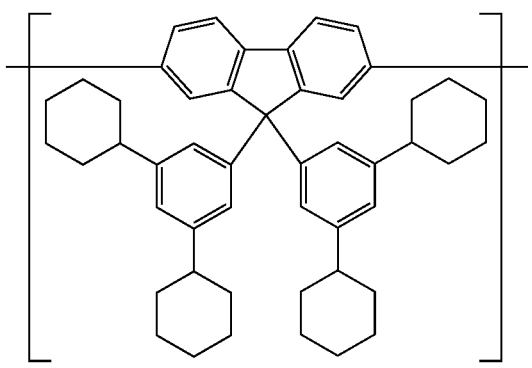
(1K-4)
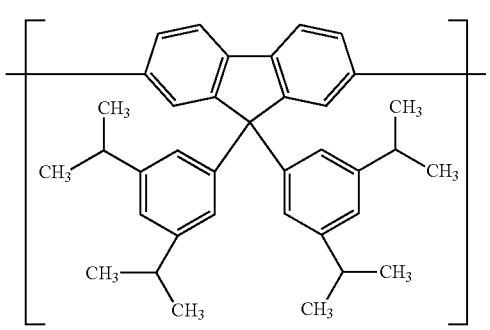
(1K-1)
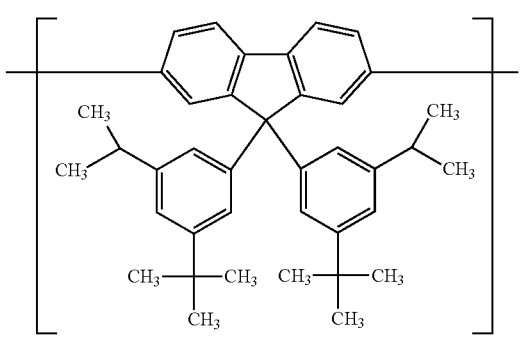
(1L-1)
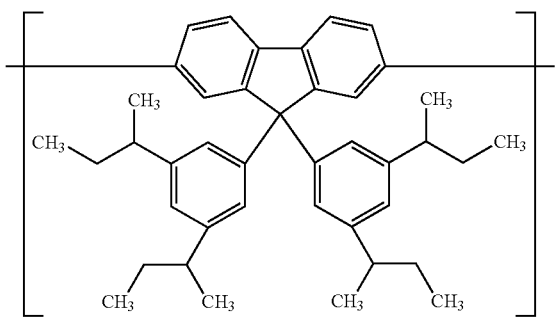
(1K-2)
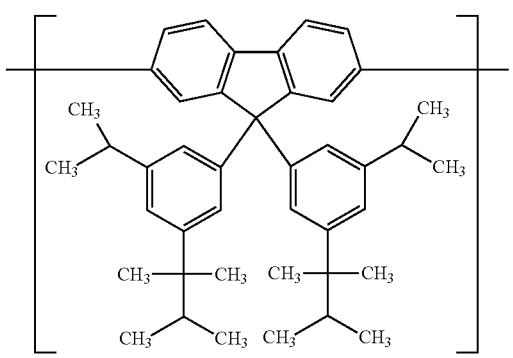
(1L-2)

(1L-3)
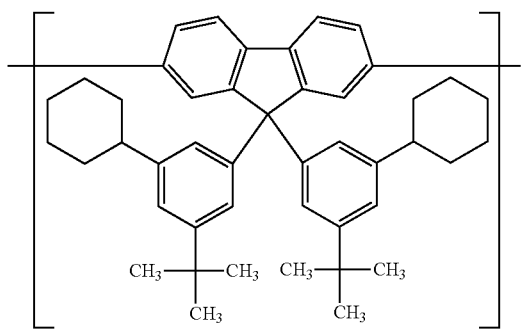
(1M-1)
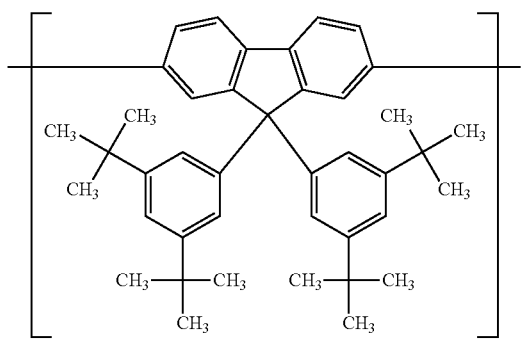
(1M-2)
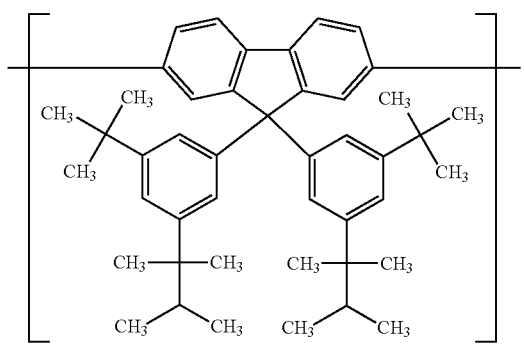
(1N-1)
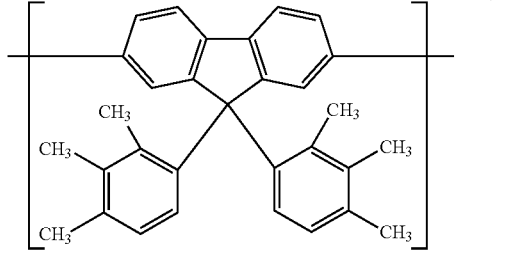
(1N-2)
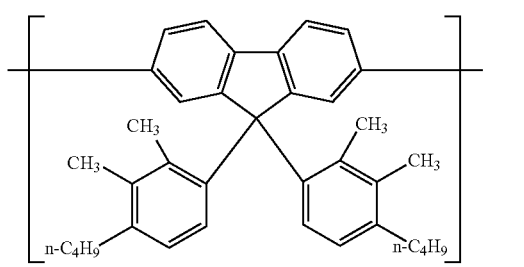
(1N-3)
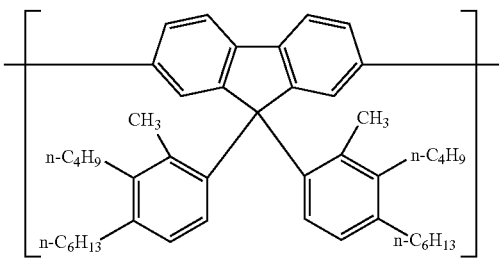
(1N-4)
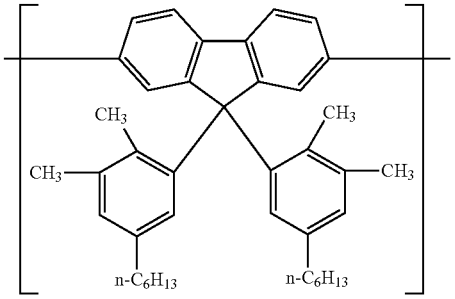
(1N-5)
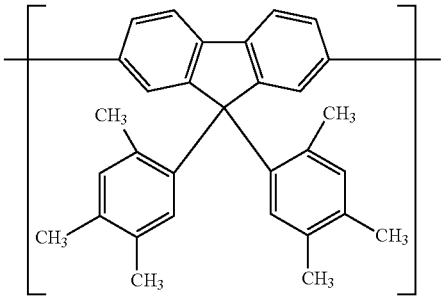
(1N-6)
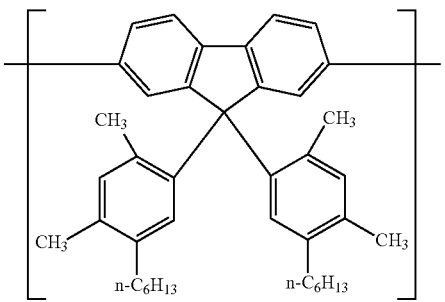
(1N-7)
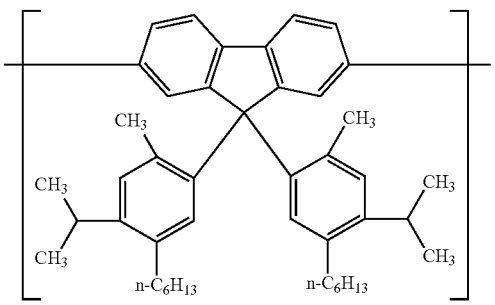

(1N-8)
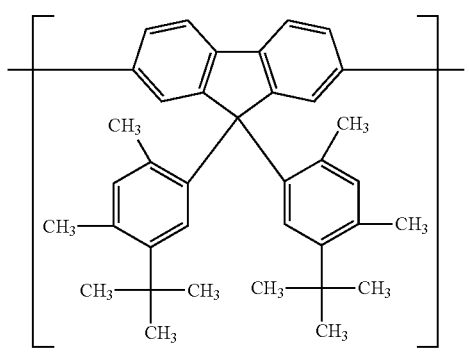
(1N-9)
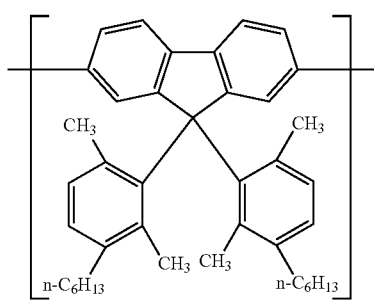
(1N-10)
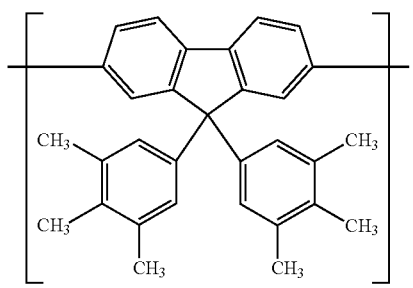
(1N-11)
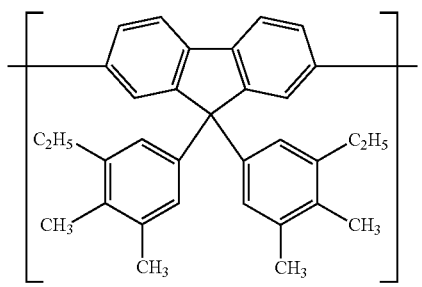
(1N-12)
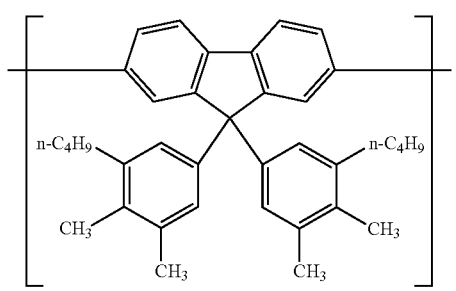
(1N-13)
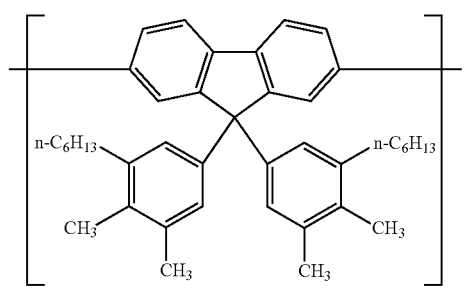
(1N-14)
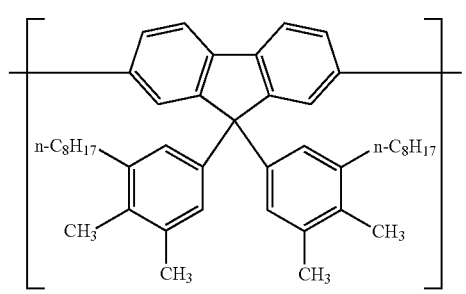
(1N-15)
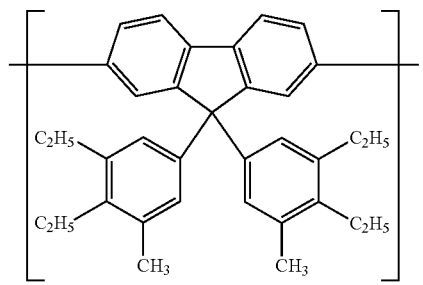
(1N-16)
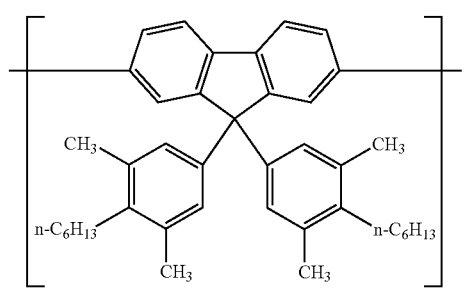
(1N-17)
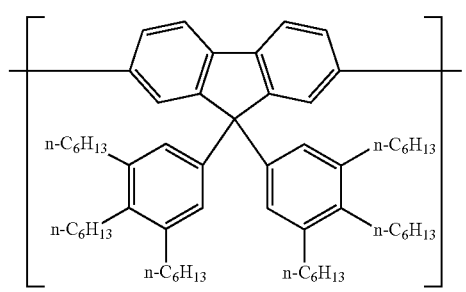

(1N-18) 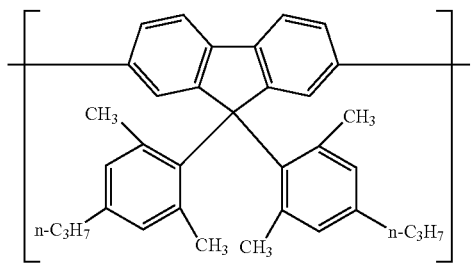
(1N-19) 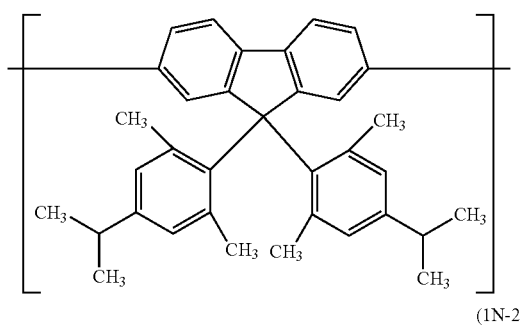
(1N-20) 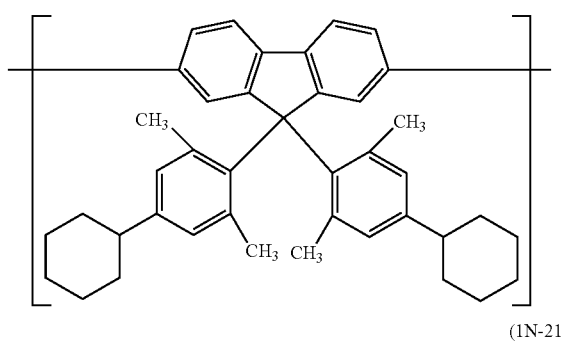
(1N-21) 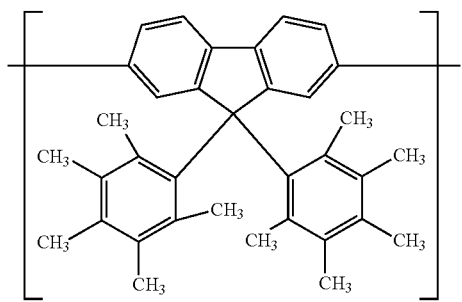
(1N-22) 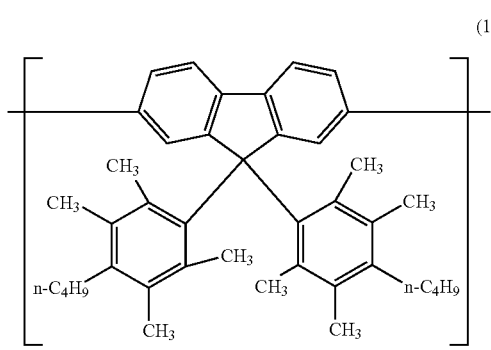
(1N-23) 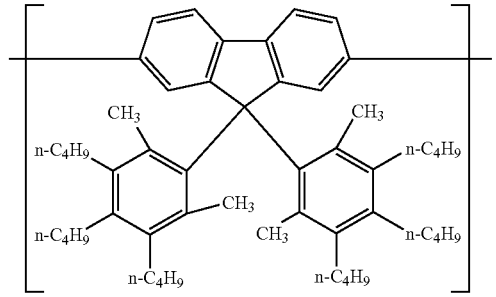
(1P-1) 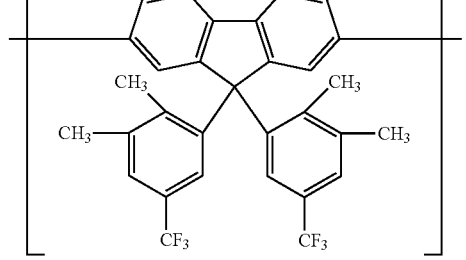
(1P-2) 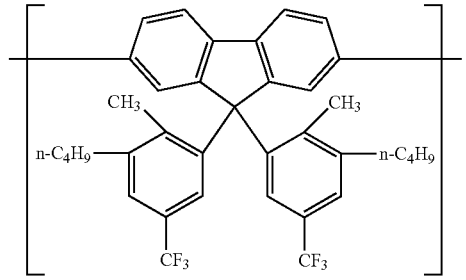
(1P-3) 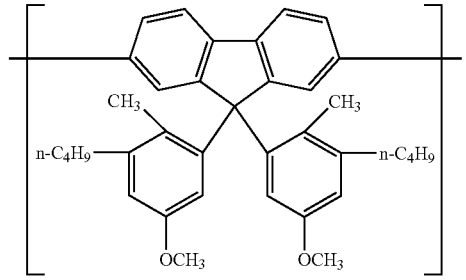
(1P-4) 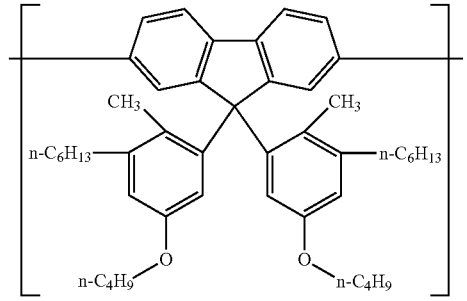

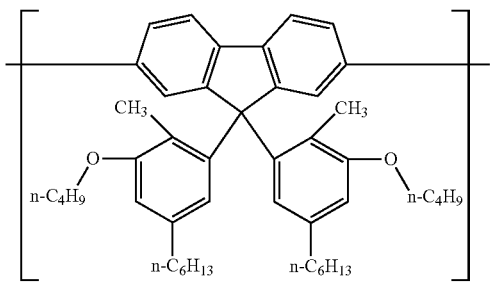
(1P-5)
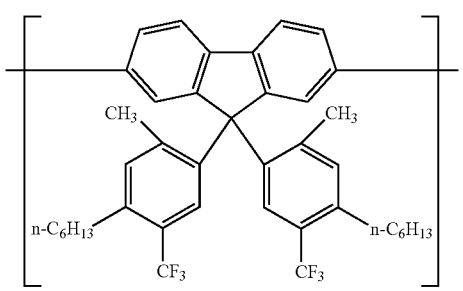
(1P-6)
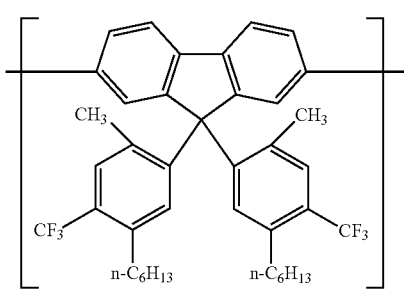
(1P-7)
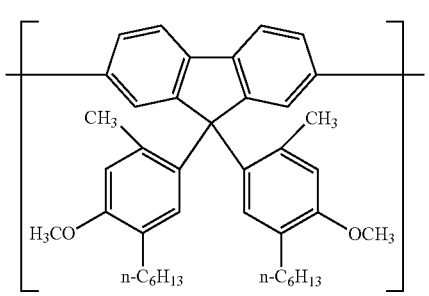
(1P-8)
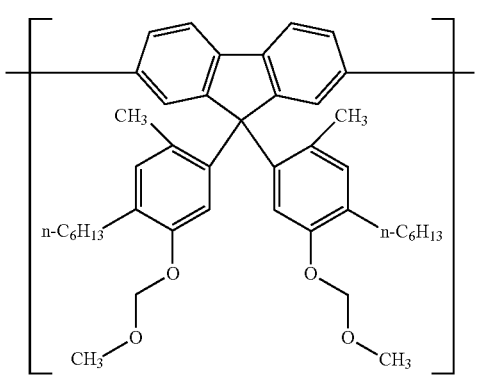
(1P-9)
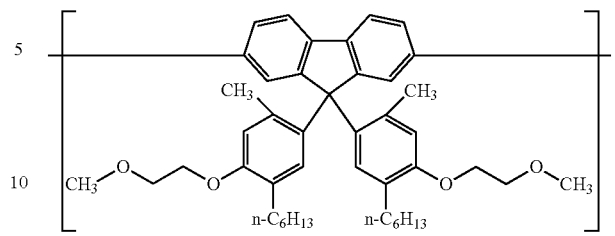
(1P-10)
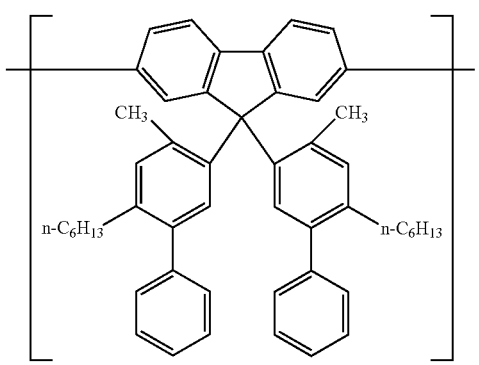
(1P-11)
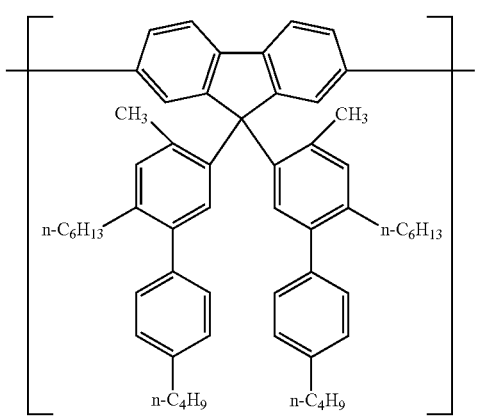
(1P-12)
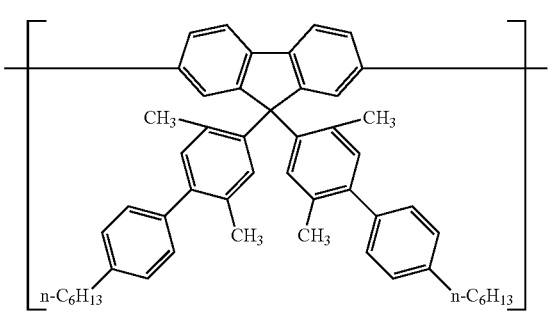
(1P-13)

(1P-14) 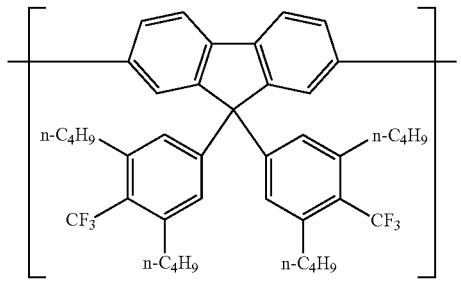
(1P-15) 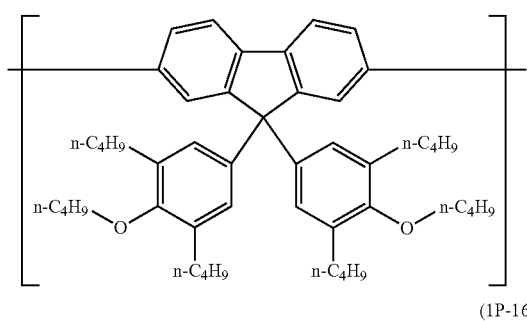
(1P-16) 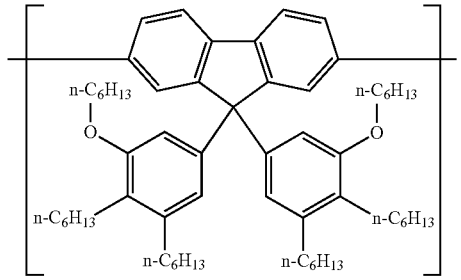
(1P-17) 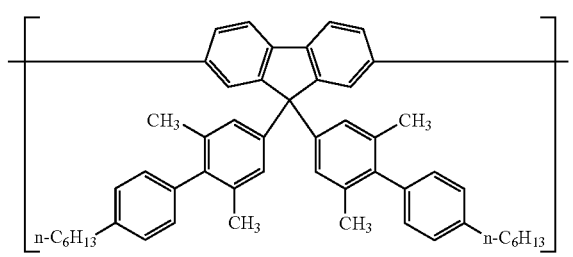
(1P-18) 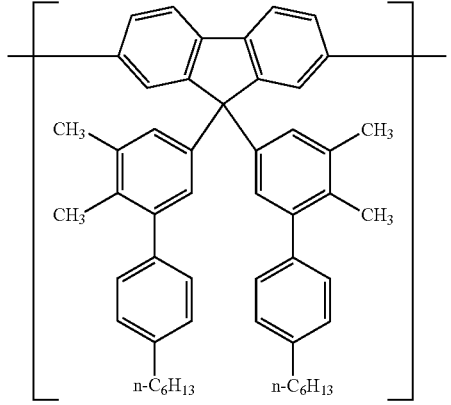
(1P-19) 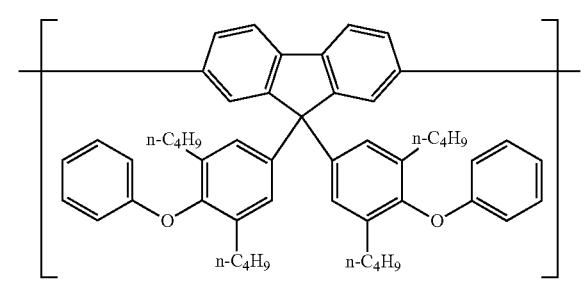
(1P-20) 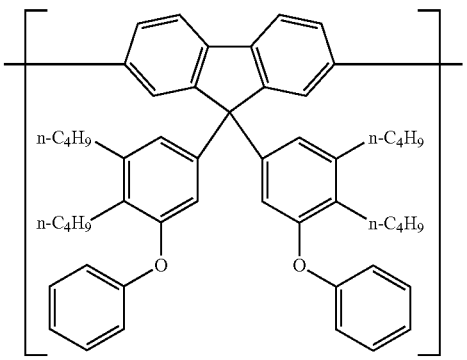
(1P-21) 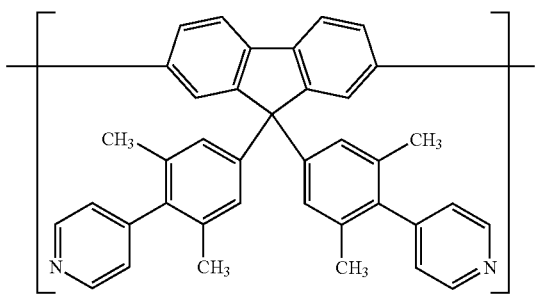
(1P-22) 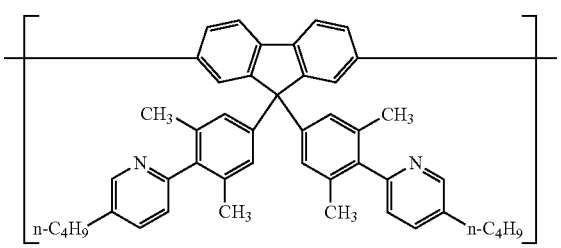
(1P-23) 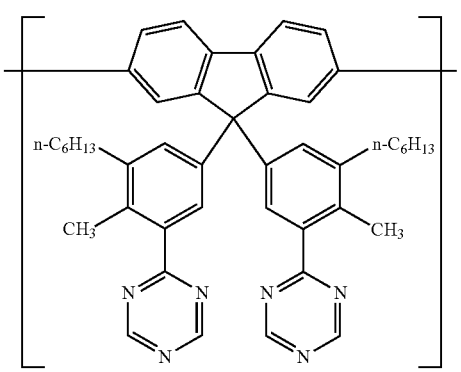

(1P-24) 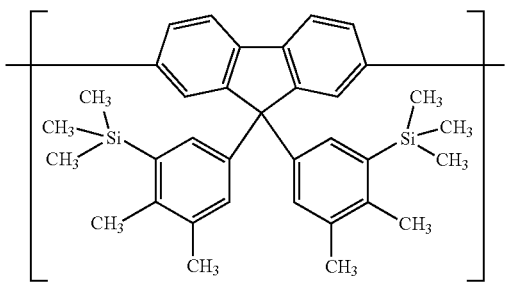
(1P-25) 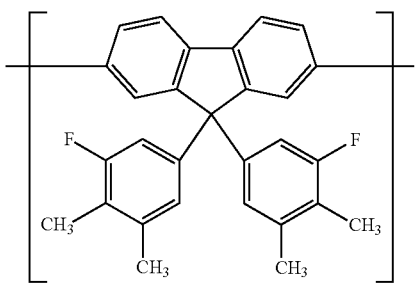
(1P-26) 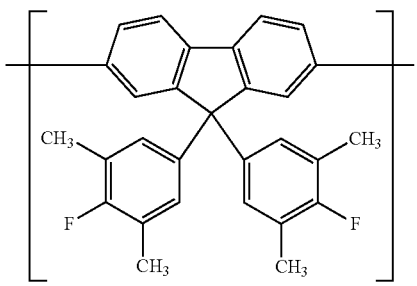
(1P-27) 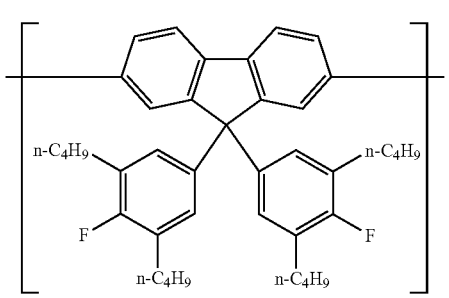
(1P-28) 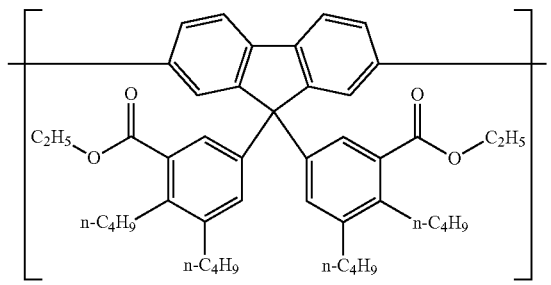
(1P-29) 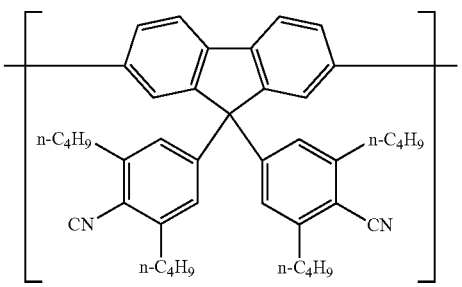
(1P-30) 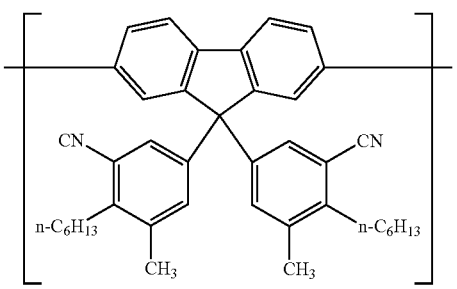
(1P-31) 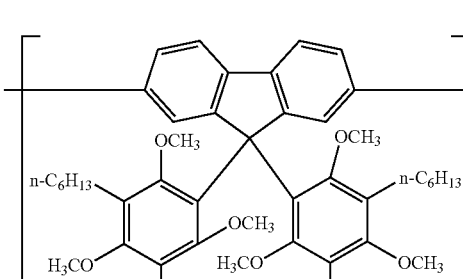
(1P-32) 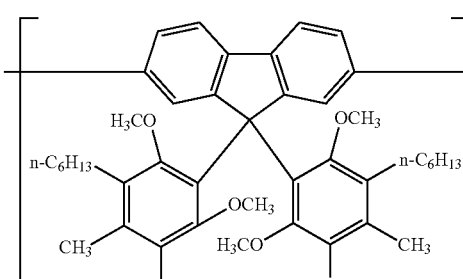
(1P-33) 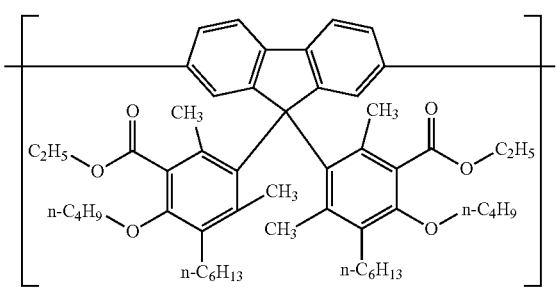

-continued (1Q-1)
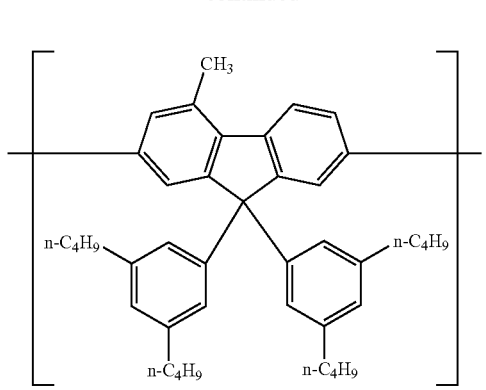

(1Q-2)
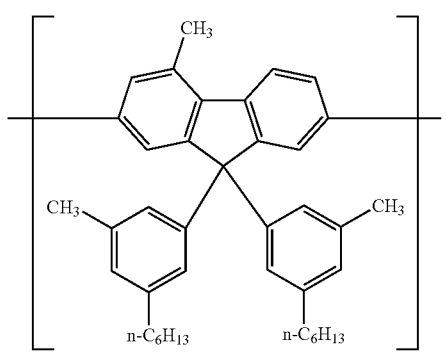

(1Q-3)
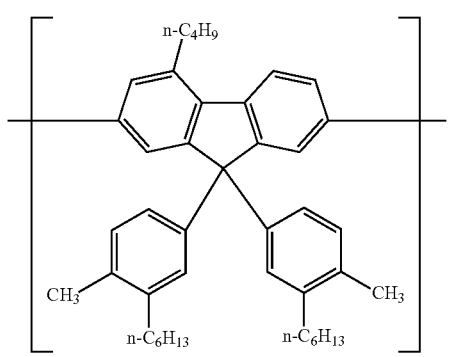

(1Q-4)
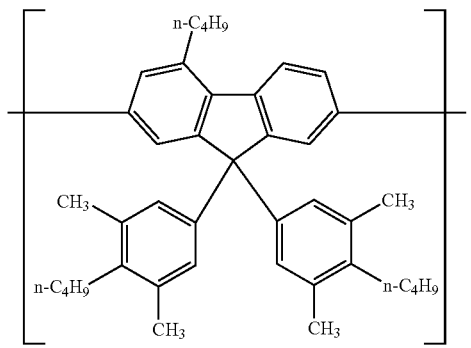

-continued (1Q-5)

(1Q-6)

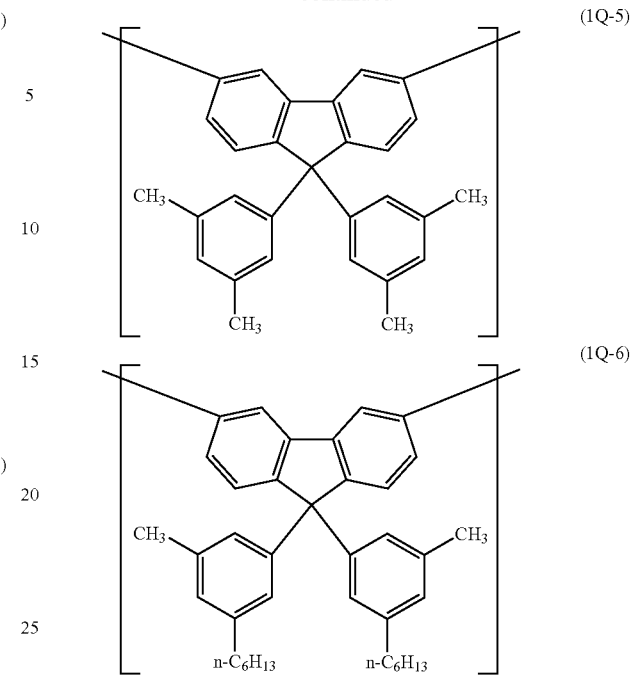

For further increased luminance life of the light-emitting device to be obtained, the polymer compound of this embodiment preferably comprises one or more constitutional units selected from the group consisting of constitutional units represented by formula (6) and constitutional units represented by formula (7), in addition to a constitutional unit represented by formula (1).

 (6)

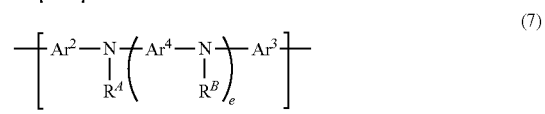 (7)

[In formula (6), $Ar^1$ represents an unsubstituted or substituted arylene group or unsubstituted or substituted divalent heterocyclic group. In formula (7), $Ar^2$, $Ar^3$ and $Ar^4$ each independently represent unsubstituted or substituted arylene group, an unsubstituted or substituted divalent aromatic heterocyclic group or an unsubstituted or substituted divalent group in which 2 aromatic rings are linked by a single bond. $R^A$ and $R^B$ each independently represent hydrogen atom, unsubstituted or substituted alkyl group, unsubstituted or substituted aryl group or an unsubstituted or substituted monovalent heterocyclic group. The letter e represents 0 or 1.]

In formula (6), $Ar^1$ represents an unsubstituted or substituted arylene group or unsubstituted or substituted divalent heterocyclic group. This is with the proviso that the constitutional unit represented by formula (6) is a constitutional unit having a different structure from the constitutional unit represented by formula (1).

The number of carbon atoms of an unsubstituted or substituted arylene group represented by $Ar^1$ in formula (6) will usually be 6-60, preferably 6-30, more preferably 6-18 and even more preferably 6-14, not including the number of carbon atoms of substituents.

An unsubstituted or substituted arylene group represented by $Ar^1$ may be an unsubstituted or substituted phenylene group such as unsubstituted or substituted 1,4-phenylene group, unsubstituted or substituted 1,3-phenylene group or unsubstituted or substituted 1,2-phenylene group; an unsubstituted or substituted naphthalenediyl group such as unsubstituted or substituted 1,4-naphthalenediyl group, unsubstituted or substituted 1,5-naphthalenediyl group or unsubstituted or substituted 2,6-naphthalenediyl group; an unsubstituted or substituted anthracenediyl group such as unsubstituted or substituted 1,4-anthracenediyl group, unsubstituted or substituted 1,5-anthracenediyl group, unsubstituted or substituted 2,6-anthracenediyl group or unsubstituted or substituted 9,10-anthracenediyl group; an unsubstituted or substituted phenanthrenediyl group such as unsubstituted or substituted 2,7-phenanthrenediyl group, an unsubstituted or substituted naphthacenediyl group such as unsubstituted or substituted 1,7-naphthacenediyl group, unsubstituted or substituted 2,8-naphthacenediyl group or unsubstituted or substituted 5,12-naphthacenediyl group; an unsubstituted or substituted fluorenediyl group such as unsubstituted or substituted 2,7-fluorenediyl group or unsubstituted or substituted 3,6-fluorenediyl group; an unsubstituted or substituted pyrenediyl group such as unsubstituted or substituted 1,6-pyrenediyl group, unsubstituted or substituted 1,8-pyrenediyl group, unsubstituted or substituted 2,7-pyrenediyl group or unsubstituted or substituted 4,9-pyrenediyl group; or an unsubstituted or substituted perylenediyl group such as unsubstituted or substituted 3,9-perylenediyl group or unsubstituted or substituted 3,10-perylenediyl group. Preferred are unsubstituted or substituted phenylene group, unsubstituted or substituted naphthalenediyl group, unsubstituted or substituted fluorenediyl group and unsubstituted or substituted pyrenediyl group, and more preferred are unsubstituted or substituted phenylene group and unsubstituted or substituted fluorenediyl group.

The number of carbon atoms of an unsubstituted or substituted divalent aromatic heterocyclic group represented by $Ar^1$ will usually be 4-60, preferably 4-30, more preferably 5-22 and particularly preferably 5-12, not including the number of carbon atoms of substituents.

An unsubstituted or substituted divalent aromatic heterocyclic group represented by $Ar^1$ may be an unsubstituted or substituted pyridinediyl group such as unsubstituted or substituted 2,5-pyridinediyl group and unsubstituted or substituted 2,6-pyridinediyl group; an unsubstituted or substituted furandiyl group such as unsubstituted or substituted 2,5-furandiyl group; an unsubstituted or substituted quinolinediyl group such as unsubstituted or substituted 2,6-quinolinediyl group; an unsubstituted or substituted isoquinolinediyl group such as unsubstituted or substituted 1,4-isoquinolinediyl group or unsubstituted or substituted 1,5-isoquinolinediyl group; an unsubstituted or substituted quinoxalinediyl group such as unsubstituted or substituted 5,8-quinoxalinediyl group; an unsubstituted or substituted carbazolediyl group such as unsubstituted or substituted 2,7-carbazolediyl group or unsubstituted or substituted 3,6-carbazolediyl group; an unsubstituted or substituted phenoxazinediyl group such as unsubstituted or substituted 3,7-phenoxazinediyl group; an unsubstituted or substituted phenothiazinediyl group such as unsubstituted or substituted 3,7-phenothiazinediyl group; or an unsubstituted or substituted dibenzosiloldiyl group such as unsubstituted or substituted 2,7-dibenzosiloldiyl group. Preferred are unsubstituted or substituted carbazolediyl group and unsubstituted or substituted phenoxazinediyl group, and more preferred are unsubstituted or substituted phenoxazinediyl groups.

When the aforementioned arylene group or divalent aromatic heterocyclic group has a substituent, the substituent is preferably unsubstituted or substituted alkyl group, unsubstituted or substituted alkoxy group, unsubstituted or substituted aryl group, unsubstituted or substituted aryloxy group, an unsubstituted or substituted monovalent heterocyclic group, unsubstituted or substituted silyl group, a halogen atom, alkoxycarbonyl group, carboxyl or cyano group. More preferred are unsubstituted or substituted alkyl group, unsubstituted or substituted alkoxy group and unsubstituted or substituted aryl group, and even more preferred are unsubstituted alkyl group and substituted aryl group.

The definitions and examples of unsubstituted or substituted alkyl group, unsubstituted or substituted alkoxy group, unsubstituted or substituted aryl group, unsubstituted or substituted aryloxy group, unsubstituted or substituted monovalent heterocyclic group, unsubstituted or substituted silyl group, halogen atom and alkoxycarbonyl group that may serve as the aforementioned substituents are the same as the definitions and examples of unsubstituted or substituted alkyl group, unsubstituted or substituted alkoxy group, unsubstituted or substituted aryl group, unsubstituted or substituted aryloxy group, unsubstituted or substituted monovalent heterocyclic group, unsubstituted or substituted silyl group, halogen atom and alkoxycarbonyl group represented by $R^3$ and $R^4$, respectively.

In order to further lengthen the luminance life of the light-emitting device to be obtained, the constitutional unit represented by formula (6) is preferably a constitutional unit represented by formula (8), (9), (10) or (11), and more preferably a constitutional unit represented by formula (8), (9) or (10).

(8)

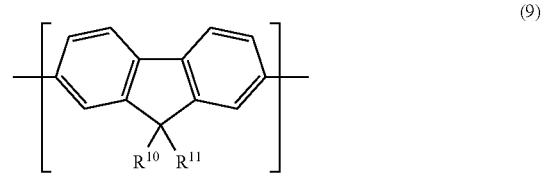

(9)

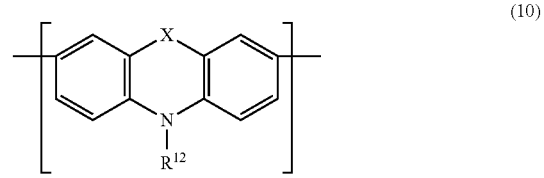

(10)

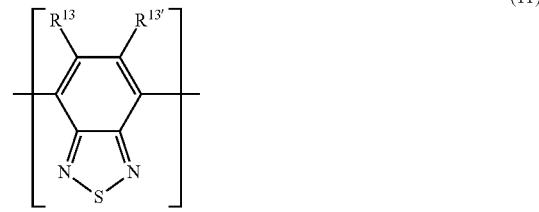

(11)

[In formula (8), $R^9$ represents unsubstituted or substituted alkyl group, unsubstituted or substituted alkoxy group, unsubstituted or substituted aryl group, unsubstituted or substituted aryloxy group, an unsubstituted or substituted monovalent heterocyclic group, unsubstituted or substituted silyl group, a halogen atom, alkoxycarbonyl group, carboxyl group or cyano group. The letter f represents an integer of 0 to 4. When multiple $R^9$ groups are present, they may be the same or different. In formula (9), $R^{10}$ and $R^{11}$ each independently represent hydrogen atom, unsubstituted or substituted alkyl group or unsubstituted or substituted aryl group. This is with the proviso that the constitutional unit represented by formula (9) is a constitutional unit having a different structure from the constitutional unit represented by formula (1).

In formula (10), $R^{12}$ represents unsubstituted or substituted alkyl group, unsubstituted or substituted aryl group or an unsubstituted or substituted monovalent heterocyclic group. X represents a single bond, —O—, —S— or —C($R^c$)$_2$—. $R^c$ represents unsubstituted or substituted alkyl group or unsubstituted or substituted aryl group. The two $R^c$ groups may be the same or different.

In formula (11), $R^{13}$ and $R^{13'}$ each independently represent hydrogen atom, unsubstituted or substituted alkyl group, unsubstituted or substituted alkoxy group, unsubstituted or substituted aryl group, unsubstituted or substituted aryloxy group, an unsubstituted or substituted monovalent heterocyclic group, unsubstituted or substituted silyl group, a halogen atom, alkoxycarbonyl group, carboxyl group or cyano group.]

In formula (8), $R^9$ represents unsubstituted or substituted alkyl group, unsubstituted or substituted alkoxy group, unsubstituted or substituted aryl group, unsubstituted or substituted aryloxy group, an unsubstituted or substituted monovalent heterocyclic group, unsubstituted or substituted silyl group, a halogen atom, alkoxycarbonyl group, carboxyl group or cyano group. Preferred are unsubstituted alkyl group, unsubstituted alkoxy group and substituted aryl group, more preferred are unsubstituted alkyl group and unsubstituted alkoxy group, and especially preferred are unsubstituted alkyl groups.

The definitions and examples of unsubstituted or substituted alkyl group, unsubstituted or substituted alkoxy group, unsubstituted or substituted aryl group, unsubstituted or substituted aryloxy group, unsubstituted or substituted monovalent heterocyclic group, unsubstituted or substituted silyl group, halogen atom and alkoxycarbonyl group represented by $R^9$ are the same as the definitions and examples of unsubstituted or substituted alkyl group, unsubstituted or substituted alkoxy group, unsubstituted or substituted aryl group, unsubstituted or substituted aryloxy group, unsubstituted or substituted monovalent heterocyclic group, unsubstituted or substituted silyl group, halogen atom and alkoxycarbonyl group represented by $R^3$ and $R^4$, respectively.

In formula (8), f represents an integer of 0 to 4, and it preferably represents an integer of 0 to 2.

Constitutional units represented by formula (8) include constitutional units represented by the following formulas (8A-1) to (8A-9) and formulas (8B-1) to (8B-12).

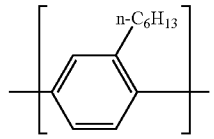
(8A-1)

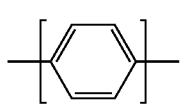
(8A-2)

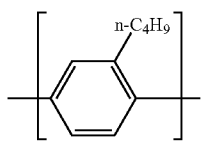

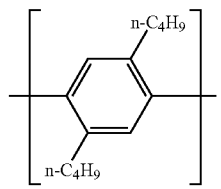
(8A-3)

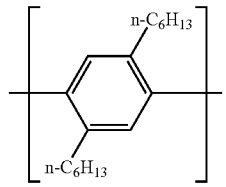
(8A-4)

(8A-5)

(8A-6)

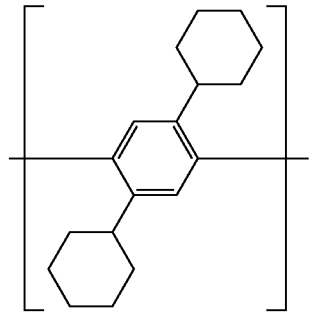

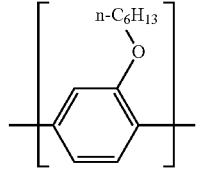
(8A-7)

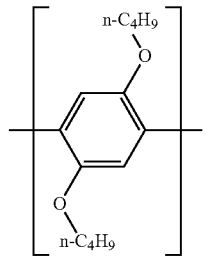
(8A-8)

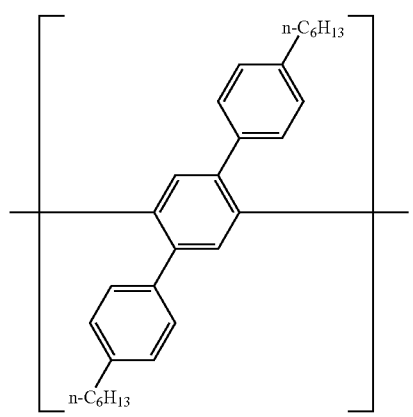
(8A-9)
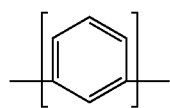
(8B-1)
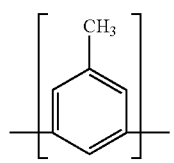
(8B-2)
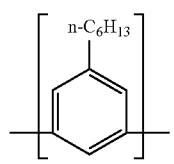
(8B-3)
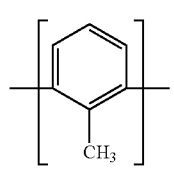
(8B-4)
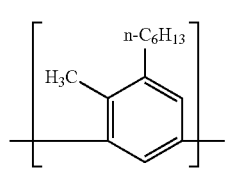
(8B-5)
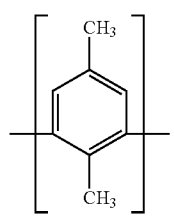
(8B-6)
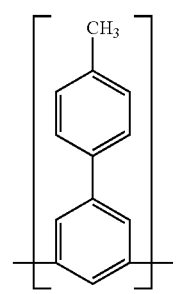
(8B-7)
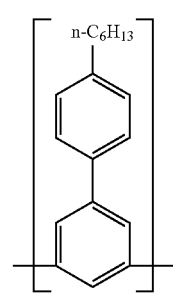
(8B-8)
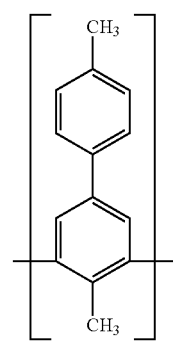
(8B-9)
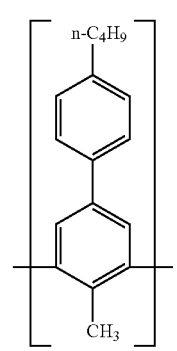
(8B-11)
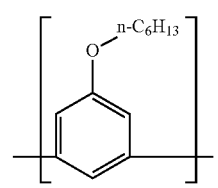
(8B-11)

(8B-12)

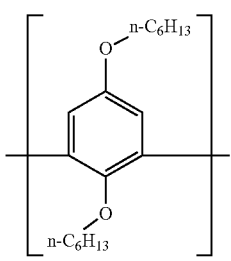

In formula (9), $R^{10}$ and $R^{11}$ each independently represent hydrogen atom, unsubstituted or substituted alkyl group or unsubstituted or substituted aryl group.

The definitions and examples of unsubstituted or substituted alkyl group and unsubstituted or substituted aryl group represented by $R^{10}$ and $R^{11}$ are the same as the definitions and examples of unsubstituted or substituted alkyl group and unsubstituted or substituted aryl group represented by $R^3$ and $R^4$, respectively.

Constitutional units represented by formula (9) include constitutional units represented by the following formulas (9A-1) to (9A-31).

(9A-1) (9A-2)

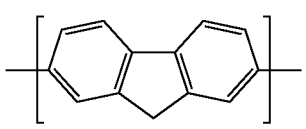

(9A-3) (9A-4)

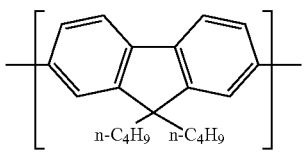

(9A-5) (9A-6)

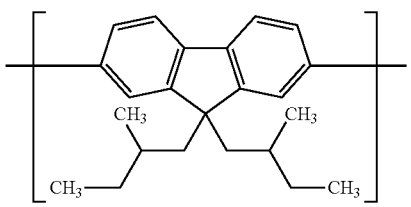

(9A-7) (9A-8)

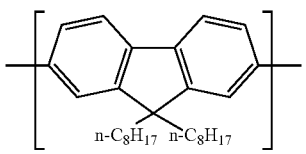

(9A-9) (9A-10)

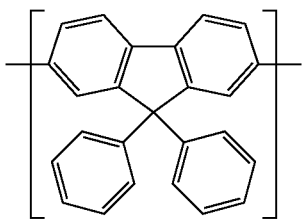

(9A-11) (9A-12)

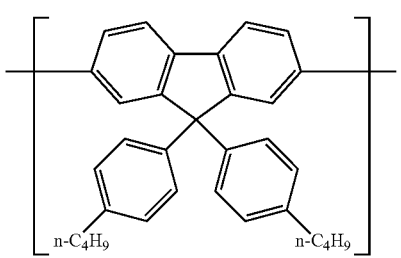
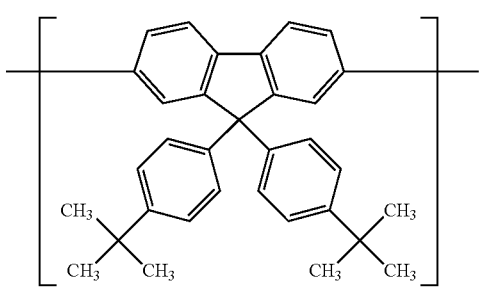

-continued
(9A-13) 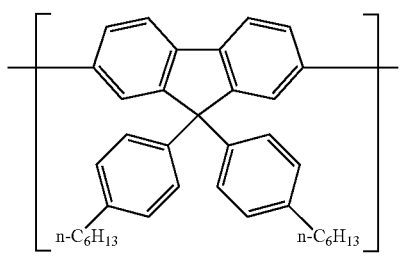
(9A-14) 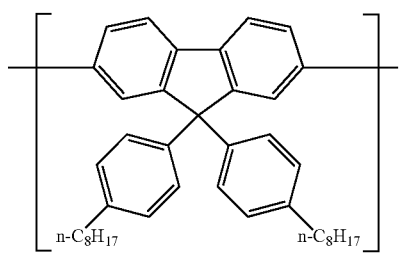
(9A-15) 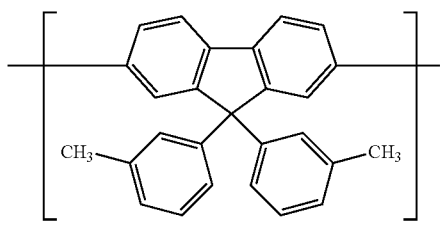
(9A-16) 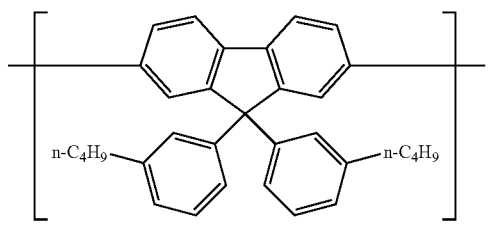
(9A-17) 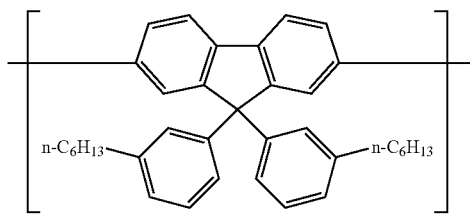
(9A-18) 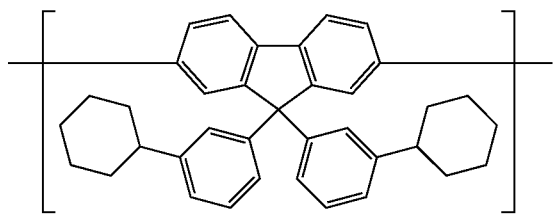
(9A-19) 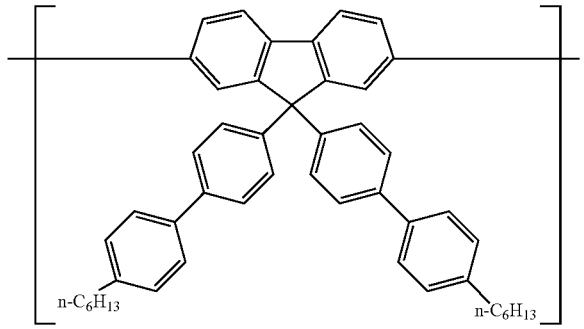
(9A-20) 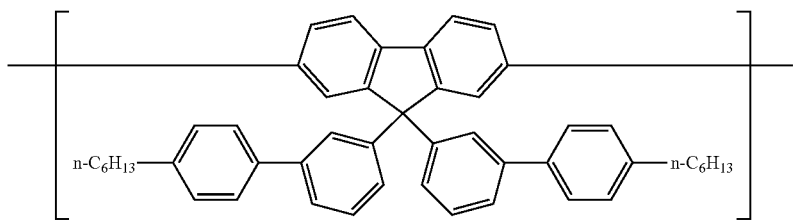
(9A-21) 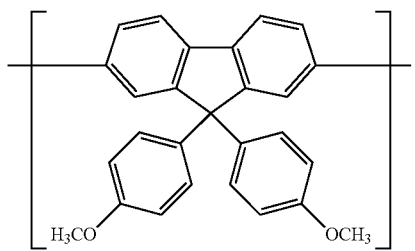
(9A-22) 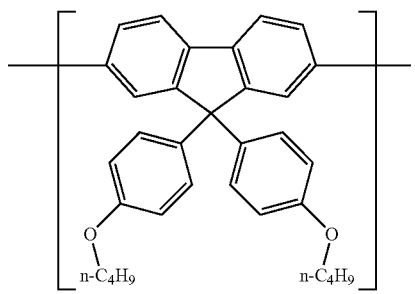

-continued
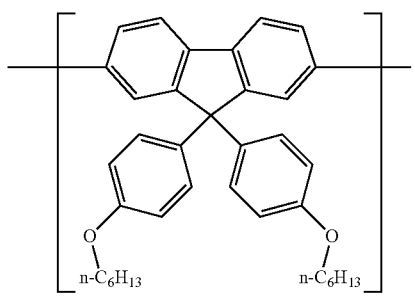
(9A-23)
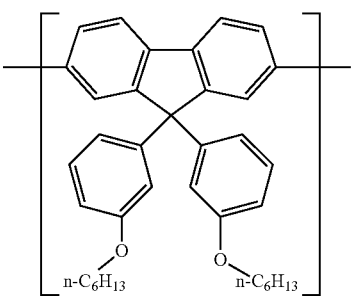
(9A-24)
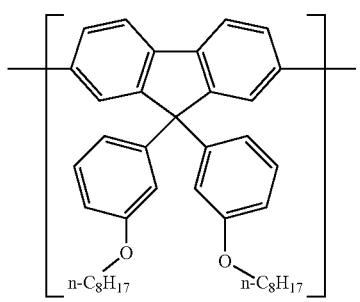
(9A-25)
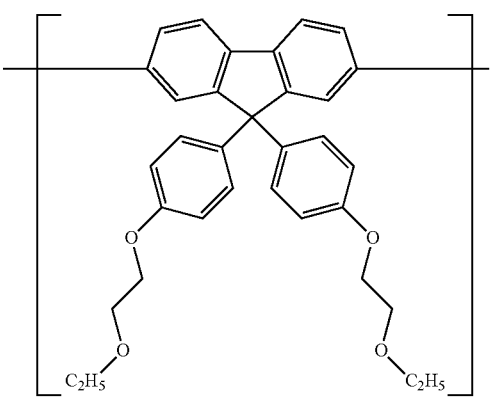
(9A-26)
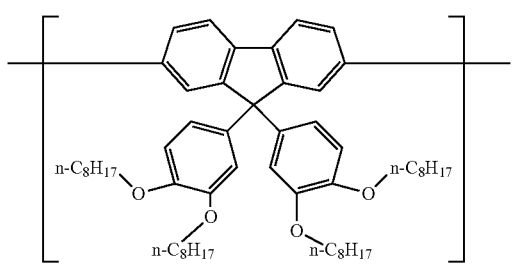
(9A-27)
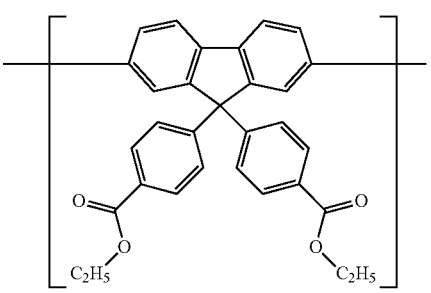
(9A-28)
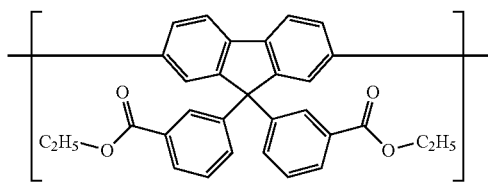
(9A-29)
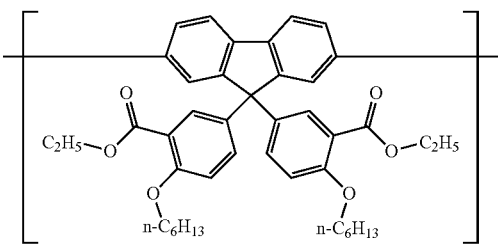
(9A-30)
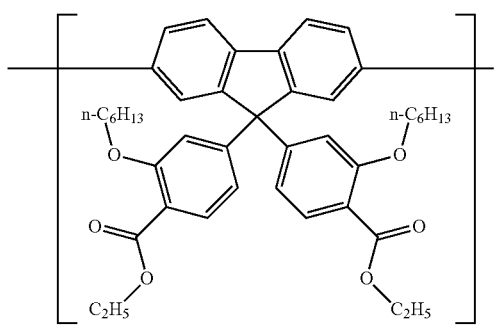
(9A-31)

In formula (10), $R^{12}$ represents unsubstituted or substituted alkyl group, unsubstituted or substituted aryl group or an unsubstituted or substituted monovalent heterocyclic group.

The definitions and examples of unsubstituted or substituted alkyl group, unsubstituted or substituted aryl group and unsubstituted or substituted monovalent heterocyclic group represented by $R^{12}$ are the same as the definitions and examples of unsubstituted or substituted alkyl group, unsubstituted or substituted aryl group and unsubstituted or substituted monovalent heterocyclic group represented by $R^3$ and $R^4$.

In formula (10), X represents a single bond, —O—, —S— or —C($R^c$)$_2$—, preferably —O— or —S—, and more preferably —O—. $R^c$ represents unsubstituted or substituted alkyl group or unsubstituted or substituted aryl group. The definitions and examples of unsubstituted or substituted alkyl group and unsubstituted or substituted aryl group are the same as the definitions and examples of unsubstituted or substituted alkyl group and unsubstituted or substituted aryl group represented by $R^3$ and $R^4$, respectively.

Constitutional units represented by formula (10) include constitutional units represented by the following formulas (10A-1) to (10A-17).

(10A-1)

(10A-2)

(10A-3)

(10A-4)

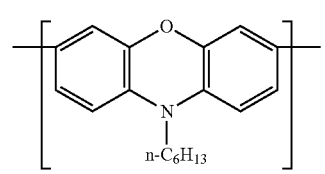

-continued (10A-5)

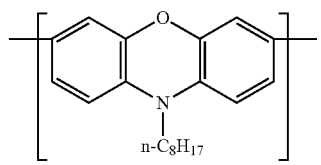

(10A-6)

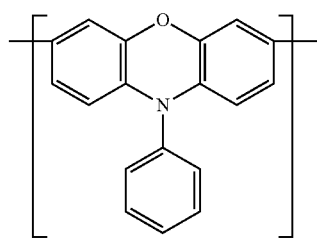

(10A-7)

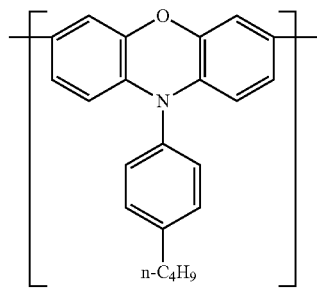

(10A-8)

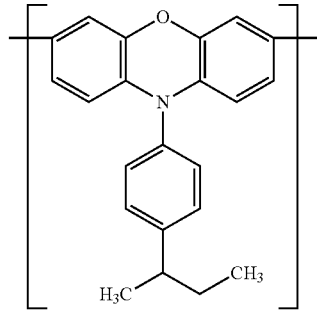

(10A-9)

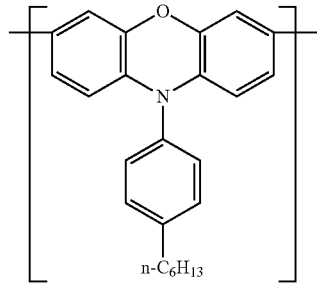

(10A-10)

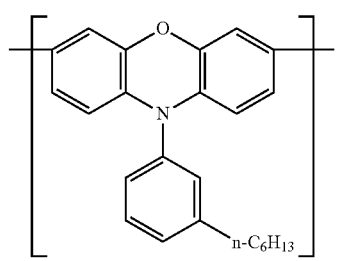

(10A-11) 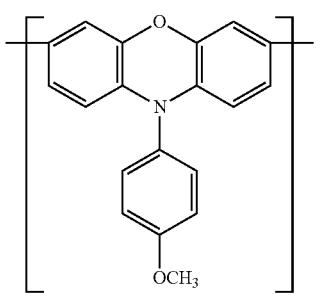

(10A-12) 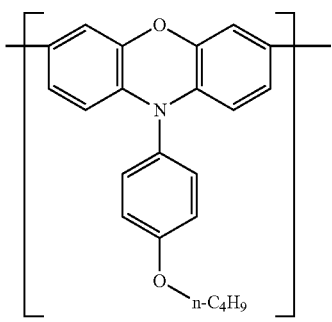

(10A-13) 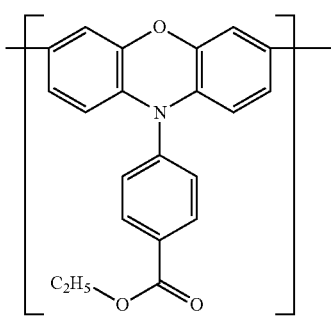

(10A-14) 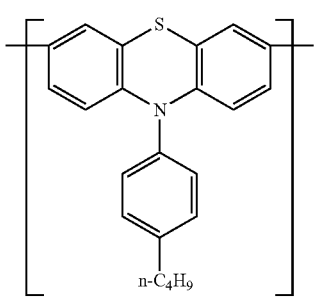

(10A-15) 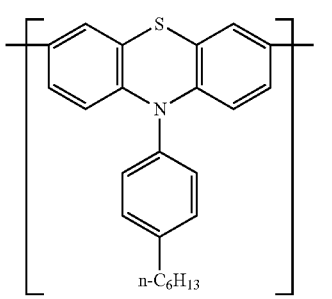

(10A-16) 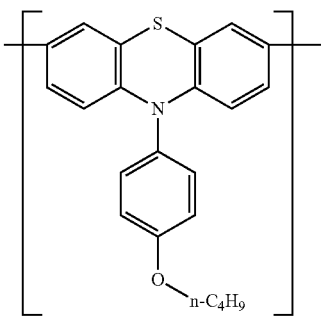

(10A-17) 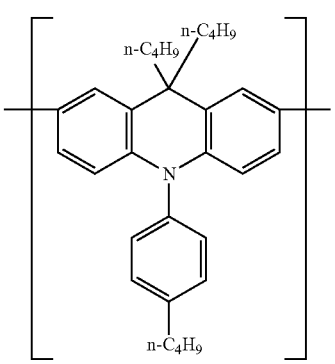

In formula (11), $R^{13}$ and $R^{13'}$ each independently represent hydrogen atom, unsubstituted or substituted alkyl group, unsubstituted or substituted alkoxy group, unsubstituted or substituted aryl group, unsubstituted or substituted aryloxy group, an unsubstituted or substituted monovalent heterocyclic group, unsubstituted or substituted 10 silyl group, a halogen atom, alkoxycarbonyl group, carboxyl group or cyano group.

The definitions and examples of unsubstituted or substituted alkyl, unsubstituted or substituted alkoxy, unsubstituted or substituted aryl, unsubstituted or substituted aryloxy, unsubstituted or substituted monovalent heterocyclic, unsubstituted or substituted silyl, halogen atom and alkoxycarbonyl groups represented by $R^{13}$ and $R^{13'}$ are the same as the definitions and examples of unsubstituted or substituted alkyl, unsubstituted or substituted alkoxy, unsubstituted or substituted aryl, unsubstituted or substituted aryloxy, unsubstituted or substituted monovalent heterocyclic, unsubstituted or substituted silyl, halogen atom and alkoxycarbonyl groups represented by $R^3$ and $R^4$, respectively.

Constitutional units represented by formula (11) include constitutional units represented by the following formulas (11A-1) to (11A-7).

(11A-1) 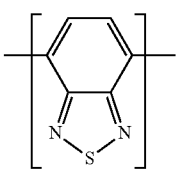

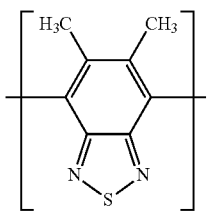 (11A-2)

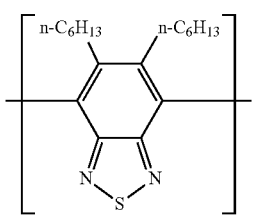 (11A-3)

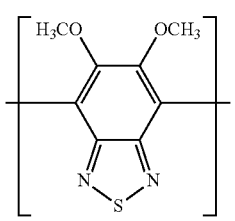 (11A-4)

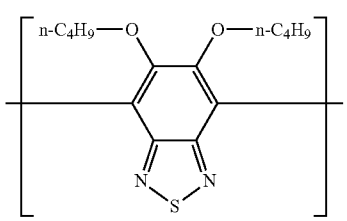 (11A-5)

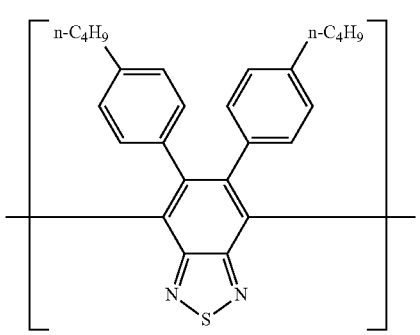 (11A-6)

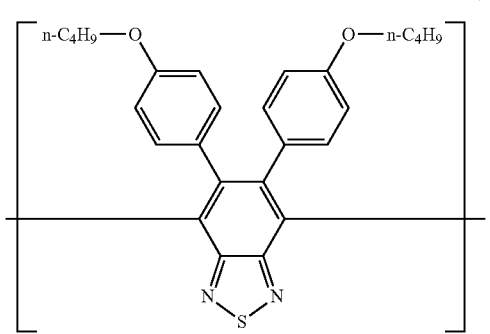 (11A-7)

In formula (7), $Ar^2$, $Ar^3$ and $Ar^4$ each independently represent unsubstituted or substituted arylene group, an unsubstituted or substituted divalent aromatic heterocyclic group or an unsubstituted or substituted divalent group in which 2 aromatic rings are linked by a single bond.

The number of carbon atoms of an unsubstituted or substituted arylene group represented by $Ar^2$, $Ar^3$ or $Ar^4$ is usually 6-60, preferably 6-30, more preferably 6-18, even more preferably 6-10 and particularly preferably 6, not including the number of carbon atoms of substituents.

Unsubstituted arylene groups represented by $Ar^2$, $Ar^3$ and $Ar^4$ include phenylene groups such as 1,3-phenylene group and 1,4-phenylene group; naphthalenediyl groups such as 1,4-naphthalenediyl group and 2,6-naphthalenediyl group; anthracenediyl groups such as 9,10-anthracenediyl group; phenanthrenediyl groups such as 2,7-phenanthrenediyl group; naphthacenediyl groups such as 5,12-naphthacenediyl group; fluorenediyl groups such as 2,7-fluorenediyl group; perylenediyl groups such as 3,8-perylenediyl group; and chrysenediyl groups such as 2,8-chrysenediyl group and 6,12-chrysenediyl group.

The number of carbon atoms of an unsubstituted or substituted divalent aromatic heterocyclic group represented by $Ar^2$, $Ar^3$ or $Ar^4$ will usually be 4-60, preferably 4-20, more preferably 4-9 and even more preferably 4 or 5, not including the number of carbon atoms of substituents.

Unsubstituted divalent aromatic heterocyclic groups represented by $Ar^2$, $Ar^3$ and $Ar^4$ include pyrolediyl groups such as N-methyl-2,5-pyrrolediyl group; furandiyl groups such as 2,5-furandiyl group; pyridinediyl groups such as 2,5-pyridinediyl group and 2,6-pyridinediyl group; quinolinediyl groups such as 2,4-quinolinediyl group and 2,6-quinolinediyl group; isoquinolinediyl groups such as 1,4-isoquinolinediyl group and 1,5-isoquinolinediyl group; phenoxazinediyl groups such as 3,7-phenoxazinediyl group; and carbazolediyl groups such as 3,6-carbazolediyl group.

An unsubstituted divalent group having 2 aromatic rings linked by a single bond, represented by $Ar^2$, $Ar^3$ or $Ar^4$, is a divalent group resulting by forming a single bond between one bonding site of a divalent group selected from the group consisting of unsubstituted or substituted arylene groups and unsubstituted or substituted divalent heterocyclic groups, and one bonding site of another divalent group selected from among the same groups. Specifically, these include the groups represented by the following formulas (7A-1) to (7A-4). They are preferably groups represented by formulas (7A-1) to (7A-3), and more preferably groups represented by the following formula (7A-1).

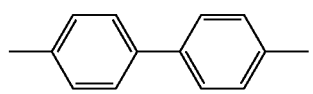 (7A-1)

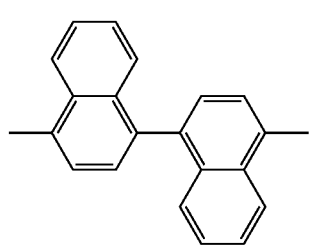 (7A-2)

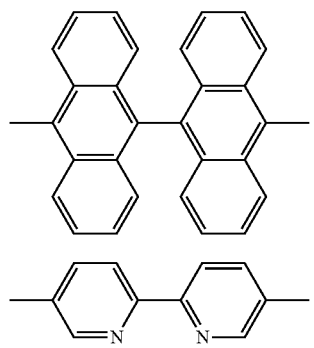

(7A-3)

(7A-4)

Ar² and Ar³ are preferably unsubstituted or substituted arylene groups, more preferably unsubstituted or substituted 1,3-phenylene group, unsubstituted or substituted 1,4-phenylene group, unsubstituted or substituted 1,4-naphthalenediyl group or unsubstituted or substituted 2,6-naphthalenediyl groups, even more preferably unsubstituted or substituted 1,4-phenylene group or unsubstituted or substituted 1,4-naphthalenediyl groups, and particularly preferably unsubstituted or substituted 1,4-phenylene groups.

Ar⁴ is preferably unsubstituted or substituted arylene group or an unsubstituted or substituted divalent group in which 2 aromatic rings are linked by a single bond, more preferably unsubstituted or substituted 1,3-phenylene group, unsubstituted or substituted 1,4-phenylene group, unsubstituted or substituted 1,4-naphthalenediyl group, unsubstituted or substituted 2,7-fluorenediyl group, 9,10-anthracenediyl group or an unsubstituted or substituted group represented by formula (7A-1), even more preferably unsubstituted or substituted 1,4-phenylene group, unsubstituted or substituted 1,4-naphthalenediyl group, unsubstituted or substituted 2,7-fluorenediyl group, 9,10-anthracenediyl group or an unsubstituted or substituted group represented by formula (7A-1), and particularly preferably unsubstituted 1,4-phenylene group, substituted 2,7-fluorenediyl group or an unsubstituted group represented by formula (7A-1).

When the groups represented by Ar², Ar³ and Ar⁴ are substituted, their substituents are preferably unsubstituted or substituted alkyl group, unsubstituted or substituted alkoxy group, unsubstituted or substituted aryl group, unsubstituted or substituted aryloxy group, unsubstituted or substituted monovalent heterocyclic group, unsubstituted or substituted silyl group, halogen atom, alkoxycarbonyl group, carboxyl or cyano groups. They are more preferably unsubstituted alkyl group, unsubstituted alkoxy group or unsubstituted or substituted aryl group, and even more preferably unsubstituted alkyl groups.

The definitions and examples of unsubstituted or substituted alkyl group, unsubstituted or substituted alkoxy group, unsubstituted or substituted aryl group, unsubstituted or substituted aryloxy group, unsubstituted or substituted monovalent heterocyclic group, unsubstituted or substituted silyl group, halogen atom and alkoxycarbonyl groups that may serve as substituents are the same as the definitions and examples of unsubstituted or substituted alkyl group, unsubstituted or substituted alkoxy group, unsubstituted or substituted aryl group, unsubstituted or substituted aryloxy group, unsubstituted or substituted monovalent heterocyclic group, unsubstituted or substituted silyl group, halogen atom and alkoxycarbonyl groups represented by $R^3$ and $R^4$, respectively.

$R^A$ and $R^B$ in formula (7) each independently represent hydrogen atom, unsubstituted or substituted alkyl group, unsubstituted or substituted aryl group or an unsubstituted or substituted monovalent heterocyclic group.

The definitions and examples of unsubstituted or substituted alkyl group, unsubstituted or substituted aryl group and unsubstituted or substituted monovalent heterocyclic groups represented by $R^A$ and $R^B$ are the same as the definitions and examples of unsubstituted or substituted alkyl group, unsubstituted or substituted aryl group and unsubstituted or substituted monovalent heterocyclic groups represented by $R^3$ and $R^4$, respectively.

In formula (7), e is 0 or 1 and preferably 1.

In order to further lengthen the luminance life of the obtained light-emitting device, the constitutional unit represented by formula (7) is preferably a constitutional unit represented by formula (14).

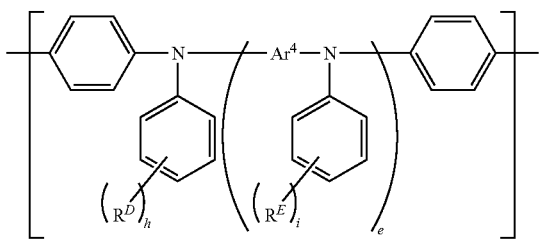

(14)

[In formula (14), Ar⁴ and e have the same meanings specified above. $R^D$ and $R^E$ each independently represent unsubstituted or substituted alkyl group, unsubstituted or substituted alkoxy group, unsubstituted or substituted aryl group, unsubstituted or substituted aryloxy group, an unsubstituted or substituted monovalent heterocyclic group, unsubstituted or substituted silyl group, a halogen atom, alkoxycarbonyl group, carboxyl group or cyano group. The letters h and i each independently represent an integer of 0 to 5. When multiple groups are present for $R^D$ and $R^E$, they may be the same or different.]

In formula (14), $R^D$ and $R^E$ each independently represent unsubstituted or substituted alkyl group, unsubstituted or substituted alkoxy group, unsubstituted or substituted aryl group, unsubstituted or substituted aryloxy group, an unsubstituted or substituted monovalent heterocyclic group, unsubstituted or substituted silyl group, a halogen atom, alkoxycarbonyl group, carboxyl group or cyano group.

The definitions and examples of unsubstituted or substituted alkyl group, unsubstituted or substituted alkoxy group, unsubstituted or substituted aryl group, unsubstituted or substituted aryloxy group, unsubstituted or substituted monovalent heterocyclic group, unsubstituted or substituted silyl group, halogen atom and alkoxycarbonyl groups represented by $R^D$ and $R^E$ are the same as the definitions and examples of unsubstituted or substituted alkyl group, unsubstituted or substituted alkoxy group, unsubstituted or substituted aryl group, unsubstituted or substituted aryloxy group, unsubstituted or substituted monovalent heterocyclic group, unsubstituted or substituted silyl group, halogen atom and alkoxycarbonyl groups represented by $R^3$ and $R^4$, respectively.

In formula (14), h and i each independently represent an integer of 0 to 5, preferably represent an integer of 1 to 3, and even more preferably represent 1 or 3.

Constitutional units represented by formula (14) include constitutional units represented by the following formulas (14A-1) to (14A-30).

(14A-1) 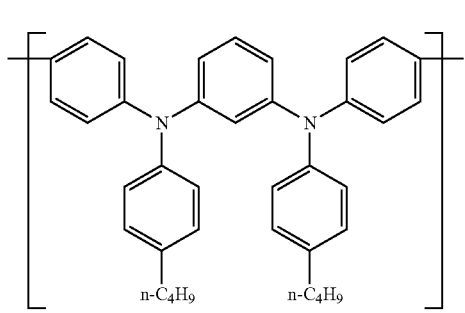
(14A-2) 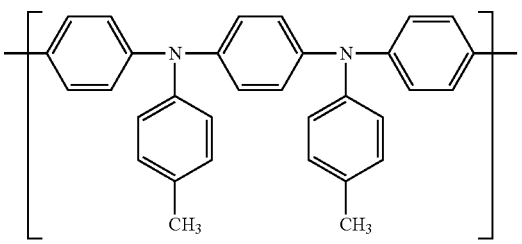
(14A-3) 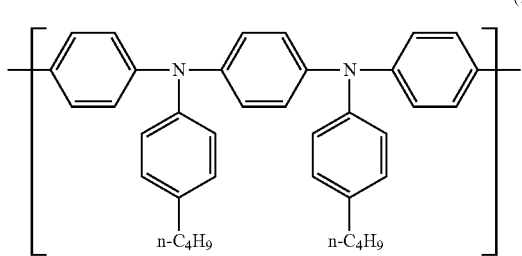
(14A-4) 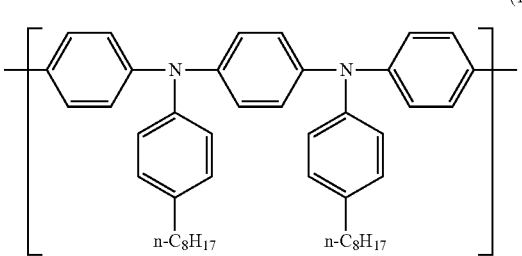
(14A-5) 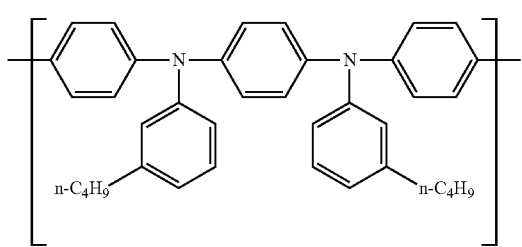
(14A-6) 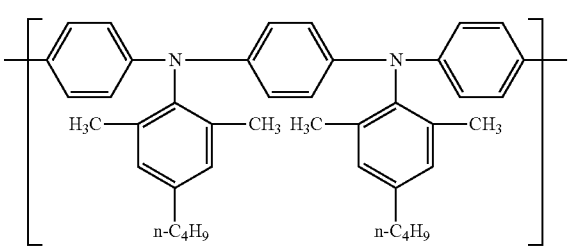
(14A-7) 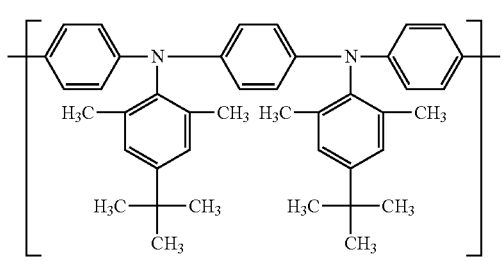
(14A-8) 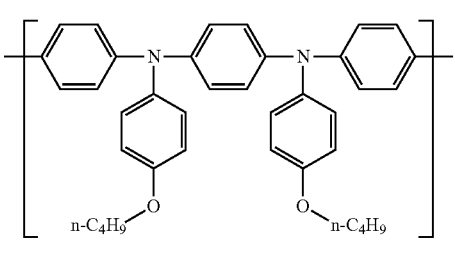
(14A-9) 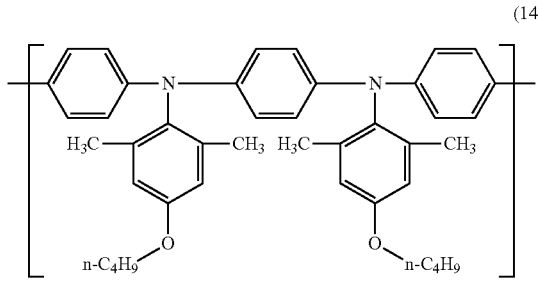
(14A-10) 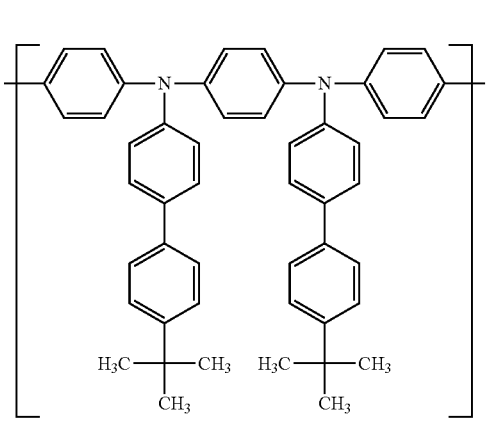

-continued
(14A-11)
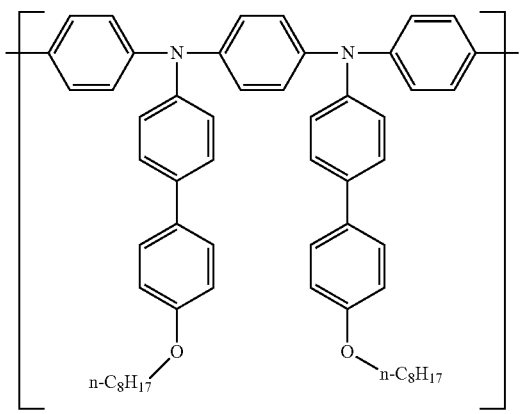
(14A-12)
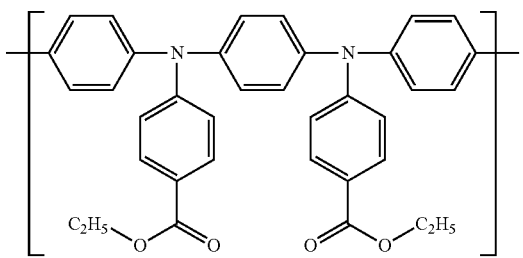
(14A-13)
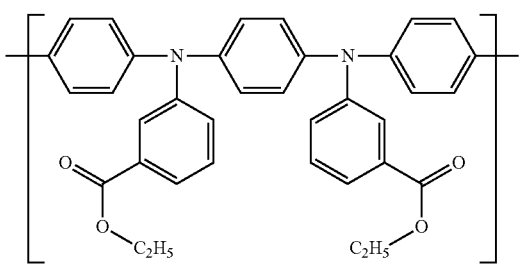
(14A-14)
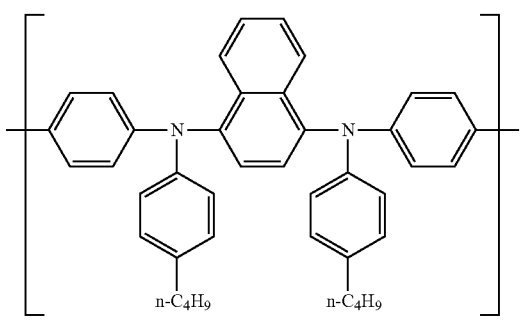
(14A-15)
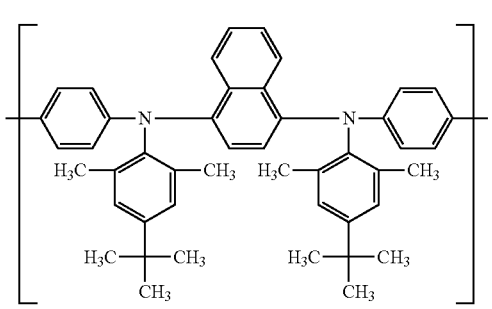
(14A-16)
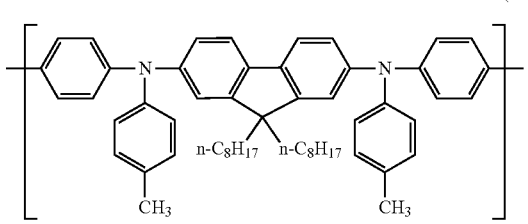
(14A-17)
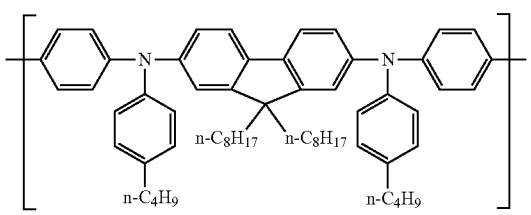
(14A-18)
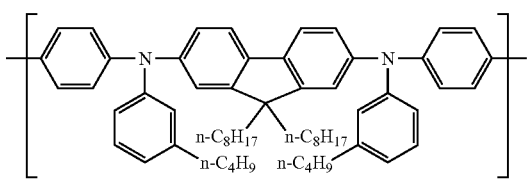
(14A-19)
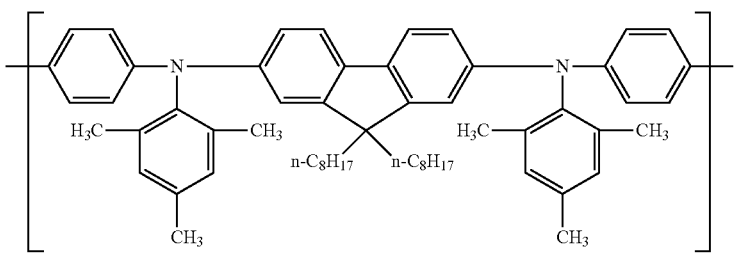

-continued
(14A-20)
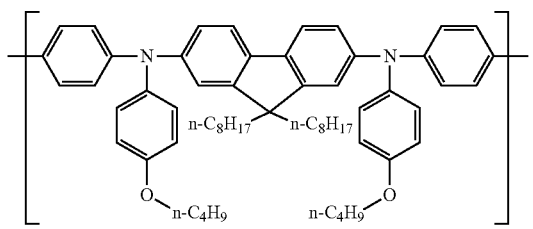
(14A-21)
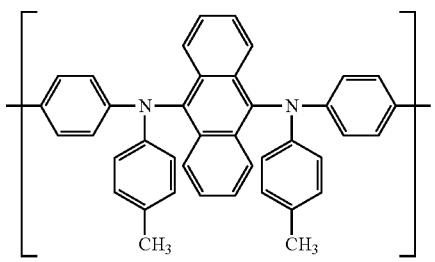
(14A-22)
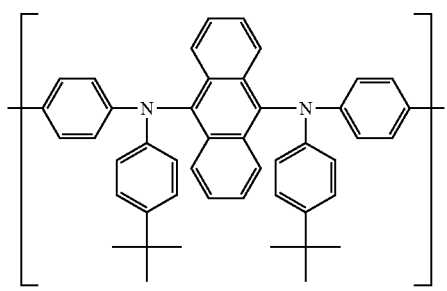
(14A-23)
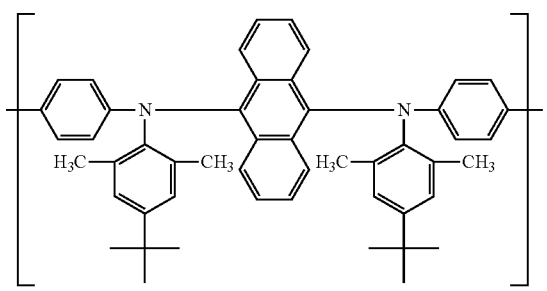
(14A-24)
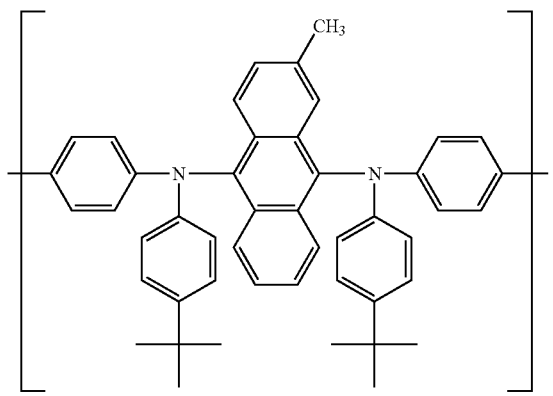
(14A-25)
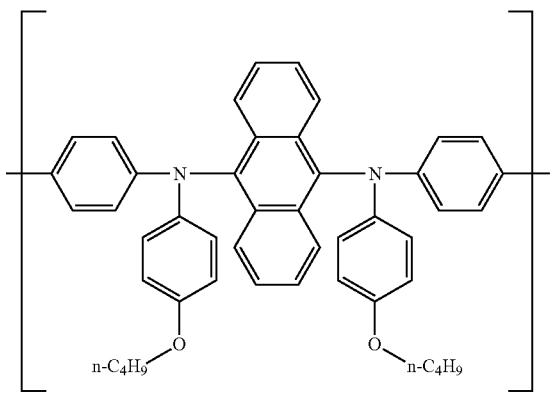
(14A-26)
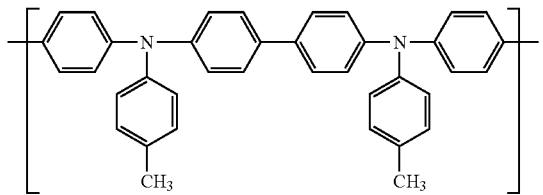
(14A-27)
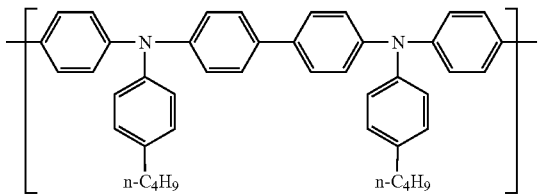
(14A-28)
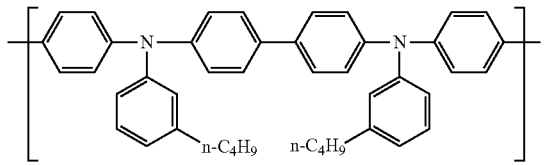
(14A-29)
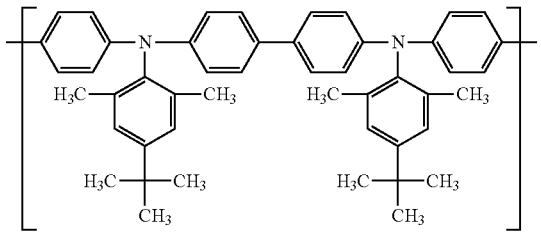

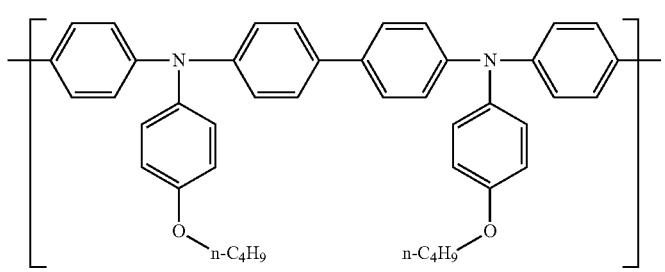

(14A-30)

For further increased driving voltage and luminous efficiency of the light-emitting device to be obtained, the polymer compound of this embodiment preferably contains a constitutional unit represented by formula (12) composed of a constitutional unit which is a combination of multiple constitutional units represented by formula (6), and at least one constitutional unit selected from the group consisting of constitutional units represented by formula (13).

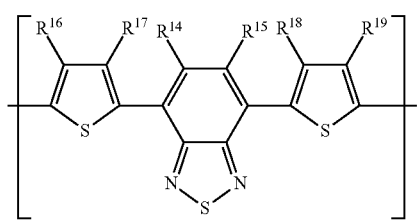

(12)

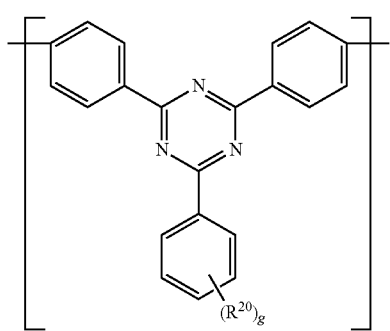

(13)

[In formula (12), $R^{14}$, $R^{15}$, $R^{16}$, $R^{17}$, $R^{18}$ and $R^{19}$ each independently represent hydrogen atom, unsubstituted or substituted alkyl group, unsubstituted or substituted alkoxy group, unsubstituted or substituted aryl group, unsubstituted or substituted aryloxy group, an unsubstituted or substituted monovalent heterocyclic group, unsubstituted or substituted silyl group, a halogen atom, alkoxycarbonyl group, carboxyl group or cyano group.
In formula (13), $R^{20}$ represents unsubstituted or substituted alkyl group, unsubstituted or substituted alkoxy group, unsubstituted or substituted aryl group, unsubstituted or substituted aryloxy group, an unsubstituted or substituted monovalent heterocyclic group, unsubstituted or substituted silyl group, a halogen atom, alkoxycarbonyl group, carboxyl group or cyano group. The letter g represents an integer of 0 to 5. When multiple $R^{20}$ groups are present, they may be the same or different.]

The definitions and examples of unsubstituted or substituted alkyl group, unsubstituted or substituted alkoxy group, unsubstituted or substituted aryl group, unsubstituted or substituted aryloxy group, unsubstituted or substituted monovalent heterocyclic, unsubstituted or substituted silyl group, halogen atom and alkoxycarbonyl groups represented by $R^{14}$, $R^{15}$, $R^{16}$, $R^{17}$, $R^{18}$ and $R^{19}$ in formula (12) are the same as the definitions and examples of unsubstituted or substituted alkyl group, unsubstituted or substituted alkoxy group, unsubstituted or substituted aryl group, unsubstituted or substituted aryloxy group, unsubstituted or substituted monovalent heterocyclic group, unsubstituted or substituted silyl group, halogen atom and alkoxycarbonyl groups represented by $R^3$ and $R^4$, respectively.

Constitutional units represented by formula (12) include constitutional units represented by the following formulas (12A-1) to (12A-8).

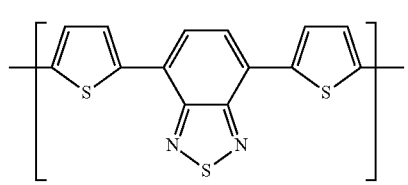

(12A-1)

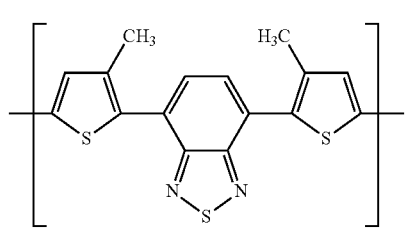

(12A-2)

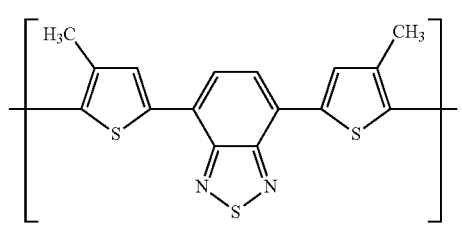

(12A-3)

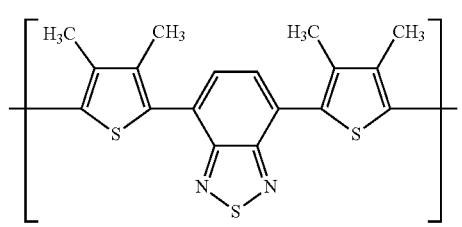

(12A-4)

-continued

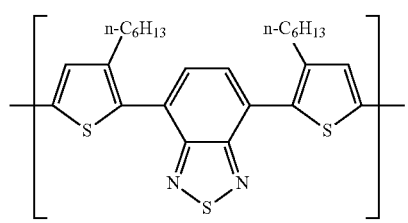
(12A-5)

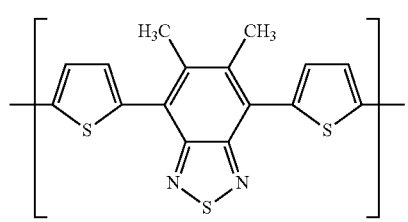
(12A-6)

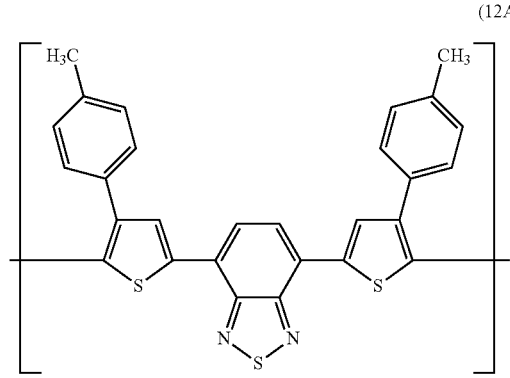
(12A-7)

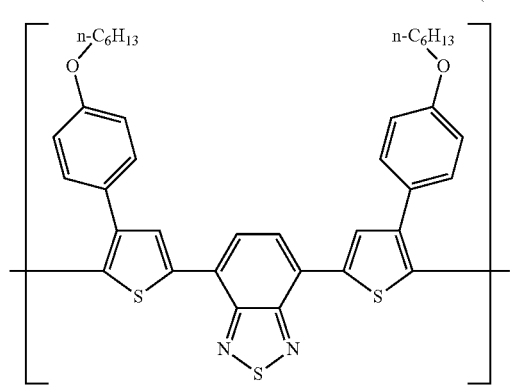
(12A-8)

The definitions and examples of unsubstituted or substituted alkyl group, unsubstituted or substituted alkoxy group, unsubstituted or substituted aryl group, unsubstituted or substituted aryloxy group, unsubstituted or substituted monovalent heterocyclic group, unsubstituted or substituted silyl group, halogen atom and alkoxycarbonyl groups represented by $R^{20}$ in formula (13) are the same as the definitions and examples of unsubstituted or substituted alkyl group, unsubstituted or substituted alkoxy group, unsubstituted or substituted aryl group, unsubstituted or substituted aryloxy group, unsubstituted or substituted monovalent heterocyclic group, unsubstituted or substituted silyl group, halogen atom and alkoxycarbonyl groups represented by $R^3$ and $R^4$, respectively.

In formula (13), g represents an integer of 0 to 5, preferably an integer of 1 to 3, and more preferably 1.

Constitutional units represented by formula (13) include constitutional units represented by the following formulas (13A-1) to (13A-6).

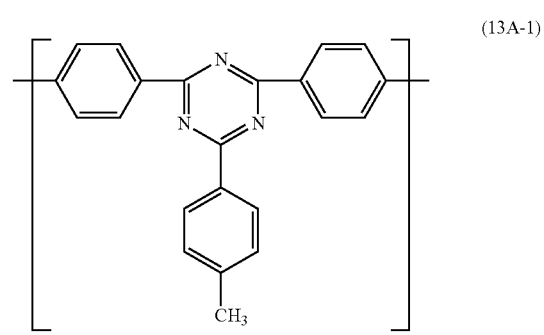
(13A-1)

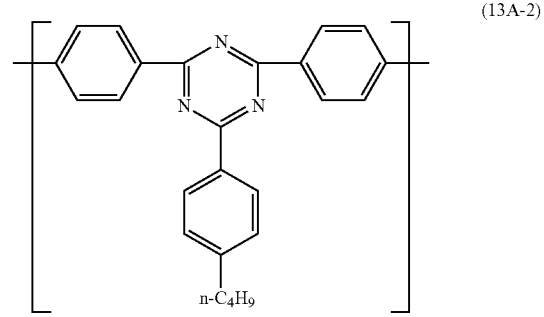
(13A-2)

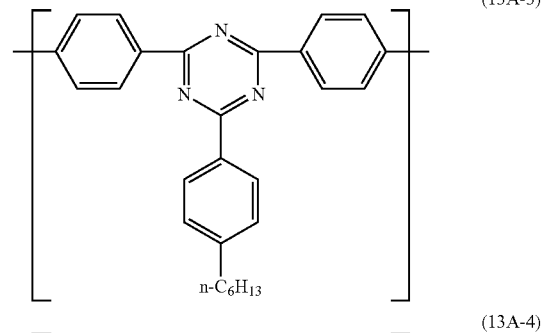
(13A-3)

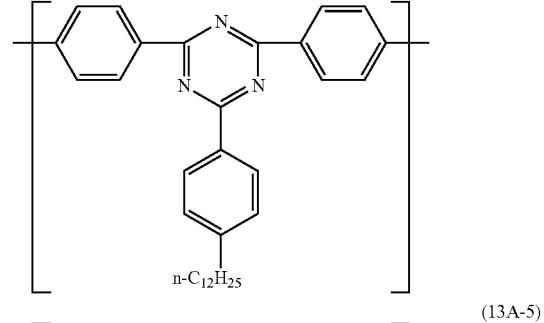
(13A-4)

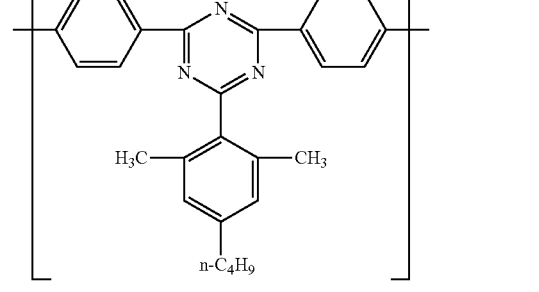
(13A-5)

-continued

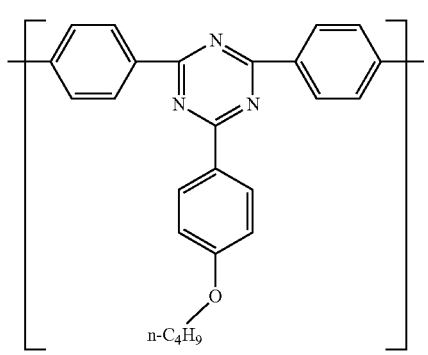
(13A-6)

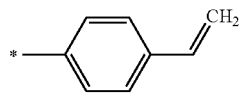
(15A-1)

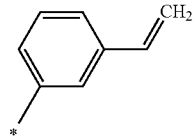
(15A-2)

In order to facilitate formation of a multilayer structure of the light-emitting device, the polymer compound of this embodiment preferably further contains at least one constitutional unit selected from the group consisting of a constitutional unit represented by formula (15) and a constitutional units represented by formula (16), in addition to a constitutional unit represented by formula (1).

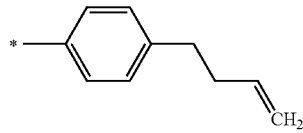
(15A-3)

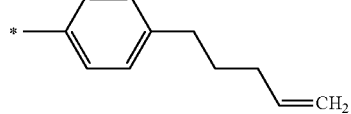
(15A-4)

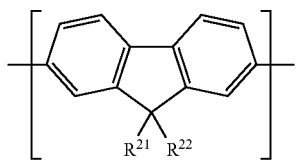
(15)

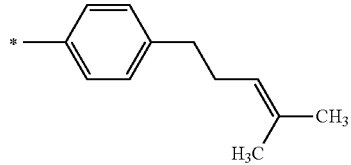
(15A-5)

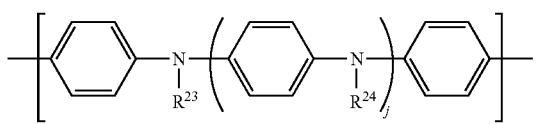
(16)

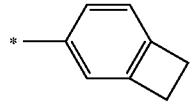
(15A-6)

[In formula (15), $R^{21}$ represents a crosslinkable group. $R^{22}$ represents hydrogen atom, a crosslinkable group, unsubstituted or substituted alkyl group or unsubstituted or substituted aryl group. This is with the proviso that the constitutional unit represented by formula (15) is a constitutional unit having a different structure from the constitutional unit represented by formula (1), the constitutional unit represented by formula (6) and the constitutional unit represented by formula (9).

In formula (16), $R^{23}$ represents a crosslinkable group. $R^{24}$ represents a crosslinkable group, unsubstituted or substituted alkyl group or unsubstituted or substituted aryl group. The letter j represents 0 or 1. This is with the proviso that the constitutional unit represented by formula (16) is a constitutional unit having a different structure from the constitutional unit represented by formula (7) and the constitutional unit represented by formula (14).]

In formula (15), $R^{21}$ represents a crosslinkable group. A crosslinkable group is a group represented by any of the following formulas (15A-1) to (15A-27). In order to increase the luminance life of the element to be obtained, it is preferably a group represented by any of formulas (15A-3) to (15A-15), and more preferably a group represented by any of formulas (15A-6) to (15A-9) or formulas (15A-12) to (15A-14). The "*" symbol in the following formulas represents a bonding site.

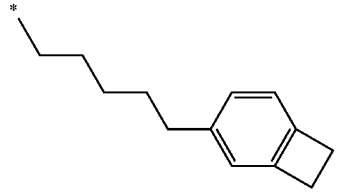
(15A-7)

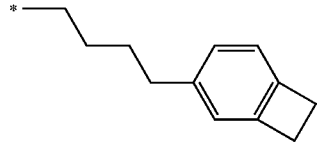
(15A-8)

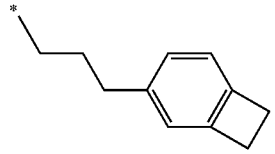
(15A-9)

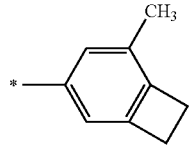
(15A-10)

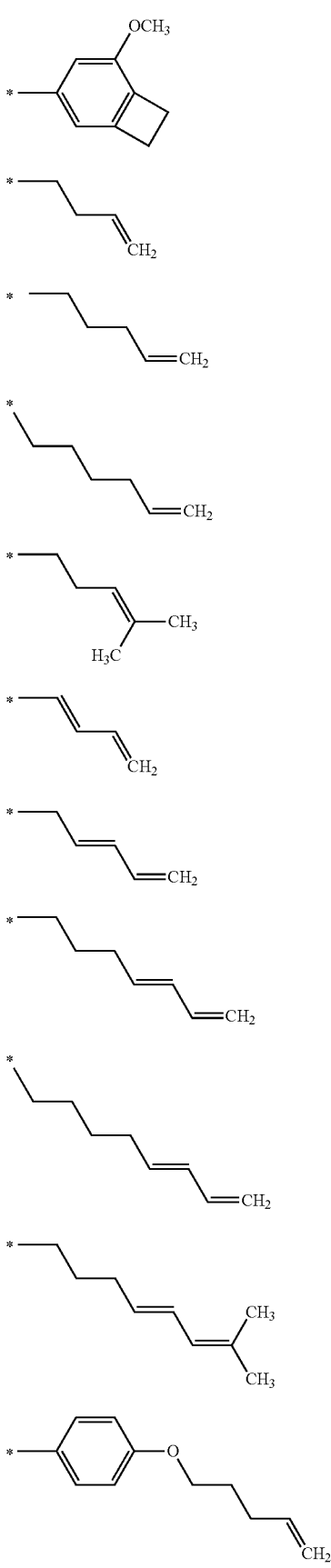

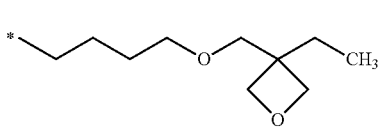
(15A-22)

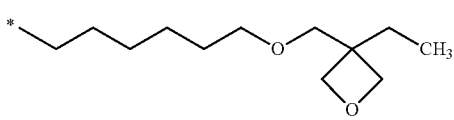
(15A-23)

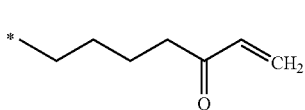
(15A-24)

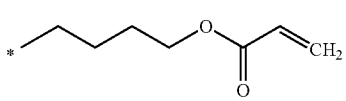
(15A-25)

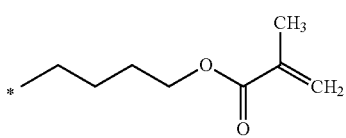
(15A-26)

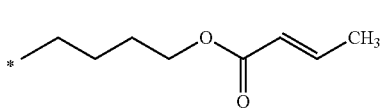
(15A-27)

$R^{22}$ in formula (15) represents a crosslinkable group, hydrogen atom, unsubstituted or substituted alkyl group or unsubstituted or substituted aryl group. $R^{22}$ preferably represents a crosslinkable group or an unsubstituted or substituted aryl group, and more preferably a crosslinkable group.

The definitions and examples of crosslinkable groups represented by $R^{22}$ are the same as the definitions and examples of crosslinkable groups represented by $R^{21}$.

The definitions and examples of unsubstituted or substituted alkyl or unsubstituted or substituted aryl groups represented by $R^{22}$ are the same as the definitions and examples of unsubstituted or substituted alkyl group or unsubstituted or substituted aryl groups represented by $R^3$ and $R^4$, respectively. This is with the proviso that an unsubstituted or substituted alkyl group or unsubstituted or substituted aryl group represented by $R^{22}$ is a group with a different structure than the crosslinkable group represented by $R^{21}$.

Constitutional units represented by formula (15) include constitutional units represented by the following formulas (15B-1) to (15B-8). In order to further lengthen the luminance life of the element to be obtained, there are preferred constitutional units represented by formulas (15B-2) to (15B-8), more preferably constitutional units represented by formula (15B-2) and formulas (15B-4) to (15B-6), and even more preferably constitutional units represented by formula (15B-2), formula (15B-5) or formula (15B-6).

(15B-1) 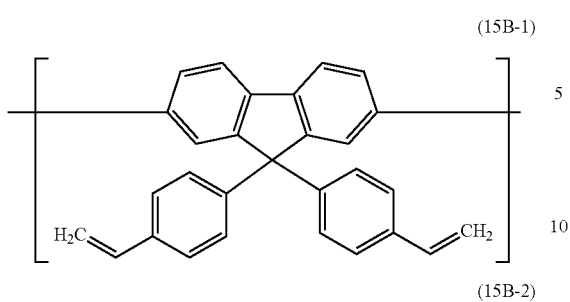

(15B-2) 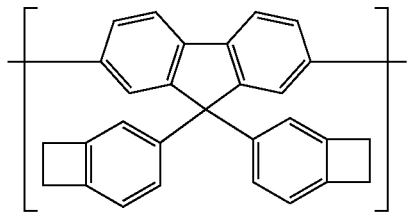

(15B-3) 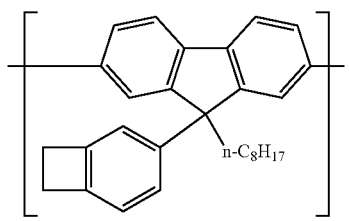

(15B-4) 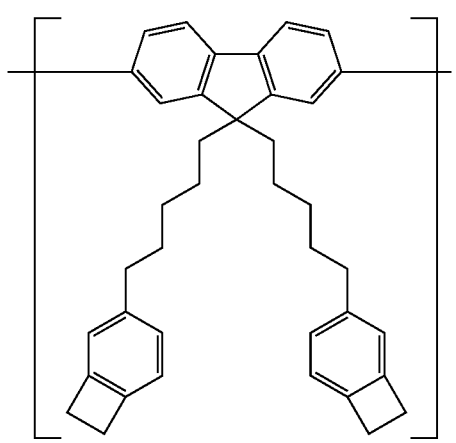

(15B-5) 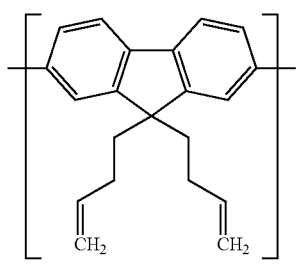

(15B-6) 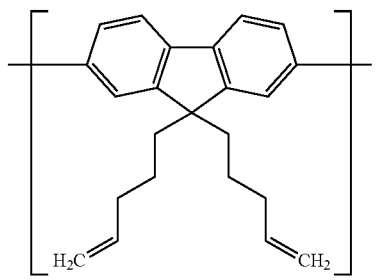

(15B-7) 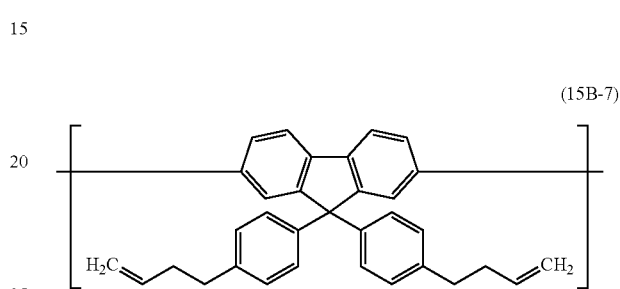

(15B-8) 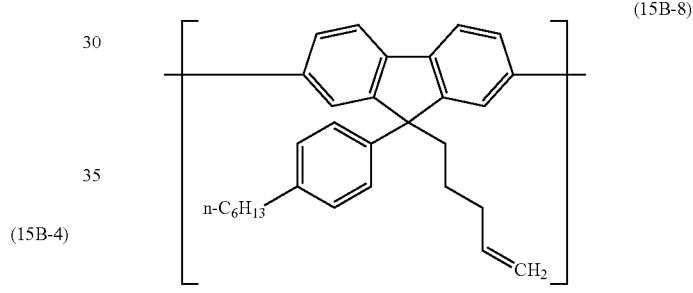

In formula (16), $R^{23}$ represents a crosslinkable group. The definitions and examples of crosslinkable groups represented by $R^{23}$ are the same as the definitions and examples of crosslinkable groups represented by $R^{21}$.

$R^{24}$ in formula (16) represents a crosslinkable group, unsubstituted or substituted alkyl group or unsubstituted or substituted aryl group, and preferably a crosslinkable group.

The definitions and examples of crosslinkable groups represented by $R^{24}$ are the same as the definitions and examples of crosslinkable groups represented by $R^{21}$.

The definitions and examples of unsubstituted or substituted alkyl group or unsubstituted or substituted aryl groups represented by $R^{24}$ are the same as the definitions and examples of unsubstituted or substituted alkyl group or unsubstituted or substituted aryl groups represented by $R^{3}$ and $R^{4}$, respectively.

In formula (16), j represents 0 or 1, and preferably 0.

Constitutional units represented by formula (16) include constitutional units represented by the following formulas (16A-1) to (16A-4). In order to further lengthen the luminance life of the obtained light-emitting device, a constitutional unit represented by formula (16A-2) or formula (16A-4) is preferred, and a constitutional unit represented by formula (16A-2) is more preferred.

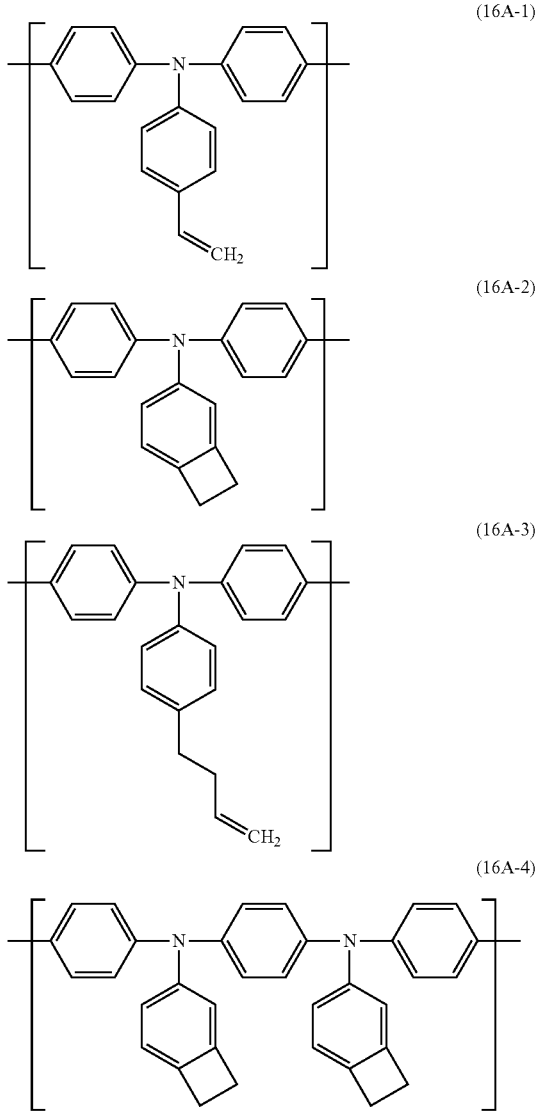

As explained above, the polymer compound of the invention is preferably a polymer compound comprising a constitutional unit represented by formula (1), and at least one constitutional unit selected from the group consisting of constitutional units represented by formula (6) and constitutional units represented by formula (7) (hereunder referred to as "polymer compound A").

As a first embodiment of polymer compound A there are preferred:

a polymer compound comprising a constitutional unit represented by formula (1) and at least one constitutional unit selected from the group consisting of constitutional units represented by formula (6) and constitutional units represented by formula (7) (hereunder referred to as "polymer compound B"), and a polymer compound comprising a constitutional unit represented by formula (1) and at least one constitutional unit selected from the group consisting of constitutional units represented by formula (8), constitutional units represented by formula (9), constitutional units represented by formula (10) and constitutional units represented by formula (14) (hereunder referred to as "polymer compound C").

As an embodiment of polymer compound C, there is preferred a polymer compound comprising a constitutional unit represented by formula (1) and at least one constitutional unit selected from the group consisting of constitutional units represented by formula (8), constitutional units represented by formula (9), constitutional units represented by formula (10) and constitutional units represented by formula (14) (hereunder referred to as "polymer compound D"), and there is more preferred a polymer compound comprising a constitutional unit represented by formula (1) and at least one constitutional unit selected from the group consisting of constitutional units represented by formula (9), constitutional units represented by formula (10) and constitutional units represented by formula (14) (hereunder referred to as "polymer compound E").

As a second embodiment of polymer compound A, there is preferred a polymer compound comprising a constitutional unit represented by formula (1), at least one constitutional unit selected from the group consisting of constitutional units represented by formula (12) and constitutional units represented by formula (13), and at least one constitutional unit selected from the group consisting of constitutional units represented by formula (8), constitutional units represented by formula (9), constitutional units represented by formula (10) and constitutional units represented by formula (14) (hereunder referred to as "polymer compound F"), and there is more preferred a polymer compound comprising a constitutional unit represented by formula (1), at least one constitutional unit selected from the group consisting of constitutional units represented by formula (12) and constitutional units represented by formula (13), and at least one constitutional unit selected from the group consisting of constitutional units represented by formula (8), constitutional units represented by formula (9), constitutional units represented by formula (10) and constitutional units represented by formula (14) (hereunder referred to as "polymer compound G").

As a third embodiment of polymer compound A there are preferred:

a polymer compound comprising a constitutional unit represented by formula (1) and at least one constitutional unit selected from the group consisting of constitutional units represented by formula (9), constitutional units represented by formula (12) and constitutional units represented by formula (14) (hereunder referred to as "polymer compound H"), and a polymer compound comprising a constitutional unit represented by formula (1) and at least one constitutional unit selected from the group consisting of constitutional units represented by formula (8), constitutional units represented by formula (9) and constitutional units represented by formula (13) (hereunder referred to as "polymer compound I").

As an embodiment of polymer compound I there is preferred a polymer compound comprising a constitutional unit represented by formula (1), and at least one constitutional unit selected from the group consisting of constitutional units represented by formula (8), constitutional units represented by formula (9) and constitutional units represented by formula (13) (hereunder referred to as "polymer compound J").

As a fourth embodiment of polymer compound A there is preferred:

a polymer compound comprising a constitutional unit represented by formula (1), at least one constitutional unit selected from the group consisting of constitutional units represented by formula (6) and constitutional units represented by formula (7), and at least one constitutional unit selected from the group consisting of constitutional units represented by formula (15) and constitutional units represented by formula (16) (hereunder referred to as "polymer compound K").

As an embodiment of polymer compound K, there is preferred a polymer compound comprising a constitutional unit represented by formula (1), at least one constitutional unit selected from the group consisting of constitutional units represented by formula (8), constitutional units represented by formula (9), constitutional units represented by formula (10) and constitutional units represented by formula (14), and at least one constitutional unit selected from the group consisting of constitutional units represented by formula (15) and constitutional units represented by formula (16) (hereunder referred to as "polymer compound L"), and there is more preferred a polymer compound comprising a constitutional unit represented by formula (1), a constitutional unit represented by formula (9) and a constitutional unit represented by formula (14), and at least one constitutional unit selected from the group consisting of constitutional units represented by formula (15) and constitutional units represented by formula (16) (hereunder referred to as "polymer compound M").

The proportion of the total number of moles of constitutional units represented by formula (1), constitutional units represented by formula (6) and constitutional units represented by formula (7) with respect to the total number of moles of all of the constitutional units in polymer compound A is preferably 80-100%, more preferably 90-100% and even more preferably 95-100%. The case where this proportion is 100% corresponds to polymer compound B.

In polymer compounds A and B, the total of the constitutional unit represented by formula (6) and the constitutional unit represented by formula (7) is preferably 1-700 parts by mole, more preferably 5-200 parts by mole and especially 15-200 parts by mole, where the constitutional unit represented by formula (1) is defined as 100 parts by mole.

In polymer compound C, the proportion of the total number of moles of the constitutional unit represented by formula (1), the constitutional unit represented by formula (8), the constitutional unit represented by formula (9), the constitutional unit represented by formula (10) and the constitutional unit represented by formula (14) is preferably 80-100%, more preferably 90-100% and particularly preferably 95-100%, with respect to the total number of moles of all of the constitutional units. The case where this proportion is 100% corresponds to polymer compound D or E.

In polymer compounds C and D, the total of the constitutional unit represented by formula (8), the constitutional unit represented by formula (9), the constitutional unit represented by formula (10) and the constitutional unit represented by formula (14) is preferably 1-700 parts by mole, more preferably 5-200 parts by mole and especially 15-200 parts by mole, where the constitutional unit represented by formula (1) is defined as 100 parts by mole.

In polymer compound E, the total of the constitutional unit represented by formula (9), the constitutional unit represented by formula (10) and the constitutional unit represented by formula (14) is preferably 1-700 parts by mole, more preferably 5-200 parts by mole and especially 15-200 parts by mole, where the constitutional unit represented by formula (1) is defined as 100 parts by mole.

In polymer compound F, the proportion of the total moles of the constitutional unit represented by formula (1), the constitutional unit represented by formula (12), the constitutional unit represented by formula (13), the constitutional unit represented by formula (8), the constitutional unit represented by formula (9), the constitutional unit represented by formula (10) and the constitutional unit represented by formula (14) is preferably 80-100%, more preferably 90-100% and particularly preferably 95-100%, with respect to the total number of moles of all of the constitutional units. The case where this proportion is 100% corresponds to polymer compound G.

In polymer compounds F and G, the total of the constitutional unit represented by formula (12) and the constitutional unit represented by formula (13) is preferably 0.1-100 parts by mole, more preferably 1-50 parts by mole and especially 5-30 parts by mole, where the constitutional unit represented by formula (1) is defined as 100 parts by mole. Also, the total of the constitutional unit represented by formula (8), the constitutional unit represented by formula (9), the constitutional unit represented by formula (10) and the constitutional unit represented by formula (14) is preferably 1-700 parts by mole, more preferably 5-200 parts by mole and particularly preferably 15-200 parts by mole.

In polymer compound H, the proportion of the total number of moles of the constitutional unit represented by formula (1), the constitutional unit represented by formula (9), the constitutional unit represented by formula (12) and the constitutional unit represented by formula (14) is preferably 80-100%, more preferably 90-100% and even more preferably 95-100%, with respect to the total number of moles of all of the constitutional units.

In polymer compound H, the total of the constitutional unit represented by formula (9), the constitutional unit represented by formula (12) and the constitutional unit represented by formula (13) is preferably 0.1-200 parts by mole, more preferably 1-100 parts by mole and particularly preferably 5-50 parts by mole, where the constitutional unit represented by formula (1) is defined as 100 parts by mole.

In polymer compound I, the proportion of the total number of moles of the constitutional unit represented by formula (1), the constitutional unit represented by formula (8), the constitutional unit represented by formula (9) and the constitutional unit represented by formula (13) is preferably 80-100%, more preferably 90-100% and even more preferably 95-100%, with respect to the total number of moles of all of the constitutional units. The case where this proportion is 100% corresponds to polymer compound J.

In polymer compounds I and J, the total of the constitutional unit represented by formula (8), the constitutional unit represented by formula (9) and the constitutional unit represented by formula (13) is preferably 50-1000 parts by mole, more preferably 75-500 parts by mole and particularly preferably 100-300 parts by mole, where the constitutional unit represented by formula (1) is defined as 100 parts by mole.

In polymer compound K, the proportion of the total number of moles of the constitutional unit represented by formula (1), the constitutional unit represented by formula (6), the constitutional unit represented by formula (7), the constitutional unit represented by formula (15) and the constitutional unit represented by formula (16) is preferably 80-100%, more preferably 90-100% and particularly preferably 95-100%, with respect to the total number of moles of all of the constitutional units.

In polymer compound K, the total of the constitutional unit represented by formula (6) and the constitutional unit represented by formula (7) is preferably 1-300 parts by mole, more preferably 30-200 parts by mole and especially 50-150 parts by mole, where the constitutional unit represented by formula (1) is defined as 100 parts by mole. Also, the total of the constitutional unit represented by formula (15) and the constitutional unit represented by formula (16) is preferably 1-100 parts by mole, more preferably 3-50 parts by mole and particularly preferably 5-30 parts by mole.

In polymer compound L, the proportion of the total number of moles of the constitutional unit represented by formula (1), the constitutional unit represented by formula (8), the constitutional unit represented by formula (9), the constitutional unit represented by formula (10), the constitutional unit represented by formula (14), the constitutional unit represented by formula (15) and the constitutional unit represented by formula (16) is preferably 80-100%, more preferably 90-100% and particularly preferably 95-100%, with respect to the total number of moles of all of the constitutional units.

In polymer compound L, the total of the constitutional unit represented by formula (8), the constitutional unit represented by formula (9), the constitutional unit represented by formula (10) and the constitutional unit represented by formula (14) is preferably 1-300 parts by mole, more preferably 30-200 parts by mole and particularly preferably 50-150 parts by mole, and the total of the constitutional unit represented by formula (15) and the constitutional unit represented by formula (16) is preferably 1-100 parts by mole, more preferably 3-50 parts by mole and particularly preferably 5-30 parts by mole, where the constitutional unit represented by formula (1) is defined as 100 parts by mole.

In polymer compound M, the proportion of the total number of moles of the constitutional unit represented by formula (1), the constitutional unit represented by formula (9), the constitutional unit represented by formula (14), the constitutional unit represented by formula (15) and the constitutional unit represented by formula (16) is preferably 80-100%, more preferably 90-100% and particularly preferably 95-100%, with respect to the total number of moles of all of the constitutional units.

In polymer compound M, the total of the constitutional unit represented by formula (9) and the constitutional unit represented by formula (14) is preferably 1-300 parts by mole, more preferably 30-200 parts by mole and particularly preferably 50-150 parts by mole, and the total of the constitutional unit represented by formula (15) and the constitutional unit represented by formula (16) is preferably 1-100 parts by mole, more preferably 3-50 parts by mole and particularly preferably 5-30 parts by mole, where the constitutional unit represented by formula (1) is defined as 100 parts by mole.

The polystyrene-equivalent number-average molecular weight (Mn) of the polymer compound of this embodiment, as measured by gel permeation chromatography (hereinafter referred to as "GPC") will usually be $1\times10^3$ to $1\times10^8$ and is preferably $1\times10^4$ to $1\times10^6$. The polystyrene-equivalent weight-average molecular weight (Mw) of the polymer compound of this embodiment will usually be $1\times10^3$ to $1\times10^8$, and for satisfactory film formability, it is preferably $1\times10^4$ to $5\times10^6$, more preferably $3\times10^4$ to $1\times10^6$ and even more preferably $5\times10^4$ to $5\times10^5$.

If the end groups of the polymer compound of this embodiment remain as polymerizing active groups, the luminescence property and usable life may potentially be reduced when the polymer compound is used to fabricate a light-emitting device, and therefore stable groups are preferred. The end groups are preferably groups that have conjugated bonds with the main chain, and these include groups bonded to aryl group or monovalent heterocyclic group via carbon-carbon bonds (specifically, the substituents shown in formula 10 of Japanese Unexamined Patent Application Publication HEI No. 9-45478).

The polymer compound of this embodiment may be a block copolymer, random copolymer, alternating copolymer or graft copolymer, or it may be in another form.

The following polymer compounds (P-1) to (P-14) may be mentioned as preferred polymer compounds. For example, polymer compound (P-1) is a copolymer comprising 2 different constitutional units in the molar ratio Q1:Q2, and polymer compounds (P-2) to (P-14) are likewise. Here, $R^{1A}$, $R^{1B}$, $R^{2A}$, $R^{2B}$, $R^9$, $R^{10}$, $R^{11}$, $R^{12}$, $R^{13}$, $R^{13t}$, $R^{20}$, $R^{21}$, $R^{22}$, $R^{23}$, $R^{24}$, $R^D$, $R^E$, $Ar^4$, e, f, g, h, i and j have the same meanings as above. Also, Q1 to Q42 are numbers (molar ratios) satisfying the relational formula for the chemical formulas representing each of the compounds. The molecular weights of polymer compounds (P-1) to (P-14) are the same as explained above for the polymer compound molecular weights.

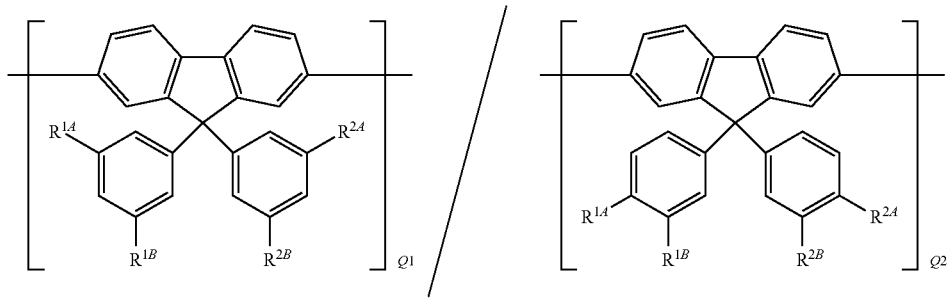

Polymer compound (P-1)

$(5 \leq Q1 \leq 95, 5 \leq Q2 \leq 95, Q1 + Q2 = 100)$

Polymer compound (P-2)
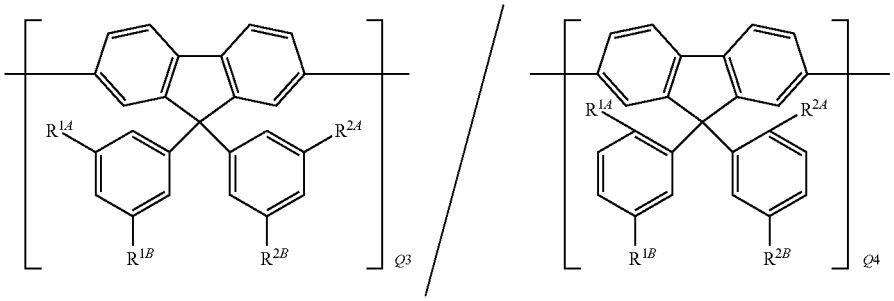
(5 ≤ Q3 ≤ 95, 5 ≤ Q4 ≤ 95, Q3 + Q4 = 100)
Polymer compound (P-3)
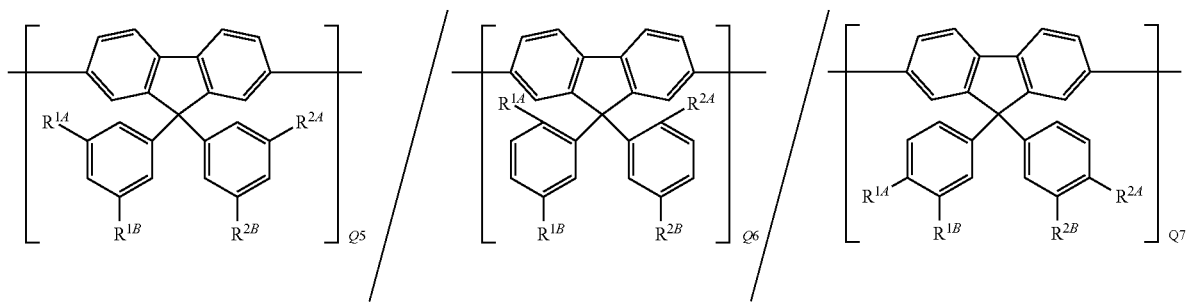
(5 ≤ Q5 ≤ 90, 5 ≤ Q6 ≤ 90, 5 ≤ Q7 ≤ 90, Q5 + Q6 + Q7 = 100)
Polymer compound (P-4)
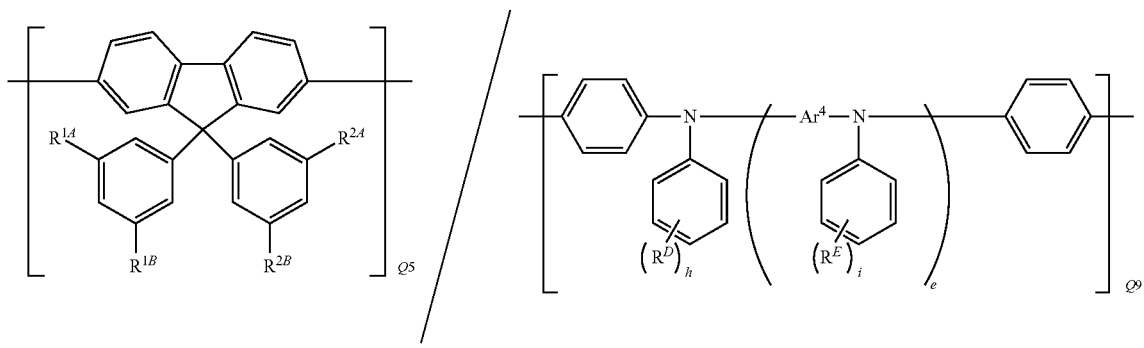
(50 ≤ Q8 ≤ 95, 5 ≤ Q9 ≤ 50, Q8 + Q9 = 100)
Polymer compound (P-5)
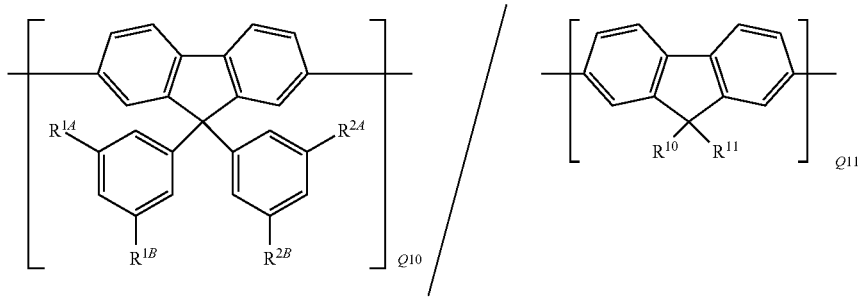
(5 ≤ Q10 ≤ 95, 5 ≤ Q11 ≤ 95, Q10 + Q11 = 100)

Polymer compound (P-6)
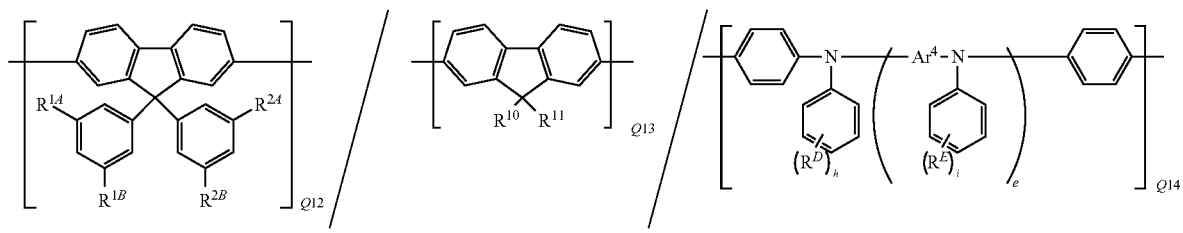
$(5 \leq Q11 \leq 94, 5 \leq Q13 \leq 94, 1 \leq Q14 \leq 50, Q12 + Q13 + Q14 = 100)$
Polymer compound (P-7)
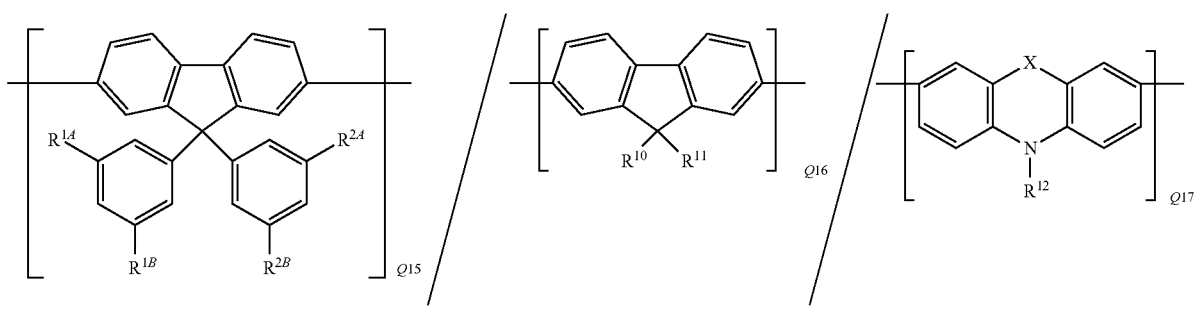
$(5 \leq Q15 \leq 94, 5 \leq Q16 \leq 94, 1 \leq Q17 \leq 50, Q15 + Q16 + Q17 = 100)$
Polymer compound (P-8)
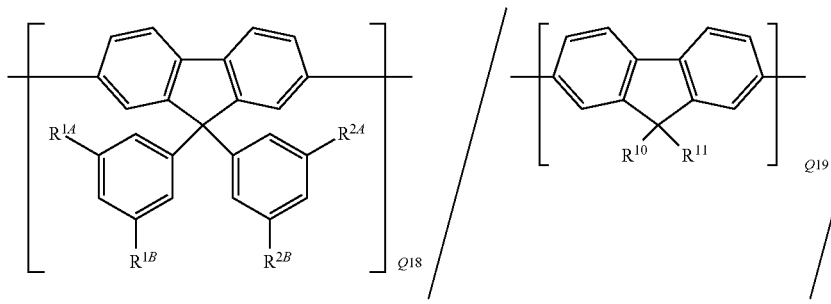
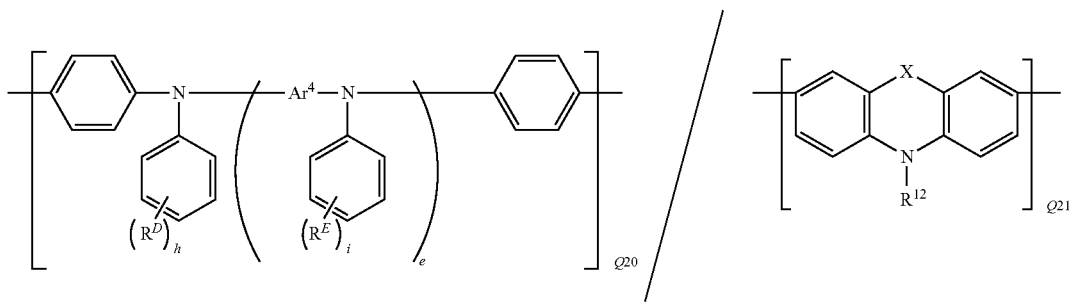
$(5 \leq Q18 \leq 93, 5 \leq Q19 \leq 93, 1 \leq Q20 \leq 30, 1 \leq Q21 \leq 30, Q18 + Q19 + Q20 + Q21 = 100)$ Polymer compound (P-9)
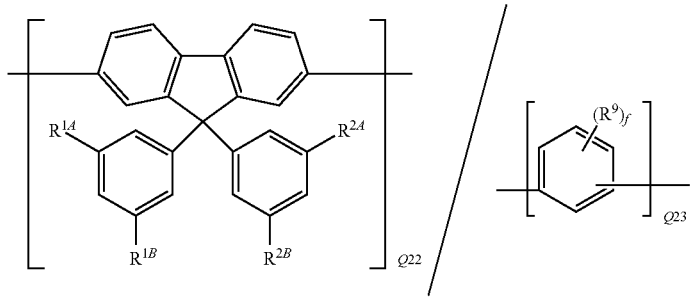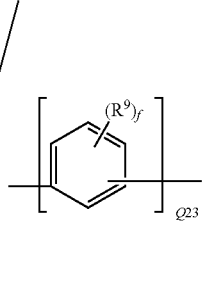
(5 ≤ Q22 ≤ 95, 5 ≤ Q23 ≤ 95, Q22 + Q23 = 100)
Polymer compound (P-10)
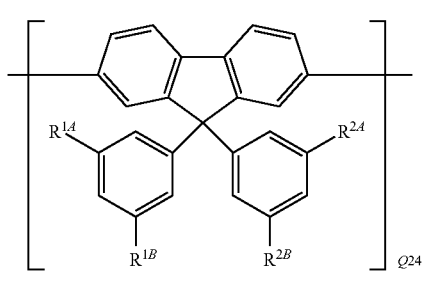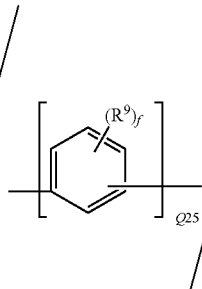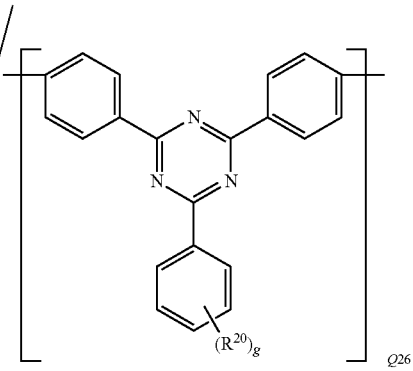
(5 ≤ Q24 ≤ 94, 5 ≤ Q25 ≤ 94, 1 ≤ Q26 ≤ 30, Q24 + Q25 + Q26 = 100)
Polymer compound (P-11)
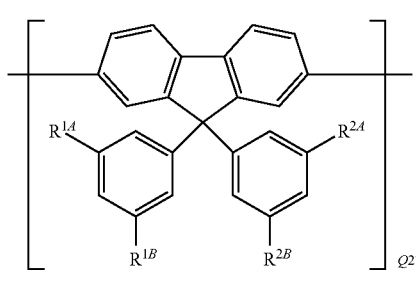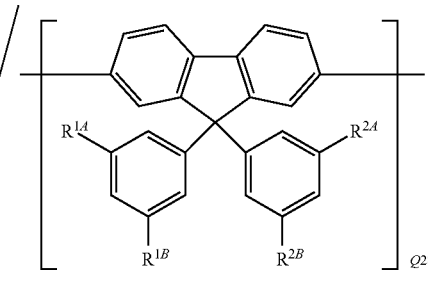
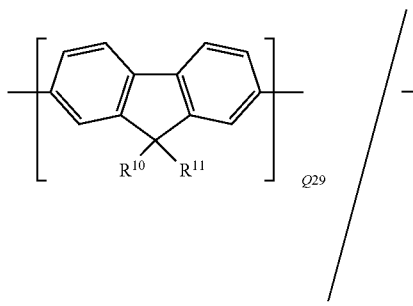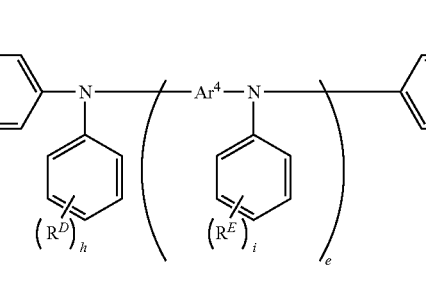
(5 ≤ Q27 ≤ 89, 5 ≤ Q28 ≤ 89, 5 ≤ Q29 ≤ 89, 1 ≤ Q30 ≤ 30, Q27 + Q28 + Q29 + Q30 = 100)

-continued
Polymer compound (P-12)
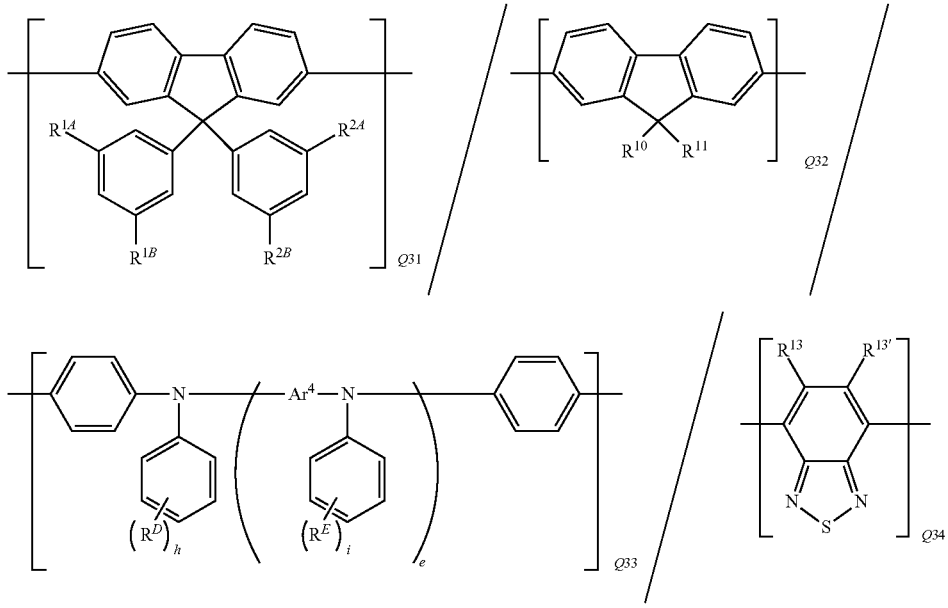
$(5 \leq Q31 \leq 93, 5 \leq Q32 \leq 93, 1 \leq Q33 \leq 30, 1 \leq Q34 \leq 50, Q31 + Q32 + Q33 + Q34 = 100)$
Polymer compound (P-13)
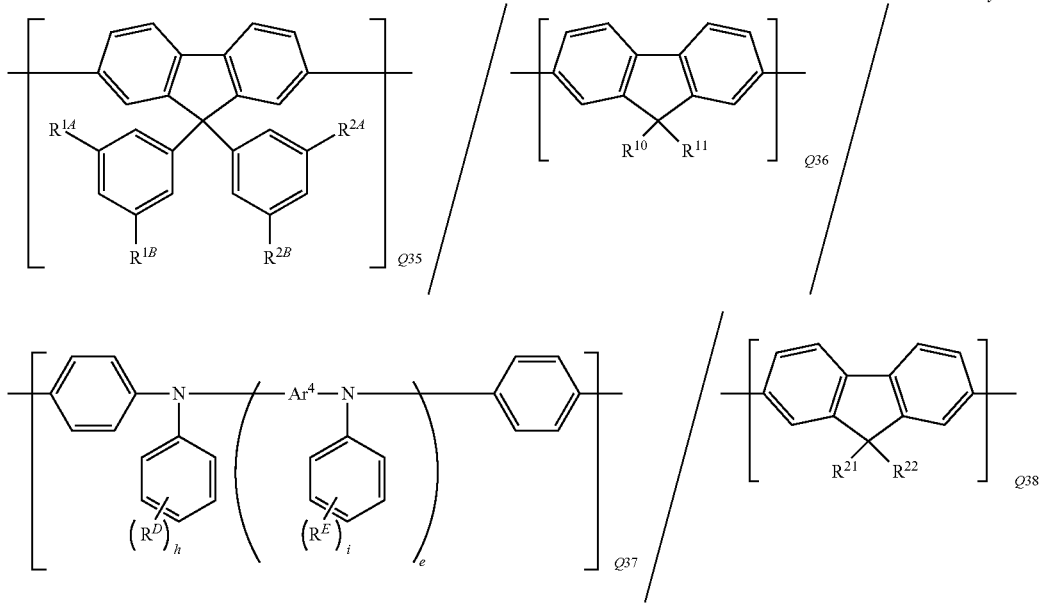
$(5 \leq Q35 \leq 89, 5 \leq Q36 \leq 89, 5 \leq Q37 \leq 89, 1 \leq Q38 \leq 30, Q35 + Q36 + Q37 + Q38 = 100)$
Polymer compound (P-14)
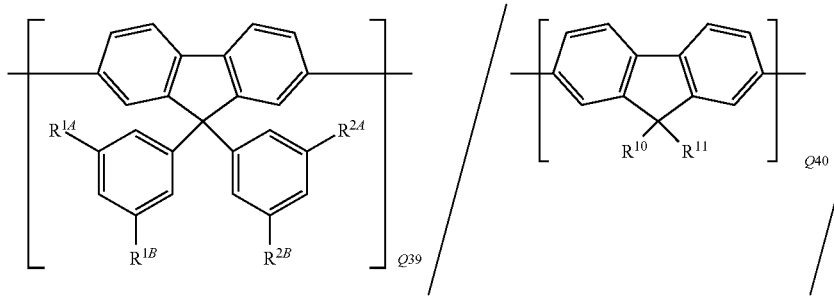

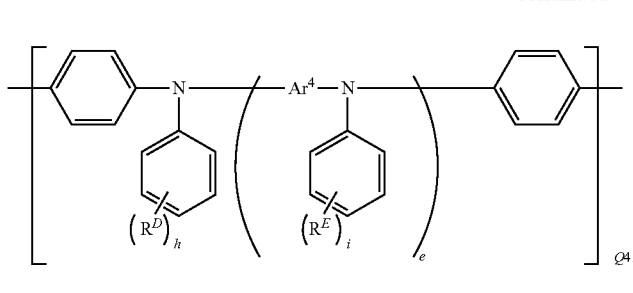

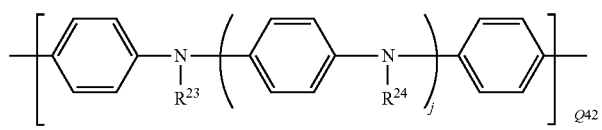

$(5 \leq Q39 \leq 89, 5 \leq Q40 \leq 89, 5 \leq Q41 \leq 89, 1 \leq Q42 \leq 30, Q39 + Q40 + Q41 + Q42 = 100)$

[Method for Producing Polymer Compound]

A preferred method for producing the polymer compound will now be described.

A preferred embodiment of the polymer compound may be produced, for example, by condensation polymerization of a compound represented by formula (a).

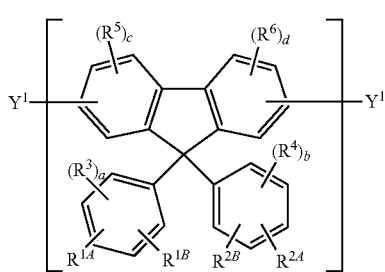

(a)

—O—S(=O)(=O)—$R^T$ (a-1)

—MgX$_A$ (a-2)

—ZnX$_A$ (a-3)

—Sn($R^T$)$_3$ (a-4)

[In formula (a), $R^{1A}$, $R^{1B}$, $R^{2A}$, $R^{2B}$, $R^3$, $R^4$, $R^5$, $R^6$, a, b, c and d have the same meanings specified above. $Y^1$ is a halogen atom, methoxy group, boric acid ester residue group, boric acid residue group (i.e. —B(OH)$_2$), a group represented by formula (a-1), a group represented by formula (a-2), a group represented by formula (a-3) or a group represented by formula (a-4). Two $Y^1$ groups when present may be the same or different. In formulas (a-1) and (a-4), $R^T$ represents unsubstituted or substituted alkyl group or unsubstituted or substituted aryl group. Multiple $R^T$ groups in formula (a-4) may be the same or different. In formulas (a-2) and (a-3), $X_A$ represents a halogen atom.]

When the polymer compound comprises a constitutional unit represented by formula (6) and a constitutional unit represented by formula (7), such a polymer compound can be obtained, for example, by condensation polymerization of a compound represented by formula (a), and at least one compound selected from the group consisting of compounds represented by formula (b-1) and compounds represented by formula (b-2).

$Y^1$—(Ar$^1$)—$Y^1$ (b-1)

(b-2)

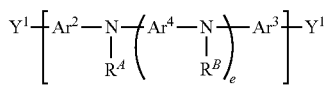

[In formulas (b-1) and (b-2), Ar$^1$, Ar$^2$, Ar$^3$, Ar$^4$, $R^A$, $R^B$, $Y^1$ and e have the same meanings as above.]

In formulas (a), (b-1), (b-2), (a-2) and (a-3), the halogen atoms represented by $Y^1$ and $X_A$ may be chlorine atom, bromine atom or iodine atom.

In formulas (a), (b-1) and (b-2), the boric acid ester residue group represented by $Y^1$ may be a group represented by the following formula.

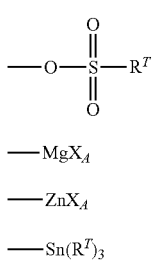

In formula (a-1), the definitions and examples of unsubstituted alkyl groups represented by $R^T$ are the same as the definitions and examples of unsubstituted alkyl groups represented by $R^3$ and $R^4$. Also, the definitions and examples of substituted alkyl groups are the same as the definitions and examples of substituted alkyl groups represented by $R^3$ and $R^4$.

In formula (a-1), the definitions and examples of unsubstituted or substituted aryl groups are the same as the definitions and examples of unsubstituted or substituted aryl groups represented by $R^3$ and $R^4$, respectively.

Sulfonate groups represented by formula (a-1) include methane sulfonate group, trifluoromethane sulfonate group, phenyl sulfonate group and 4-methylphenyl sulfonate group.

In formula (a-4), the definitions and examples of unsubstituted or substituted alkyl group and unsubstituted or substituted aryl groups represented by $R^T$ are the same as the definitions and examples of unsubstituted or substituted alkyl group and unsubstituted or substituted aryl groups represented by $R^3$ and $R^4$.

Groups represented by formula (a-4) include trimethylstannanyl group, triethylstannanyl group and tributylstannanyl group.

The compounds represented by formulas (a), (b-1) and (b-2) may be synthesized and isolated beforehand, or they may be prepared in the reaction system and used directly.

In formulas (a), (b-1) and (b-2), $Y^1$ is preferably a halogen atom, boric acid ester residue group or boric acid residue group in order to improve convenience of synthesis and ease of handling of the compound represented by formula (a), (b-1) or (b-2).

The method of condensation polymerization may be a method of reacting a compound represented by formula (a), (b-1) or (b-2), using an appropriate catalyst and an appropriate base.

Such catalysts include transition metal complexes which may be palladium complexes such as palladium [tetrakis (triphenylphosphine)], [tris(dibenzylideneacetone)]dipalladium and palladium acetate or nickel complexes such as nickel [tetrakis(triphenylphosphine)], [1,3-bis(diphenylphosphino)propane]dichloronickel and [bis(1,4-cyclooctadiene)]nickel, or catalysts further comprising ligands such as triphenylphosphine, tri(tert-butylphosphine), tricyclohexylphosphine, diphenylphosphinopropane or bipyridyl as necessary. The catalyst may be synthesized beforehand or prepared in the reaction system and used directly. These catalysts may be used alone or in combinations of two or more.

When a catalyst is used, the amount of use is preferably 0.00001-3 mol equivalents, more preferably 0.00005-0.5 mol equivalents and even more preferably 0.0001-0.2 mol equivalents, as the amount of transition metal compound with respect to the total number of moles of the compound represented by formula (a), (b-1) or (b-2).

Examples of bases include inorganic bases such as sodium carbonate, potassium carbonate, cesium carbonate, potassium fluoride, cesium fluoride and tripotassium phosphate, and organic bases such as tetrabutylammonium fluoride, tetrabutylammonium chloride, tetrabutylammonium bromide and tetrabutylammonium hydroxide. These bases may be used alone or in combinations of two or more.

When a base is used, the amount of use is preferably 0.5-20 mol equivalents and more preferably 1-10 mol equivalents with respect to the total number of moles of the compound represented by formula (a), (b-1) or (b-2).

The condensation polymerization may usually be conducted in the presence of a solvent such as an organic solvent.

The organic solvent will differ depending on the type of compound represented by formula (a), (b-1) or (b-2) and on the reaction, and examples include toluene, xylene, mesitylene, tetrahydrofuran, 1,4-dioxane, dimethoxyethane, N,N-dimethylacetamide and N,N-dimethylformamide. In order to inhibit secondary reactions, such solvents are preferably subjected to deoxidizing treatment. These organic solvents may be used alone or in combinations of two or more.

The amount of organic solvent used is such that the total concentration of the compound represented by formula (a), (b-1) or (b-2) is usually 0.1-90 wt %, preferably 1-50 wt % and more preferably 2-30 wt %.

The reaction temperature for the condensation polymerization is preferably −100° C. to 200° C., more preferably −80° C. to 150° C. and even more preferably 0° C. to 120° C. The reaction time will depend on the conditions such as the reaction temperature, but it will usually be at least 1 hour, and is preferably 2-500 hours.

The condensation polymerization is preferably conducted under anhydrous conditions when $Y^1$ in formula (a), (b-1) or (b-2) is a group represented by formula (a-2), for example.

The method of condensation polymerization may be a method of polymerization by Suzuki reaction (Chem. Rev. Vol. 95, p. 2457 (1995)), a method of polymerization by Grignard reaction (Kobunshi Kinou Zairyo Series Vol. 2, "Polymer Syntheses and Reactions (2), p. 432-433, Kyoritsu Publishing), or a method of polymerization by Yamamoto polymerization (Prog. Polym. Sci., Vol. 17, p. 1153-1205, 1992).

Post-treatment after condensation polymerization may be carried out by a known method, such as adding the reaction solution obtained by condensation polymerization to a lower alcohol such as methanol and filtering and drying the deposited precipitate.

Such post-treatment can yield a polymer compound, but if the purity of the polymer compound is low it may be purified by common methods such as recrystallization, continuous extraction with a Soxhlet extractor, or column chromatography.

[Composition]

A preferred embodiment of the first composition comprises at least one material selected from the group consisting of hole transport materials, electron transport materials and light-emitting materials, and a polymer compound according to the invention. Such a composition can be used as a charge transport material or light-emitting material, for example.

Hole transport materials, electron transport materials and light-emitting materials include hole transport materials, electron transport materials and light-emitting materials which may be present in the organic layers of light-emitting devices, as described hereunder.

The content ratio of the one or more materials selected from the group consisting of hole transport materials, electron transport materials and light-emitting materials and the polymer compound of the invention may be set according to the purpose of use. For use as a light-emitting material, for example, the amount of the polymer compound is usually 20-99 parts by weight and more preferably 40-95 parts by weight, with respect to 100 parts by weight as the total weight of the composition.

The polystyrene-equivalent number-average molecular weight of the first composition will usually be $1\times10^3$ to $1\times10^8$ and is preferably $1\times10^4$ to $1\times10^6$. The polystyrene-equivalent weight-average molecular weight of the composition will usually be $1\times10^3$ to $1\times10^8$, and for satisfactory film formability and more excellent luminous efficiency of the light-emitting device to be obtained, it is preferably $1\times10^4$ to $5\times10^6$. The average molecular weight of the composition is the value obtained by GPC analysis of the composition.

A preferred embodiment of the second composition is a composition comprising a polymer compound of the invention and a solvent. Such a composition is often referred to as "solution", "ink" or "ink composition", and will hereunder be referred to as "solution of the invention".

The solution of the invention is useful for fabrication of elements by coating, such as in ink jet printing method or press printing method. In addition to the polymer compound and solvents, the solution of the invention may also contain hole transport materials, electron transport materials, light-emitting materials, stabilizers, thickeners (high-molecular-weight compounds or poor solvents for increased viscosity), low-molecular-weight compounds to lower the viscosity, surfactants (to lower the surface tension), antioxidants and the like.

The proportion of the polymer compound of the invention in the solution of the invention will usually be 0.1-99.9 parts by weight, and is preferably 0.1-10 parts by weight, more preferably 0.2-7 parts by weight and even more preferably 0.5-2 parts by weight, with respect to 100 parts by weight of the solution.

The viscosity of the solution of the invention may be adjusted depending on the type of printing method, but when the solution is to be passed through a discharge apparatus as in ink jet printing method, the viscosity is preferably in the range of 1-20 mPa·s at 25° C. to prevent clogging or curving trajectory of the ink during discharge.

A high-molecular-weight compound to be used as a thickener may be soluble in the same solvents as the polymer compound without interfering with luminescence or charge transport. For example, high-molecular-weight polystyrene or high-molecular-weight polymethyl methacrylate may be used. These high-molecular-weight compounds preferably have polystyrene-equivalent weight-average molecular weights of 500,000 or greater and more preferably 1,000,000 or greater.

A poor solvent may be used as a thickener. The viscosity can be increased by adding a small amount of a poor solvent for the solid portion in the solution of the invention. When a poor solvent is added for this purpose, the type and amount of solvent may be selected in a range so that the solid portion in the solution is not deposited. In consideration of stability during storage, the amount of poor solvent is preferably no greater than 50 parts by weight and even more preferably no greater than 30 parts by weight with respect to 100 parts by weight of the total solution.

An antioxidant is used to improve the storage stability of the solution of the invention. An antioxidant may be one that is soluble in the same solvents as the polymer compound of the invention and does not interfere with luminescence or charge transport. Examples include phenol-based antioxidants and phosphorus-based antioxidants.

The solvent in the solution of the invention is preferably one that can dissolve or evenly disperse the solid components in the solution. Solvents include chlorine-based solvents such as chloroform, methylene chloride, 1,2-dichloroethane, 1,1,2-trichloroethane, chlorobenzene and o-dichlorobenzene, ether-based solvents such as tetrahydrofuran, dioxane, anisole and 4-methylanisole, aromatic hydrocarbon-based solvents such as toluene, xylene, mesitylene, ethylbenzene, n-hexylbenzene and cyclohexylbenzene, aliphatic hydrocarbon-based solvents such as cyclohexane, methylcyclohexane, n-pentane, n-hexane, n-heptane, n-octane, n-nonane and n-decane, ketone-based solvents such as acetone, methyl ethyl ketone, cyclohexanone, benzophenone and acetophenone, ester-based solvents such as ethyl acetate, butyl acetate, ethyl cellosolve acetate, methyl benzoate and phenyl acetate, polyhydric alcohols such as ethylene glycol, ethyleneglycol monobutyl ether, ethyleneglycol monoethyl ether, ethyleneglycol monomethyl ether, dimethoxyethane, propylene glycol, diethoxymethane, triethyleneglycol monoethyl ether, glycerin and 1,2-hexanediol, and their derivatives, alcohol-based solvents such as methanol, ethanol, propanol, isopropanol and cyclohexanol, sulfoxide-based solvents such as dimethyl sulfoxide, and amide-based solvents such as N-methyl-2-pyrrolidone and N,N-dimethylformamide. These solvents may be used alone or in combinations of two or more.

For increased solubility of the polymer compound and increased uniformity and viscosity characteristics during film formation, there are preferred aromatic hydrocarbon-based solvents, ether-based solvents, aliphatic hydrocarbon-based solvents, ester-based solvents and ketone-based solvents, and there are more preferred toluene, xylene, ethylbenzene, diethylbenzene, trimethylbenzene, n-propylbenzene, isopropylbenzene, n-butylbenzene, isobutylbenzene, sec-butylbenzene, n-hexylbenzene, cyclohexylbenzene, 1-methylnaphthalene, tetralin, anisole, 4-methylanisole, ethoxybenzene, cyclohexane, bicyclohexyl, cyclohexenylcyclohexanone, n-heptylcyclohexane, n-hexylcyclohexane, decalin, methyl benzoate, cyclohexanone, 2-propylcyclohexanone, 2-heptanone, 3-heptanone, 4-heptanone, 2-octanone, 2-nonanone, 2-decanone, dicyclohexyl ketone, acetophenone and benzophenone.

For satisfactory film formability and element characteristics, the solvent is preferably a combination of two or more solvents, more preferably a combination of 2 to 3 different solvents, and particularly preferably a combination of 2 different solvents.

When two different solvents are included in the solution of the invention, one of them may be in solid state at 25° C. For satisfactory film formability, one of the solvents preferably has a boiling point of 180° C. or higher and more preferably 200° C. or higher. In order to obtain satisfactory viscosity, the polymer compound preferably dissolves in both solvents to a concentration of 1 wt % or greater at 60° C., and the polymer compound preferably dissolves in one of the two solvents to a concentration of 1 wt % or greater at 25° C.

When two or more different solvents are present in the solution of the invention, in order to obtain satisfactory viscosity and film formability, the solvent with the highest boiling point is preferably present at 40-90 wt %, more preferably at 50-90 wt % and even more preferably at 65-85 wt % of the total weight of solvents in the solution.

The polymer compound of the invention in the solution of the invention may be of a single type or 2 or more types. A high-molecular-weight compound other than a polymer compound of the invention may also be included in a range that does not impair the element characteristics.

The solution of the invention may also comprise water or a metal or its salt, in a range of 1-1000 ppm by weight. Metals include lithium, sodium, calcium, potassium, iron, copper, nickel, aluminum, zinc, chromium, manganese, cobalt, platinum and iridium. The solution of the invention may also contain silicon, phosphorus, fluorine, chlorine, bromine or the like in ranges of 1-1000 ppm by weight.

[Film]

A film according to a preferred embodiment comprises a polymer compound of the invention, i.e. it is formed using a polymer compound of the invention. The film may be one comprising the polymer compound of the invention as is, or comprising the polymer compound of the invention with crosslinks within molecules and/or between molecules. The film of this embodiment is, for example, a light-emitting thin-film, a conductive thin-film or an organic semiconductor thin-film.

The film of this embodiment may be formed by spin coating method, casting method, microgravure coating method, gravure coating method, bar coating method, roll coating method, wire bar coating method, dip coating method, spray coating method, screen printing method, flexographic printing method, offset printing method, ink jet printing method, capillary coating method or nozzle coating method, for example. It is preferably formed by screen printing method, flexographic printing method, offset printing method or ink jet printing method, and more preferably by an ink-jet method.

When the solution of the invention is used to form a film, heating may be performed at a temperature of 100° C. or higher because of the high glass transition temperature of the polymer compound of the invention in the solution, and reduction in the element characteristics is minimal even with heating at a temperature of 130° C. Heating may even be suitable at a temperature of 160° C. or higher, depending on the type of polymer compound.

The light-emitting film has a light-emitting quantum yield of preferably 30% or greater, more preferably 50% or greater, even more preferably 60% or greater and particularly preferably 70% or greater, for satisfactory element brightness and initial light-emitting voltage.

For a conductive film, the surface resistance is preferably no greater than 1K Ω/sq., more preferably no greater than 100 Ω/sq. and even more preferably no greater than 10 Ω/sq. The conductive film may be doped with a Lewis acid, ionic compound or the like, thereby further increasing the electric conductivity.

The greater of the electron mobility or hole mobility of the organic semiconductor film is preferably $1\times10^{-5}$ cm$^2$/V·s or greater, more preferably $1\times10^{-3}$ cm$^2$/V·s or greater and even more preferably $1\times10^{-1}$ cm$^2$/V·s or greater. An organic transistor can be fabricated by forming the organic semiconductor film on a Si board comprising a gate electrode and an insulating film made of SiO$_2$ or the like, and then forming a source electrode and drain electrode of Au or the like.

[Light-Emitting Device]

Preferred embodiments of light-emitting devices will now be explained.

A light-emitting device according to a preferred embodiment has electrodes consisting of an anode and a cathode, and a layer comprising the aforementioned polymer compound formed between the electrodes. A layer comprising the polymer compound of the invention is a layer formed using the polymer compound of the invention, and the layer includes those comprising the polymer compound of the invention as is, or comprising the polymer compound of the invention with crosslinks within molecules and/or between molecules.

The layer comprising the polymer compound of the invention preferably consists of one or more light-emitting layers, hole transport layers, hole injection layers, electron transport layers, electron injection layers or interlayers, more preferably one or more layers from among electron transport layers, electron injection layers and light-emitting layers, and even more preferably a light-emitting layer.

A light-emitting layer is a layer having a light-emitting function. A hole transport layer is a layer having a hole transporting function. An electron transport layer is a layer having an electron transporting function. An interlayer is a layer situated between the light-emitting layer and anode and adjacent to the light-emitting layer, performing the role of separating the light-emitting layer and anode, or the light-emitting layer and the hole injection layer or hole transport layer. Electron transport layers and hole transport layers are collectively referred to as "charge transport layers", and electron injection layers and hole injection layers are collectively referred to as "charge injection layers". The light-emitting layer, hole transport layer, hole injection layer, electron transport layer, electron injection layer and interlayer may each consist of a single layer or two or more layers.

When a layer comprising the polymer compound is a light-emitting layer, the light-emitting layer may further comprise a hole transport material, electron transport material, light-emitting material, and additives that extend the luminance life of the light-emitting device. The term "light-emitting material" as used herein refers to a material exhibiting fluorescence and/or phosphorescence (excluding polymer compounds of the invention).

When the layer comprising a polymer compound comprises both the polymer compound of the invention and a hole transport material, the proportion of the hole transport material with respect to 100 parts by weight as the total of the polymer compound of the invention and the hole transport material will normally be 1-80 parts by weight, and is preferably 5-60 parts by weight.

When the layer comprising a polymer compound comprises both the polymer compound of the invention and an electron transport material, the proportion of the electron transport material with respect to 100 parts by weight as the total of the polymer compound of the invention and the electron transport material will also normally be 1-80 parts by weight, and is preferably 5-60 parts by weight.

When the layer comprising a polymer compound comprises both the polymer compound of the invention and a light-emitting material, the proportion of the light-emitting material with respect to 100 parts by weight as the total of the polymer compound of the invention and the light-emitting material will normally be 1-80 parts by weight, and is preferably 5-60 parts by weight.

When a layer comprising a polymer compound comprises both the polymer compound of the invention and 2 or more selected from the group consisting of hole transport materials, electron transport materials and light-emitting materials, the proportion of the light-emitting material with respect to 100 parts by weight as their total will normally be 1-50 parts by weight, and is preferably 5-40 parts by weight. The total proportion of the hole transport material and electron transport material with respect to 100 parts by weight as their total will normally be 1-50 parts by weight and is preferably 5-40 parts by weight.

The hole transport material, electron transport material and light-emitting material may also employ publicly known low-molecular-weight compounds, triplet emitting complexes and high-molecular-weight compounds.

High-molecular-weight compounds include polymers and copolymers (polymers and copolymers will hereinafter be collectively referred to as "(co)polymers") having fluorene-diyl groups as constitutional units, (co)polymers having arylene groups as constitutional units, (co)polymers having arylenevinylene groups as constitutional units and (co)polymers having divalent aromatic amine groups as constitutional units, which are described in WO99/13692, WO99/48160, GB2340304A, WO00/53656, WO01/19834, WO00/55927, GB2348316, WO00/46321, WO00/06665, WO99/54943, WO99/54385, U.S. Pat. No. 5,777,070, WO98/06773, WO97/05184, WO00/35987, WO00/53655, WO01/34722, WO99/24526, WO00/22027, WO00/22026, WO98/27136, US573636, WO98/21262, U.S. Pat. No. 5,741,921, WO97/09394, WO96/29356, WO96/10617, EP0707020, WO95/07955, Japanese Unexamined Patent Application Publication No. 2001-181618, Japanese Unexamined Patent Application Publication No. 2001-123156, Japanese Unexamined Patent Application Publication No. 2001-3045, Japanese Unexamined Patent Application Publication No. 2000-351967, Japanese Unexamined Patent Application Publication No. 2000-303066, Japanese Unexamined Patent Application Publication No. 2000-299189, Japanese Unexamined Patent Application Publication No. 2000-252065, Japanese Unexamined Patent Application Publication No. 2000-136379, Japanese Unexamined Patent Application Publication No. 2000-104057, Japanese Unexamined Patent Application Publication No. 2000-80167, Japanese Unexamined Patent Application Publication HEI No. 10-324870, Japanese Unexamined Patent Application Publication HEI No. 10-114891, Japanese Unexamined Patent Application Publication HEI No. 9-111233 and Japanese Unexamined Patent Application Publication HEI No. 9-45478.

Low-molecular-weight compounds include naphthalene derivatives, anthracene and its derivatives, perylene and its derivatives, polymethine-based, xanthene-based, coumarin-based and cyanine-based pigments, metal complexes of 8-hydroxyquinoline and its derivatives, aromatic amines, tetraphenylcyclopentadiene and its derivatives and tetraphenylbutadiene and its derivatives. Specifically, these include the compounds mentioned in Japanese Unexamined Patent Application Publication SHO No. 57-51781 and Japanese Unexamined Patent Application Publication SHO No. 59-194393.

Triplet emitting complexes include Ir(ppy)$_3$, Btp$_2$Ir(acac), FIrpic, COM-1, COM-2, COM-3 and ADS066GE marketed by American Dye Source, Inc., which have iridium as the central metal, PtOEP which has platinum as the central metal, and Eu(TTA)$_3$-phen which has europium as the central metal. These triplet emitting complexes are represented by the chemical formulas shown below. Specifically, they include the triplet emitting complexes described in Nature, (1998), 395, 151, Appl. Phys. Lett. (1999), 75(1), 4, Proc. SPIE-Int. Soc. Opt. Eng. (2001), 4105(Organic Light-Emitting Materials and Devices IV), 119, J. Am. Chem. Soc., (2001), 123, 4304, Appl. Phys. Lett., (1997), 71(18), 2596, Syn. Met., (1998), 94(1), 103, Syn. Met., (1999), 99(2), 1361, Adv. Mater., (1999), 11(10), 852, and Jpn. J. Appl. Phys., 34, 1883 (1995).

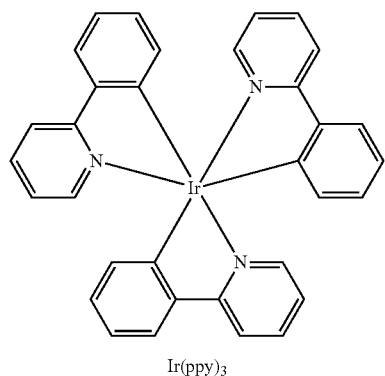

Ir(ppy)$_3$

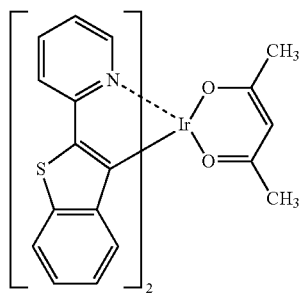

Btp$_2$Ir(acac)

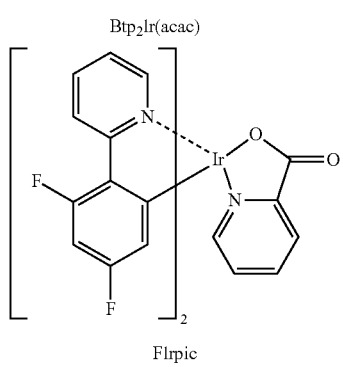

FIrpic

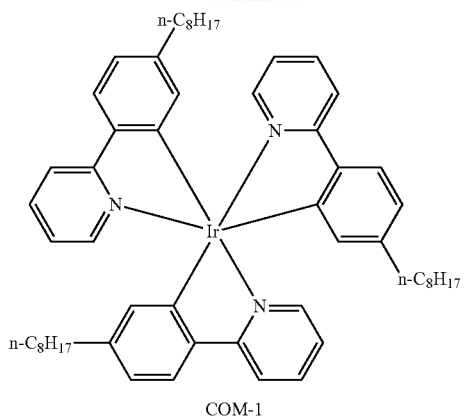

COM-1

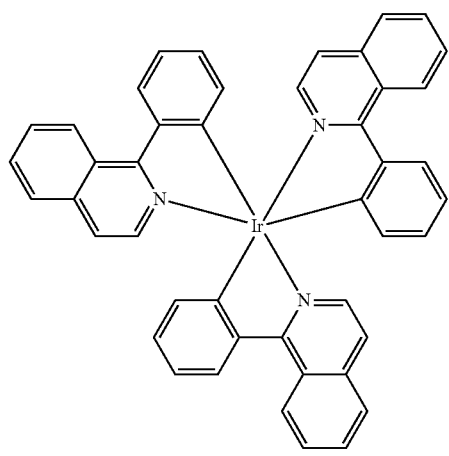

COM-2

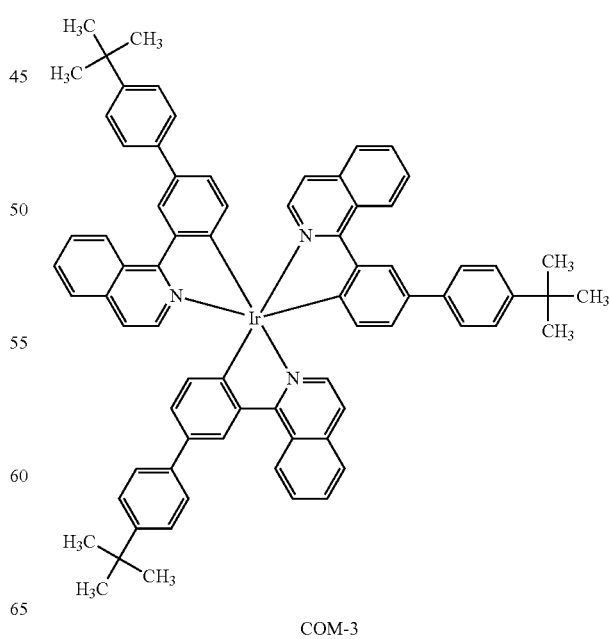

COM-3

101
-continued
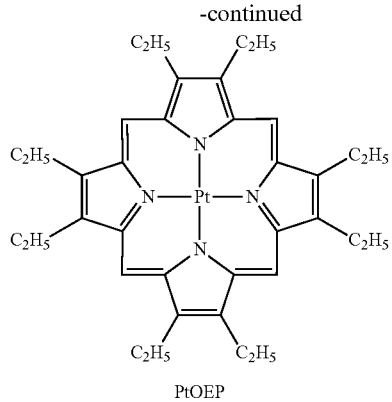
PtOEP
102
-continued
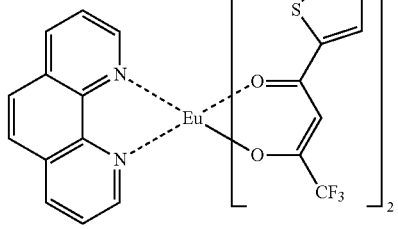
Eu(TTA)₃phen
Triplet emitting complexes may be bonded to the main chain, side chains or ends of a polymer compound of the invention. Specific examples of such polymer compounds include the following polymer compounds (PB-1) and (PB-2).
Polymer compound (PB-1)
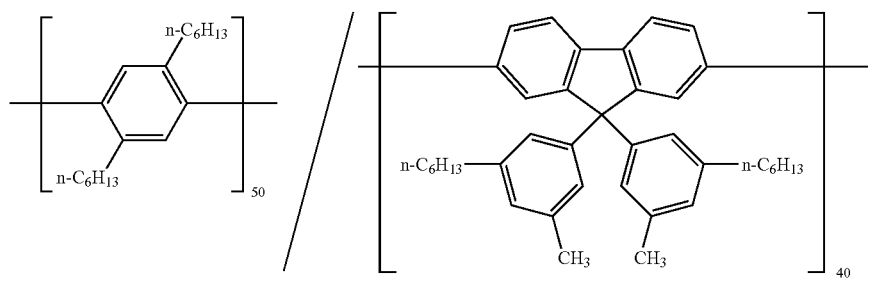
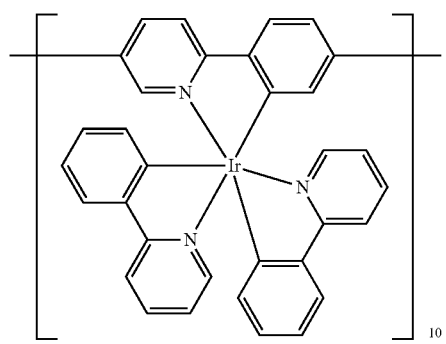
Polymer compound (PB-2)
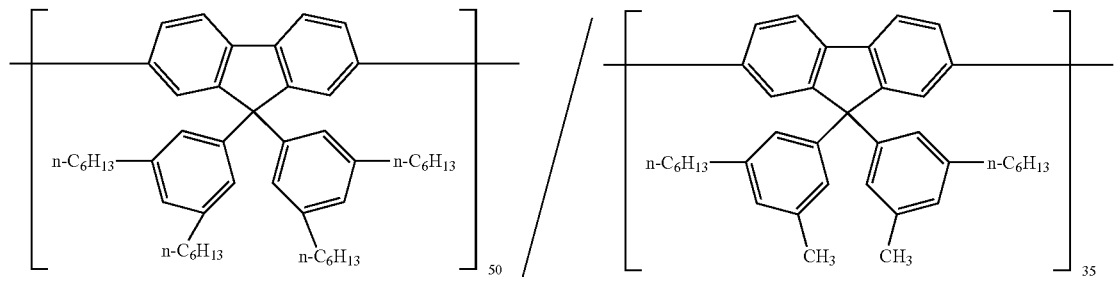

-continued

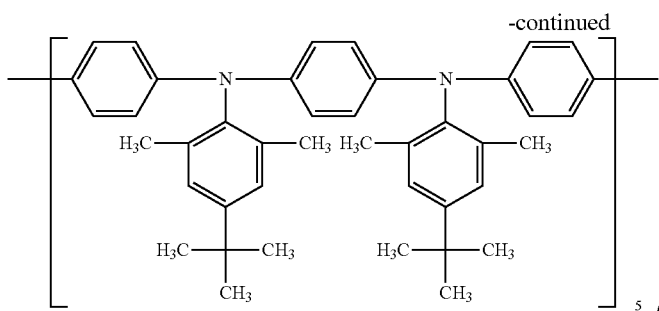

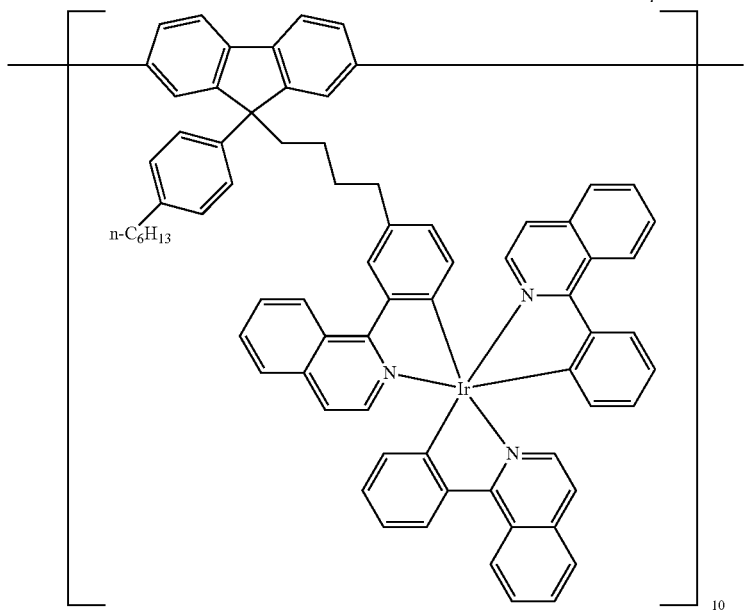

Additives include bipyridyls such as 2,2'-bipyridyl, 3,3'-bipyridyl and 4,4'-bipyridyl, and bipyridyl derivatives such as 4-methyl-2,2'-bipyridyl, 5-methyl-2,2'-bipyridyl and 5,5'-dimethyl-2,2'-bipyridyl.

The optimum thickness of the light-emitting layer will differ depending on the material used, and it may be selected so that optimal values are obtained for the driving voltage and luminous efficiency. This will usually be between 1 nm and 1 μm, preferably between 2 nm and 500 nm, more preferably between 5 nm and 200 nm, and even more preferably between 50 nm and 150 nm.

The method of forming the light-emitting layer may involve formation of a film from a solution. The film formation from a solution may be accomplished by a coating method such as spin coating method, casting method, microgravure coating method, gravure coating method, bar coating method, roll coating method, wire bar coating method, dip coating method, spray coating method, screen printing method, flexographic printing method, offset printing method, ink jet printing method, capillary coating method or nozzle coating method. Preferred among these are printing methods such as screen printing method, flexographic printing method, offset printing method and ink jet printing method, to facilitate pattern formation and separate coating of multiple colors.

Examples of solvents to be used in film formation from a solution include chlorine-based solvents such as chloroform, methylene chloride, 1,2-dichloroethane, 1,1,2-trichloroethane, chlorobenzene and o-dichlorobenzene, ether-based solvents such as tetrahydrofuran and dioxane, aromatic hydrocarbon-based solvents such as toluene, xylene, mesitylene, ethylbenzene, n-hexylbenzene, cyclohexylbenzene, anisole and 4-methylanisole, aliphatic hydrocarbon-based solvents such as cyclohexane, methylcyclohexane, n-pentane, n-hexane, n-heptane, n-octane, n-nonane and n-decane, ketone-based solvents such as acetone, methyl ethyl ketone and cyclohexanone, ester-based solvents such as ethyl acetate, butyl acetate and ethyl cellosolve acetate, polyhydric alcohols such as ethylene glycol, ethyleneglycol monobutyl ether, ethyleneglycol monoethyl ether, ethyleneglycol monomethyl ether, dimethoxyethane, propylene glycol, diethoxymethane, triethyleneglycol monoethyl ether, glycerin and 1,2-hexanediol, and their derivatives, alcohol-based solvents such as methanol, ethanol, propanol, isopropanol and cyclohexanol, sulfoxide-based solvents such as dimethyl sulfoxide, and amide-based solvents such as N-methyl-2-pyrrolidone and N,N-dimethylformamide. These solvents may be used alone or in combinations of two or more.

Light-emitting devices include light-emitting devices having an electron transport layer formed between a cathode and a light-emitting layer, light-emitting devices having a hole transport layer formed between an anode and a light-emitting layer, and light-emitting devices having an electron transport layer formed between a cathode and a light-emitting layer and having a hole transport layer formed between an anode and a light-emitting layer.

Examples of such light-emitting device structures include the following structures a) to d).

a) Anode/light-emitting layer/cathode
b) Anode/hole transport layer/light-emitting layer/cathode
c) Anode/light-emitting layer/electron transport layer/cathode
d) Anode/hole transport layer/light-emitting layer/electron transport layer/cathode
(Here, the "/" indicates that the layers are laminated adjacent to each other; same hereunder.)

In each of these structures, an interlayer may be provided between the light-emitting layer and anode, adjacent to the light-emitting layer. Examples of such light-emitting device structures include the following structures a') to d').
a') Anode/interlayer/light-emitting layer/cathode
b') Anode/hole transport layer/interlayer/light-emitting layer/cathode
c') Anode/interlayer/light-emitting layer/electron transport layer/cathode
d') Anode/hole transport layer/interlayer/light-emitting layer/electron transport layer/cathode When the light-emitting device has a hole transport layer, the hole transport layer will usually contain the hole transport material (high-molecular-weight compound or low-molecular-weight compound). Examples of hole transport materials include polyvinylcarbazole and its derivatives, polysilane and its derivatives, polysiloxane derivatives having aromatic amines on side chains or the main chain, pyrazoline derivatives, arylamine derivatives, stilbene derivatives, triphenyldiamine derivatives, polyaniline and its derivatives, polythiophene and its derivatives, polypyrrole and its derivatives, polyp-phenylenevinylene) and its derivatives and poly(2,5-thienylenevinylene) and its derivatives, as well as those described in Japanese Unexamined Patent Application Publication SHO No. 63-70257 and No. 63-175860 and Japanese Unexamined Patent Application Publication HEI No. 2-135359, No. 2-135361, No. 2-209988, No. 3-37992 and No. 3-152184.

Preferred among these as high-molecular-weight compounds are polyvinylcarbazole and its derivatives, polysilane and its derivatives, polysiloxane derivatives having aromatic amine compound group on side chains or the main chain, polyaniline and its derivatives, polythiophene and its derivatives, polyp-phenylenevinylene) and its derivatives and poly(2,5-thienylenevinylene) and its derivatives, with polyvinylcarbazole and its derivatives, polysilane and its derivatives and polysiloxane derivatives having aromatic amines on side chains or the main chain being more preferred.

Pyrazoline derivatives, arylamine derivatives, stilbene derivatives and triphenyldiamine derivatives are preferred as low-molecular-weight compounds. These low-molecular-weight compounds are preferably used after dispersion in a high molecular binder.

As macromolecular binders there are preferably used compounds that produce minimal interference with charge transport, and with weak absorption for visible light. Examples include poly(N-vinylcarbazole), polyaniline and its derivatives, polythiophene and its derivatives, poly(p-phenylenevinylene) and its derivatives, poly(2,5-thienylenevinylene) and its derivatives, polycarbonates, polyacrylates, polymethyl acrylates, polymethyl methacrylates, polystyrenes, polyvinyl chlorides, polysiloxanes and the like.

Polyvinylcarbazole and its derivatives may be obtained, for example, by cationic polymerization or radical polymerization of vinyl monomers.

Examples of polysilane and its derivatives include the compounds mentioned in Chem. Rev. Vol. 89, p. 1359 (1989) and GB2300196. The synthesis methods described in this literature may be used, although the Kipping method is particularly preferred.

Because a structure derived from siloxane has essentially no hole transport property, polysiloxane and its derivatives are preferably compounds having a structure with a low-molecular-weight hole transport material on a side chain or the main chain, and more preferably compounds having a structure derived from a hole transporting aromatic amine on a side chain or the main chain.

The method of forming the hole transport layer may be film formation from a mixture with a high molecular binder, if a low-molecular-weight compound is used. The method may be film formation from a solution, if a high-molecular-weight compound is used.

The solvent used for film formation from a solution is preferably one that can dissolve or evenly disperse the hole transport material. Examples of solvents include chlorine-based solvents such as chloroform, methylene chloride, 1,2-dichloroethane, 1,1,2-trichloroethane, chlorobenzene and o-dichlorobenzene, ether-based solvents such as tetrahydrofuran and dioxane, aromatic hydrocarbon-based solvents such as toluene, xylene, mesitylene, ethylbenzene, n-hexylbenzene, cyclohexylbenzene, anisole and 4-methylanisole, aliphatic hydrocarbon-based solvents such as cyclohexane, methylcyclohexane, n-pentane, n-hexane, n-heptane, n-octane, n-nonane and n-decane, ketone-based solvents such as acetone, methyl ethyl ketone and cyclohexanone, ester-based solvents such as ethyl acetate, butyl acetate and ethyl cellosolve acetate, polyhydric alcohols such as ethylene glycol, ethyleneglycol monobutyl ether, ethyleneglycol monoethyl ether, ethyleneglycol monomethyl ether, dimethoxyethane, propylene glycol, diethoxymethane, triethyleneglycol monoethyl ether, glycerin and 1,2-hexanediol, and their derivatives, alcohol-based solvents such as methanol, ethanol, propanol, isopropanol and cyclohexanol, sulfoxide-based solvents such as dimethyl sulfoxide, and amide-based solvents such as N-methyl-2-pyrrolidone and N,N-dimethylformamide. These solvents may be used alone or in combinations of two or more.

The film formation from a solution may be accomplished by a coating method such as spin coating method, casting method, microgravure coating method, gravure coating method, bar coating method, roll coating method, wire bar coating method, dip coating method, spray coating method, screen printing method, flexographic printing method, offset printing method, ink jet printing method, capillary coating method or nozzle coating method.

The optimum value for the thickness of the hole transport layer will differ depending on the material used, and it may be selected for suitable values for the driving voltage and luminous efficiency, but since the thickness must be such that pinholes are not generated, it is usually 1 nm to 1 µm, preferably 2 nm to 500 nm, and even more preferably 5 nm to 200 nm.

When the light-emitting device has an electron transport layer, the electron transport layer will usually contain the electron transport material (high-molecular-weight compound or low-molecular-weight compound). A known electron transport material may be used. Examples include oxadiazole derivatives, quinodimethane and its derivatives, benzoquinone and its derivatives, naphthoquinone and its derivatives, anthraquinone and its derivatives, tetracyanoquinodimethane and its derivatives, fluorenone derivatives, diphenyldicyanoethylene and its derivatives, diphenoquinone derivatives, metal complexes of 8-hydroxyquinoline and its derivatives, polyquinoline and its derivatives, polyquinoxaline and its derivatives and polyfluorene and its derivatives, as well as the compounds mentioned in Japanese Unexamined Patent Application Publication SHO No. 63-70257, Japanese Unexamined Patent Application Publication SHO No. 63-175860, Japanese Unexamined Patent Application Publication HEI No. 2-135359, Japanese Unexamined Patent Application Publication HEI No. 2-135361, Japanese Unexamined Patent Application Publication HEI No. 2-209988, Japanese Unexamined Patent Application Publication HEI No. 3-37992 and Japanese Unexamined Patent Application Publication HEI No. 3-152184. Preferred among these are oxadiazole derivatives, benzoquinone and its derivatives, anthraquinone and its derivatives, metal complexes of 8-hydroxyquinoline and its derivatives, polyquinoline and its derivatives, polyquinoxaline and its derivatives and polyfluorene and its derivatives, with 2-(4-biphenylyl)-5-(4-tert-butylphenyl)-1,3,4-oxadiazole, benzoquinone, anthraquinone, tris(8-quinolinol)aluminum and polyquinoline being even more preferred.

The method of forming the electron transport layer may be vacuum vapor deposition method from a powder state or film formation method from a solution or molten state, if a low-molecular-weight compound is used. When a high-molecular-weight compound is used, the method may be film formation from a solution or molten state. The aforementioned high molecular binder may also be used for film formation from a solution or molten state.

The solvent used for film formation from a solution is preferably a solvent that can dissolve or evenly disperse the electron transport material and/or high molecular binder. Examples of solvents include chlorine-based solvents such as chloroform, methylene chloride, 1,2-dichloroethane, 1,1,2-trichloroethane, chlorobenzene and o-dichlorobenzene, ether-based solvents such as tetrahydrofuran and dioxane, aromatic hydrocarbon-based solvents such as toluene, xylene, mesitylene, ethylbenzene, n-hexylbenzene, cyclohexylbenzene, anisole and 4-methylanisole, aliphatic hydrocarbon-based solvents such as cyclohexane, methylcyclohexane, n-pentane, n-hexane, n-heptane, n-octane, n-nonane and n-decane, ketone-based solvents such as acetone, methyl ethyl ketone and cyclohexanone, ester-based solvents such as ethyl acetate, butyl acetate and ethyl cellosolve acetate, polyhydric alcohols such as ethylene glycol, ethyleneglycol monobutyl ether, ethyleneglycol monoethyl ether, ethyleneglycol monomethyl ether, dimethoxyethane, propylene glycol, diethoxymethane, triethyleneglycol monoethyl ether, glycerin and 1,2-hexanediol, and their derivatives, alcohol-based solvents such as methanol, ethanol, propanol, isopropanol and cyclohexanol, sulfoxide-based solvents such as dimethyl sulfoxide, and amide-based solvents such as N-methyl-2-pyrrolidone and N,N-dimethylformamide. These solvents may be used alone or in combinations of two or more.

The film formation from a solution or molten state may be accomplished by a coating method such as spin coating method, casting method, microgravure coating method, gravure coating method, bar coating method, roll coating method, wire bar coating method, dip coating method, spray coating method, screen printing method, flexographic printing method, offset printing method, ink jet printing method, capillary coating method or nozzle coating method.

The optimum value for the thickness of the electron transport layer will differ depending on the material used, and it may be selected for suitable values for the driving voltage and luminous efficiency, but since the thickness must be such that pinholes are not generated, it is usually 1 nm to 1 preferably 2 nm to 500 nm, and even more preferably 5 nm to 200 nm.

The hole injection layer and electron injection layer, of the charge transport layers formed adjacent to the electrodes, have the function of improving the charge injection efficiency from the electrodes, and have an effect of lowering the driving voltage of the light-emitting device.

In order to increase adhesiveness with and improve charge injection from the electrodes, there may be provided adjacent to the electrodes a charge injection layer or insulating layer (normally with a mean thickness of 0.5-4.0 nm, same hereunder). A thin buffer layer may be inserted at the interface with the charge transport layer or light-emitting layer to improve the interfacial adhesiveness and prevent intermixture.

The order and number of the laminated layers and the thickness of each layer may be modified in consideration of the desired luminous efficiency and element lifespan.

For this embodiment, light-emitting devices provided with charge injection layers include light-emitting devices provided with a charge injection layer adjacent to the cathode and light-emitting devices provided with a charge injection layer adjacent to the anode. Examples of such light-emitting device structures include the following structures e) to p).

e) Anode/charge injection layer/light-emitting layer/cathode
f) Anode/light-emitting layer/charge injection layer/cathode
g) Anode/charge injection layer/light-emitting layer/charge injection layer/cathode
h) Anode/charge injection layer/hole transport layer/light-emitting layer/cathode
i) Anode/hole transport layer/light-emitting layer/charge injection layer/cathode
j) Anode/charge injection layer/hole transport layer/light-emitting layer/charge injection layer/cathode
k) Anode/charge injection layer/light-emitting layer/electron transport layer/cathode
l) Anode/light-emitting layer/electron transport layer/charge injection layer/cathode
m) Anode/charge injection layer/light-emitting layer/electron transport layer/charge injection layer/cathode
n) Anode/charge injection layer/hole transport layer/light-emitting layer/electron transport layer/cathode
o) Anode/hole transport layer/light-emitting layer/electron transport layer/charge injection layer/cathode
p) Anode/charge injection layer/hole transport layer/light-emitting layer/electron transport layer/charge injection layer/cathode In each of these structures, an interlayer may be provided between the light-emitting layer and anode, adjacent to the light-emitting layer. In this case, the interlayer may even serve as the hole injection layer and/or the hole transport layer.

The charge injection layer may be a layer comprising a conductive polymer, a layer provided between the anode and hole transport layer which comprises a material having an ionization potential between that of the anode material and the hole transport material in the hole transport layer, or a layer provided between the cathode and electron transport layer which comprises a material having electron affinity between that of the cathode material and the electron transport material in the electron transport layer.

When the charge injection layer is a layer comprising a conductive polymer, the electric conductivity of the conductive polymer is preferably $1\times10^{-5}$ to $1\times10^{3}$ S/cm, and in order to allow the leak current between light-emitting picture elements to be reduced, it is more preferably $1\times10^{-5}$ to $1\times10^{2}$ S/cm and even more preferably $1\times10^{-5}$ to $1\times10^{1}$ S/cm. In order for the electric conductivity of the conductive polymer to be within this range, the conductive polymer will usually be moderately doped with an ion.

The type of ion used for doping may be an anion for the hole injection layer or a cation for the electron injection layer. Examples of anions include polystyrenesulfonate ion, alkylbenzenesulfonate ion and camphorsulfonate ion. Examples of cations include lithium ion, sodium ion, potassium ion and tetrabutylammonium ion.

The material used in the charge injection layer may be selected in terms of the relationship with the material of the electrode or adjacent layers. Examples of materials to be used for the charge injection layer include conductive polymers, such as polyaniline and its derivatives, polythiophene and its derivatives, polypyrrole and its derivatives, polyphenylenevinylene and its derivatives, polythienylenevinylene and its derivatives, polyquinoline and its derivatives and polyquinoxaline and its derivatives, polymers comprising an aromatic amine structure on the main chain or a side chain, or metal phthalocyanines (copper phthalocyanine or the like), and carbon.

The material of the insulating layer may be a metal fluoride, metal oxide, organic insulating material, or the like. A light-emitting device provided with the insulating layer may be a light-emitting device with the insulating layer adjacent to the cathode or a light-emitting device with the insulating layer adjacent to the anode.

Examples of such light-emitting device structures include the following structures q) to ab).
q) Anode/insulating layer/light-emitting layer/cathode
r) Anode/light-emitting layer/insulating layer/cathode
s) Anode/insulating layer/light-emitting layer/insulating layer/cathode
t) Anode/insulating layer/hole transport layer/light-emitting layer/cathode
u) Anode/hole transport layer/light-emitting layer/insulating layer/cathode
v) Anode/insulating layer/hole transport layer/light-emitting layer/insulating layer/cathode
w) Anode/insulating layer/light-emitting layer/electron transport layer/cathode
x) Anode/light-emitting layer/electron transport layer/insulating layer/cathode
y) Anode/insulating layer/light-emitting layer/electron transport layer/insulating layer/cathode
z) Anode/insulating layer/hole transport layer/light-emitting layer/electron transport layer/cathode
aa) Anode/hole transport layer/light-emitting layer/electron transport layer/insulating layer/cathode
ab) Anode/insulating layer/hole transport layer/light-emitting layer/electron transport layer/insulating layer/cathode In each of these structures, an interlayer may be provided between the light-emitting layer and anode, adjacent to the light-emitting layer. In this case, the interlayer may even serve as the hole injection layer and/or the hole transport layer.

When an interlayer is employed in structures a) to ab), the interlayer is preferably provided between the anode and light-emitting layer, and it is preferably composed of a material with ionization potential between that of the anode or the hole injection layer or hole transport layer, and the polymer compound composing the light-emitting layer.

The material used in the interlayer may be a polyvinylcarbazole or a derivative thereof, a polyarylene derivative having an aromatic amine on a side chain or the main chain, or a polymer comprising an aromatic amine such as an arylamine derivative or triphenyldiamine derivative.

When a high-molecular-weight material is used, the film-forming method for the interlayer may be a method of film formation from a solution.

The solvent used for film formation from a solution is preferably one that can dissolve or evenly disperse the material to be used in the interlayer. Examples of solvents include chlorine-based solvents such as chloroform, methylene chloride, 1,2-dichloroethane, 1,1,2-trichloroethane, chlorobenzene and o-dichlorobenzene, ether-based solvents such as tetrahydrofuran and dioxane, aromatic hydrocarbon-based solvents such as toluene, xylene, mesitylene, ethylbenzene, n-hexylbenzene, cyclohexylbenzene, anisole and 4-methylanisole, aliphatic hydrocarbon-based solvents such as cyclohexane, methylcyclohexane, n-pentane, n-hexane, n-heptane, n-octane, n-nonane and n-decane, ketone-based solvents such as acetone, methyl ethyl ketone and cyclohexanone, ester-based solvents such as ethyl acetate, butyl acetate and ethyl cellosolve acetate, polyhydric alcohols such as ethylene glycol, ethyleneglycol monobutyl ether, ethyleneglycol monoethyl ether, ethyleneglycol monomethyl ether, dimethoxyethane, propylene glycol, diethoxymethane, triethyleneglycol monoethyl ether, glycerin and 1,2-hexanediol, and their derivatives, alcohol-based solvents such as methanol, ethanol, propanol, isopropanol and cyclohexanol, sulfoxide-based solvents such as dimethyl sulfoxide, and amide-based solvents such as N-methyl-2-pyrrolidone and N,N-dimethylformamide. These solvents may be used alone or in combinations of two or more.

The film formation from a solution may be accomplished by a coating method such as spin coating method, casting method, microgravure coating method, gravure coating method, bar coating method, roll coating method, wire bar coating method, dip coating method, spray coating method, screen printing method, flexographic printing method, offset printing method, ink jet printing method, capillary coating method or nozzle coating method.

The optimum thickness of the interlayer will differ depending on the material used, and it may be selected so that optimal values are obtained for the driving voltage and luminous efficiency. It will usually be 1 nm to 1 μm, preferably 2 to 500 nm and more preferably 5 to 200 nm.

When an interlayer is provided adjacent to the light-emitting layer, and especially when both layers are formed by a coating method, the materials of the two layers sometimes become mixed, resulting in undesirable effects on the element characteristics. When the light-emitting layer is to be formed by a coating method after the interlayer has been formed by coating, mixing between the materials of the two layers can be reduced by a method of forming the interlayer by coating and heating the interlayer to insolubilize it to the organic solvent that is to be used to form the light-emitting layer, and then subsequently forming the light-emitting layer. The heating temperature will normally be 150° C. to 300° C. The heating time will usually be between 1 minute and 1 hour. In this case, the heating may be followed by rinsing of the interlayer with the solvent to be used to form the light-emitting layer, before forming the light-emitting layer, in order to remove the components that have not been insolubilized to the solvent by heating. Such rinsing may be omitted if the insolubilization by heating has been sufficient. In order to achieve sufficient insolubilization by heating, it is preferred to use a compound having a polymerizable group in the molecule, as the high-molecular-weight compound to be used in the interlayer. The number of polymerizable groups is preferably at least 5% of the number of constitutional units in the molecule.

The substrate of the light-emitting device may be one that allows formation of an electrode and is not altered during formation of organic material layers. Examples include substrates made of materials such as glass, plastic, polymer films, silicon and the like. In the case of an opaque substrate, the opposite electrode is preferably transparent or semi-transparent.

Either or both the anode and cathode in a light-emitting device will usually be transparent or semi-transparent, but preferably the anode is transparent or semi-transparent.

The material of the anode may be a conductive metal oxide film or a semi-transparent metal film. Specifically, there may be used a film formed using a conductive compound composed of indium oxide, zinc oxide, tin oxide, or their complexes such as indium tin oxide (ITO) or indium zinc oxide, or NESA, gold, platinum, silver, copper or the like. ITO, indium zinc oxide and tin oxide are preferred among these. The forming method may be vacuum vapor deposition method, sputtering method, ion plating method, plating method or the like. The anode used may be an organic transparent conductive film made of polyaniline or its derivative or polythiophene or its derivative. The anode may even consist of a multilayer structure of 2 or more layers.

The thickness of the anode may be selected in consideration of light permeability and electric conductivity. For example, it may be 10 nm to 10 µm, preferably 20 nm to 1 µm and more preferably 50 to 500 nm.

In order to facilitate charge injection, there may be provided on the anode a layer composed of a phthalocyanine derivative, conductive polymer, carbon or the like, or an insulating layer composed of a metal oxide, metal fluoride, organic insulating material or the like.

The material for the cathode is preferably one with a low work function, e.g. a metal such as lithium, sodium, potassium, rubidium, cesium, beryllium, magnesium, calcium, strontium, barium, aluminum, scandium, vanadium, zinc, yttrium, indium, cerium, samarium, europium, terbium or ytterbium, or an alloy of two or more of these metals, or an alloy of one or more of these metals with one or more of gold, silver, platinum, copper, manganese, titanium, cobalt, nickel, tungsten or tin, or graphite or a graphite interlaminar compound. Examples of alloys include magnesium-silver alloys, magnesium-indium alloys, magnesium-aluminum alloys, indium-silver alloys, lithium-aluminum alloys, lithium-magnesium alloys, lithium-indium alloys and calcium-aluminum alloys. The cathode may also consist of a multilayer structure of 2 or more layers.

The thickness of the cathode may be adjusted in consideration of electric conductivity and durability. It will usually be 10 nm to 10 µm, preferably 20 nm to 1 µm and more preferably 50 to 500 nm.

The method used to form the cathode may be vacuum vapor deposition method, sputtering method, or a laminating method involving thermocompression bonding of a metal thin-film. Also, between the cathode and an organic layer (that is, any layer comprising a polymer compound of the invention) there may be provided a layer composed of a conductive polymer, or a layer with a mean thickness of no greater than 2 nm composed of a metal oxide, metal fluoride or organic insulating material, and a protective layer for protection of the light-emitting device may also be provided after formation of the cathode. For prolonged stable use of the light-emitting device, a protective layer and/or protective cover is preferably situated to protect the element from the external environment.

A protective layer may be a high-molecular-weight compound, metal oxide, metal fluoride or metal boride. The protective cover used may be a metal sheet, glass plate, or a plastic sheet subjected to low-permeability treatment on the surface. For example, there may be preferably employed a method of attaching and sealing a protective cover onto an element board with a thermosetting resin or photocuring resin. A spacer may be used to maintain spacing, thus helping to prevent damage to the element. If an inert gas such as nitrogen or argon is filled into the space, it is possible to prevent oxidation of the cathode. Also, placing a desiccant such as barium oxide in the space will help to prevent damage to the element by moisture adsorbed in the production steps or trace moisture infiltrating through the cured resin. It is preferred to employ one or more of these strategies.

FIG. 1 is a schematic cross-sectional view of an embodiment of a light-emitting device of the invention (a light-emitting device having construction (p) above). The light-emitting device 100 shown in FIG. 1 comprises a substrate 10, an anode 11 formed on the substrate 10, a hole injection layer 12, a hole transport layer 13, a light-emitting layer 14, an electron transport layer 15, an electron injection layer 16 and a cathode 17. The anode 11 is provided on the substrate 10 in contact with the substrate 10, and on the side of the anode 11 opposite the substrate 10 there are laminated the hole injection layer 12, hole transport layer 13, light-emitting layer 14, electron transport layer 15, electron injection layer 16 and cathode 17, in that order.

Figure 2:
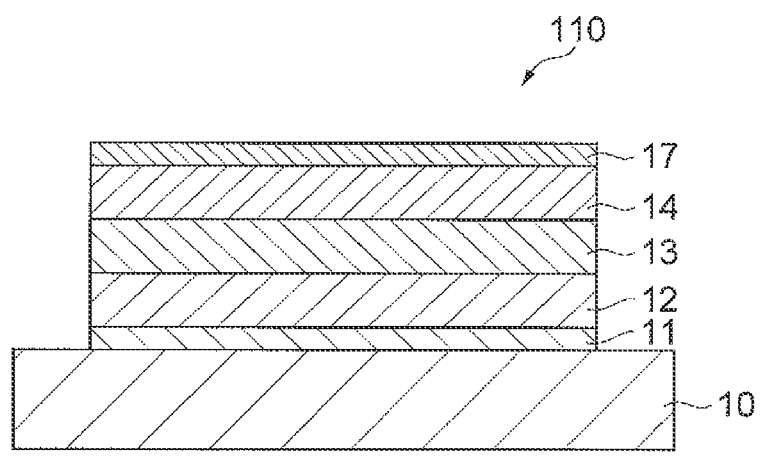
FIG. 2 is a schematic cross-sectional view showing another embodiment of a light-emitting device of the invention.

FIG. 2 is a schematic cross-sectional view of another embodiment of a light-emitting device of the invention (a light-emitting device having construction (h) above). The light-emitting device 110 shown in FIG. 2 comprises a substrate 10, an anode 11 formed on the substrate 10, a hole injection layer 12, a hole transport layer 13, a light-emitting layer 14 and a cathode 17. The anode 11 is provided on the substrate 10 in contact with the substrate, while the hole injection layer 12, hole transport layer 13, light-emitting layer 14 and cathode 17 are laminated in that order on the side of the anode 11 opposite the substrate 10 side.

The light-emitting device is useful as a planar light source, segment display device, dot matrix display device or liquid crystal display apparatus backlight.

A planar anode and cathode may be stacked together to obtain planar luminescence using the light-emitting device. Luminescence in a pattern form can be obtained by a method in which a mask with a patterned window is set on the front side of the planar light-emitting device, a method in which layers for non-luminous sections are formed extremely thin to render them essentially non-luminous, and a method in which an anode or cathode, or both electrodes, are formed in a pattern shape. By forming a pattern by any of these methods, and configuring some electrodes to be independently ON/OFF switchable, it is possible to obtain a segment type display device allowing display of numerals, characters or simple symbols. Alternatively, for a dot matrix display device, the anode and cathode may both be formed as stripes and configured in a crossing manner. A partial color display or multicolor display can also be formed by a method in which different types of polymer compounds with different light-emitting colors are coated or a method using a color filter or fluorescence conversion filter. The dot matrix display device may be passively driven or actively driven in combination with a TFT or the like. These display devices may be used for computers, televisions, portable terminals, cellular phones, car navigation systems, video camera viewfinders, and the like.

The planar light-emitting device is a selfluminous thin type, and can therefore also be suitably used as a backlight surface light source for a liquid crystal display device, or a planar illumination light source. Moreover, using a flexible substrate will allow its use as a curved light source or display device.

Figure 3:
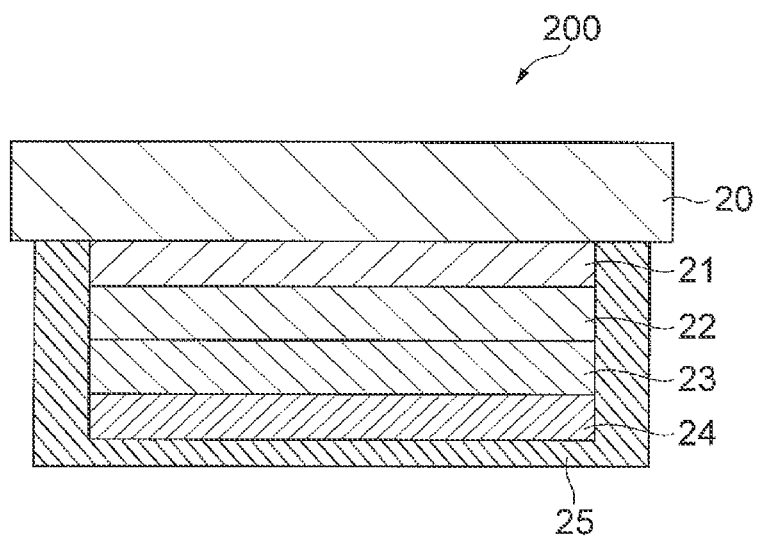
FIG. 3 is a schematic cross-sectional view showing an embodiment of a surface light source of the invention.

FIG. 3 is a schematic cross-sectional view showing an embodiment of a surface light source of the invention. The surface light source 200 shown in FIG. 3 comprises a substrate 20, an anode 21, a hole injection layer 22, a light-emitting layer 23, a cathode 24 and a protective layer 25. The anode 21 is provided on the substrate 20 in contact with the substrate 20, and the hole injection layer 22, light-emitting layer 23 and cathode 24 are laminated in that order on the side of the anode 21 opposite the substrate 20 side. The protective layer 25 is formed so as to cover the anode 21, charge injection layer 22, light-emitting layer 23 and cathode 24 that are formed on the substrate 20, and so as to contact the substrate 20 at the ends. The polymer compound is included in the light-emitting layer 23.

The surface light source 200 shown in FIG. 3 comprises light-emitting layers in addition to the light-emitting layer 23, and a red light-emitting material, blue light-emitting material and green light-emitting material are used in each light-emitting layer, with driving of each light-emitting layer being controlled to obtain a color display device.

EXAMPLES

The present invention will now be explained in greater detail through the following examples, with the understanding that these examples are in no way limitative on the invention.

[Measurement Method for Number-Average Molecular Weight and Weight-Average Molecular Weight]

Throughout the examples, the polystyrene-equivalent number-average molecular weights and the polystyrene-equivalent weight-average molecular weights were determined by gel permeation chromatography (GPC, trade name: LC-10Avp by Shimadzu Corp.). The polymer compound to be measured was dissolved in tetrahydrofuran to a concentration of about 0.5 wt % and 30 μL thereof was injected into the GPC. The GPC mobile phase was tetrahydrofuran, and the flow rate was 0.6 mL/min. The columns used were two TSK-gel SuperHM-H (Tosoh Corp.) columns and one TSKgel SuperH2000 (Tosoh Corp.) column, connected in series. The detector used was a differential refractometer (trade name: RID-10A, product of Shimadzu Corp.).

Synthesis Example 1

Synthesis of Compound 1-1

There were stirred 1-bromohexane (410 g, 2.48 mol), metal magnesium (60.7 g, 2.50 mol) and anhydrous tetrahydrofuran (2.5 L) under an inert gas atmosphere, to prepare solution 1-1.

After adding anhydrous tetrahydrofuran (2 L), 3,5-dibromotoluene (477 g, 1.91 mol) and 1,1-bis(diphenylphosphino) ferrocene dichloropalladium(II) dichloromethane complex (Pd(dppf).CH$_2$Cl$_2$, CAS:851232-71-8, 6.24 g, 7.64 mol) in a 6 L flask under an inert gas atmosphere, the mixture was stirred at 57° C. for 15 minutes. Next, solution 1-1 was added dropwise at rate which maintained a temperature of no higher than 60° C., and the mixture was stirred at 57° C. for 2 hours. The reaction mixture was then added to 10 wt % hydrochloric acid that had been cooled with an ice bath, and stirred, and extraction was performed with toluene. The obtained organic layer was rinsed twice with water and the organic layer was concentrated under reduced pressure to remove the solvent. This was followed by vacuum distillation and purification by column chromatography, to obtain 326 g of the target 3-n-hexyl-5-methylbromobenzene (compound 1-1 represented by the following formula).

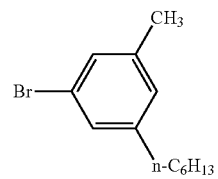

(Compound 1-1)

Synthesis Example 2

Synthesis of Compound 1-2

After adding 3-n-hexyl-5-methylbromobenzene (compound 1-1, 262 g, 1.026 mol) and anhydrous tetrahydrofuran (1.5 L) to a 3 L three-necked flask under an inert atmosphere and forming a homogeneous solution, it was cooled to −70° C. To the obtained solution there was added dropwise a 2.5 M n-butyllithium/hexane solution (380 mL, 0.95 mol), keeping the temperature of the solution at −70° C., and the mixture was stirred for 4 hours at the same temperature to obtain solution A.

Separately, 2-methoxycarbonyl-4,4'-dibromobiphenyl (160 g, 0.432 mol) and anhydrous tetrahydrofuran (500 mL) were added to a 1 L two-necked flask, and a homogeneous solution was prepared (solution B).

Solution B was added dropwise to solution A while keeping the temperature of solution A at −70° C., and the mixture was stirred. The reaction solution was then stirred at room temperature for 15 hours. Water (150 mL) was added to the reaction solution at 0° C., and the mixture was stirred. After then removing the solvent by concentration under reduced pressure and adding hexane (1 L) and water (200 mL) to the residue, the mixture was stirred and allowed to stand, and the produced aqueous layer was removed to obtain an organic layer. After rinsing the organic layer with brine (200 mL) and drying over anhydrous magnesium sulfate, it was concentrated under reduced pressure to obtain compound 1-2 represented by the following formula as a white solid.

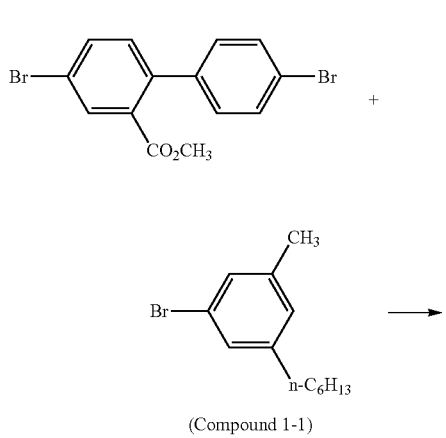

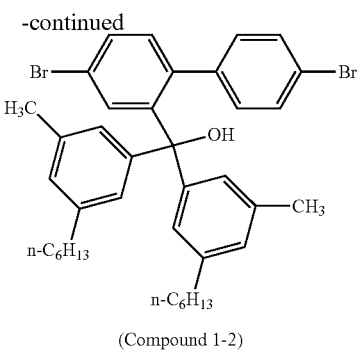

(Compound 1-2)

Synthesis Example 3

Synthesis of Compound 1-3

After adding compound 1-2 (299 g) obtained in Synthesis Example 2 and anhydrous dichloromethane (900 mL) to a 3 L three-necked flask under an inert atmosphere, the mixture was cooled to 5° C. After adding a boron trifluoride-diethyl ether complex (224 mL, 1.82 mmol) dropwise to the obtained mixture while keeping the temperature in the range of 0° C. to 5° C., the mixture was stirred overnight at room temperature. The reaction solution was carefully poured into 2 L of ice water, stirred for 30 minutes and allowed to stand, and the separated aqueous layer was removed from the organic layer. After adding a 10 wt % potassium phosphate aqueous solution (1 L) to the organic layer and stirring for 2 hours, the mixture was allowed to stand and the produced aqueous layer was removed from the organic layer. The obtained organic layer was rinsed with water (1 L) and dried over anhydrous magnesium sulfate, and then concentrated to distill off the solvent and obtain an oily liquid. Methanol was added to the oily liquid, and a solid was obtained. The solid was subjected to recrystallization using n-butyl acetate and methanol, to obtain compound 1-3 represented by the following formula (240 g).

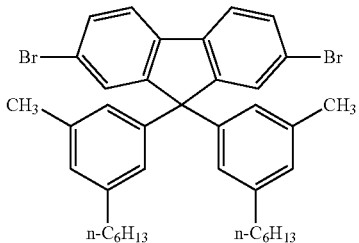

(Compound 1-3)

Synthesis Example 4

Synthesis of Compound 1

After adding compound 1-3 synthesized in Synthesis Example 3 (80 g, 0.119 mmol), bis(pinacolato)diboron (66.45 g, 0.26 mol), 1,1-bis(diphenylphosphino)ferrocene-dichloropalladium(II)-dichloromethane complex (Pd(dppf).CH$_2$Cl$_2$, 1.457 g, 1.8 mmol), 1,1-bis(diphenylphosphino) ferrocene (0.989 g, 1.8 mmol), anhydrous 1,4-dioxane (800 mL) and potassium acetate (70.04 g, 0.71 mol) to a three-necked flask, the mixture was stirred at 100° C. for 20 hours.

The reaction solution was cooled to room temperature and then passed through silica gel, the silica gel was rinsed with toluene, and the obtained solution was concentrated to remove the solvent and obtain a brown liquid. The liquid was purified by silica gel column chromatography using hexane as the developing solvent and then concentrated, and acetonitrile was added to the obtained liquid to obtain a solid. The solid was recrystallized once using acetonitrile and toluene and once using dichloromethane and methanol, and then dried under reduced pressure to obtain compound 1 represented by the following formula (29.29 g).

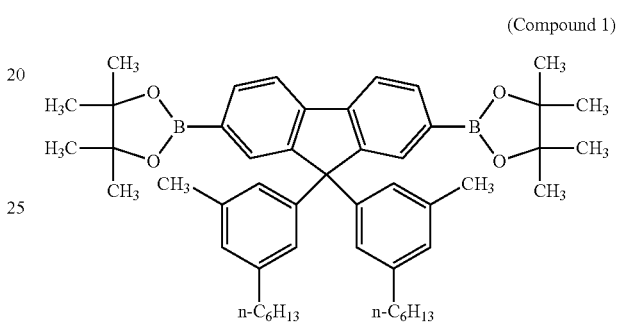

(Compound 1)

Synthesis Example 5

Synthesis of Compound 2-1

A solution comprising 1-bromohexane (13.6 g, 80 mmol) and cyclopentyl methyl ether (40 mL) was slowly added dropwise to a mixture of metal magnesium (1.93 g, 79 mmol) and cyclopentyl methyl ether (41 mL) at 40° C. under an argon atmosphere, and the mixture was stirred. Next, the remaining solution was added dropwise at 50° C. to 56° C. over a period of 50 minutes, and the mixture was stirred at 50° C. for 2 hours to prepare mixture A.

Mixture A was added dropwise to a mixture of 1,3,5-tribromobenzene (5.04 g, 16.0 mmol), cyclopentyl methyl ether (45 mL) and a 1,1-bis(diphenylphosphino)ferrocene-dichloropalladium(II)-dichloromethane complex (Pd(dppf).CH$_2$Cl$_2$, 32.7 mg) over a period of 30 minutes at 40° C. to 45° C. under an argon atmosphere, and the mixture was stirred at 40° C. for 5 hours.

Next, the reaction mixture was cooled to 0° C., 1 M hydrochloric acid was added and the mixture was stirred and allowed to stand, and the obtained aqueous layer was removed from the organic layer. The organic layer was rinsed with water (80 mL), a saturated sodium hydrogencarbonate aqueous solution (80 mL) and water (80 mL), and then anhydrous magnesium sulfate was added, and the mixture was stirred and filtered to obtain a filtrate which was concentrated under reduced pressure to obtain a crude product. The crude product was dissolved in toluene (5 mL) and subjected to silica gel column chromatography to obtain 5.5 g of the target 1-bromo-3,5-di-n-hexylbenzene (compound 2-1 represented by the following formula) (as a mixture with by-products).

(Compound 2-1)

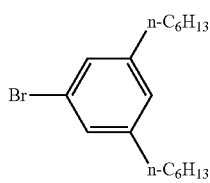

Synthesis Example 6

Synthesis of Compound 2-2

After charging 1-bromo-3,5-di-n-hexylbenzene (compound 2-1, 200 g, 0.69 mol) and tetrahydrofuran (157 g) into a reactor under an argon stream and preparing a homogeneous solution, the solution was further cooled to −69° C. After then adding a 2.76 M n-butyllithium hexane solution (154 g, 0.607 mol) dropwise to the solution at −68° C. over a period of 1.5 hours, the mixture was further stirred at −70° C. for 1.5 hours. Next, a solution comprising 2-methoxycarbonyl-4,4'-dibromobiphenyl (89.9 g, 0.242 mol) and tetrahydrofuran (158 g) was added dropwise at −70° C. over a period of 1 hour and stirred at −70° C. for 2 hours. Methanol (60 mL) and distilled water (60 mL) were then added at −70° C. and stirred therewith, after which the temperature was raised to room temperature and the mixture was stirred overnight at room temperature. Next, the reaction mixture was filtered, the filtrate was concentrated, heptane (400 mL) and water (20 mL) were added, the mixture was stirred and allowed to stand, and the aqueous layer was removed from the separated organic layer. Brine (100 mL) was added to the organic layer, the mixture was stirred and allowed to stand, and the aqueous layer was removed from the separated organic layer. Magnesium sulfate (approximately 30 g) was added to the organic layer, the mixture was stirred and filtered, and the obtained filtrate was concentrated to obtain 234 g of the target compound 2-2 represented by the following formula.

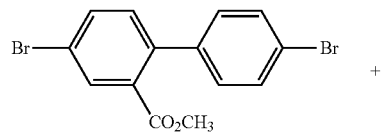

+

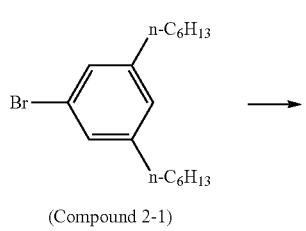

(Compound 2-1)

-continued

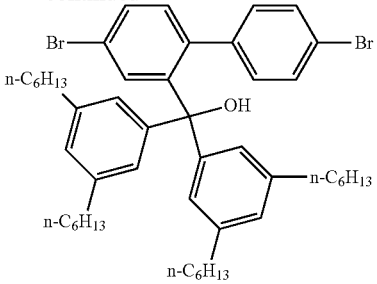

(Compound 2-2)

Synthesis Example 7

Synthesis of Compound 2-3

Compound 2-2 (480 g, 0.497 mol) and dichloromethane (124 g) were charged into a reactor under an argon stream, and a homogeneous solution was prepared and cooled to −30° C. A boron trifluoride-diethyl ether complex ($BF_3 \cdot OEt_2$, 71.1 g, 0.501 mol) was added dropwise to the solution over a period of 30 minutes. The mixture was then stirred overnight at room temperature. The reaction mixture was cooled to −20° C. and distilled water (101 g) was added and stirred therewith for 1 hour, after which the mixture was allowed to stand and the separated aqueous layer was removed from the organic layer. Water (500 mL) was then added, the mixture was stirred and allowed to stand, and the separated aqueous layer was removed from the organic layer. A 10 wt % sodium hydrogencarbonate aqueous solution (200 mL) was added to the obtained organic layer, the mixture was stirred and allowed to stand, and the separated aqueous layer was removed from the organic layer. The organic layer was concentrated to remove the solvent. It was then purified by silica gel column chromatography using toluene and heptane as the developing solvents, and concentrated to remove the solvents. Next, butyl acetate and methanol were used for recrystallization to obtain 232 g of the target compound 2-3 represented by the following formula.

(Compound 2-3)

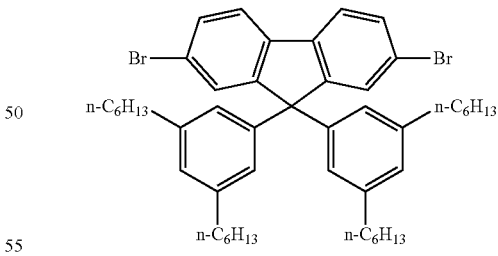

Synthesis Example 8

Synthesis of Compound 2

After charging compound 2-3 (95.2 g, 117 mmol), bis(pinacolato)diboron (65.7 g, 259 mmol), 1,4-dioxane (900 mL), potassium acetate (70.5 g, 718 mmol), 1,1'-bis(diphenylphosphino)ferrocene (dppf, 1.00 g, 1.80 mmol) and 1,1'-bis(diphenylphosphino)ferrocene-dichloropalladium(II)-methylene chloride complex ($PdCl_2dppf \cdot CH_2Cl_2$, 1.53 g, 1.77 mmol) into a 2 L four-necked flask under an argon stream, the mixture was stirred at 100° C. to 102° C. for 5 hours.

Next, the obtained reaction mixture was cooled to room temperature and then filtered with a filter packed with Celite (100 g) and silica gel (100 g), and the obtained filtrate was concentrated to remove the solvent. To a solution prepared by adding hexane (900 mL) there was added active carbon (38.4 g), and the mixture was stirred for 1 hour at the reflux temperature for hexane. After cooling to room temperature, it was filtered with a filter packed with Celite, and concentrated to remove the solvent. Recrystallization was then performed using toluene and acetonitrile, to obtain 101 g of the target compound 2 represented by the following formula.

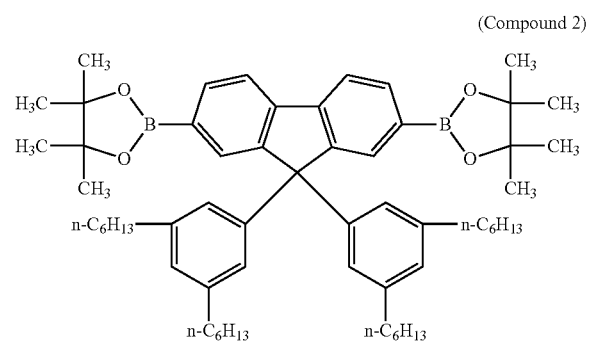

(Compound 2)

Comparative Example 1

Synthesis of Polymer Compound 1

After mixing compound 3-1 represented by the following formula (3.1502 g, 5.94 mmol), compound 3 represented by the following formula (2.9615 g, 5.40 mmol), compound 4 represented by the following formula (0.4431 g, 0.60 mmol), dichlorobis(triphenylphosphine)palladium (4.3 mg), trioctylmethylammonium chloride (trade name: Aliquat336 (product of Aldrich Co.), 0.79 g) and toluene (60 ml) under an inert atmosphere, the mixture was heated to 105° C.

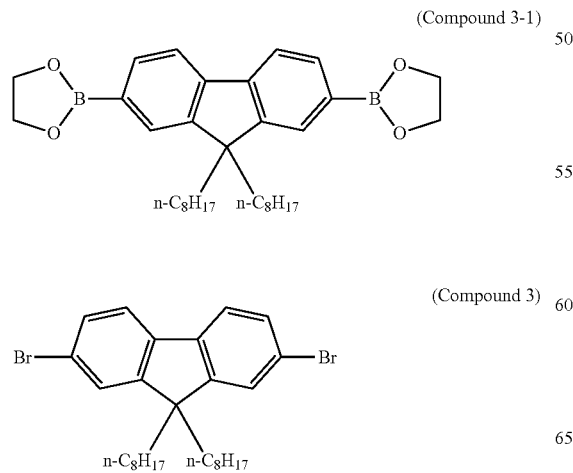

(Compound 3-1)

(Compound 3)

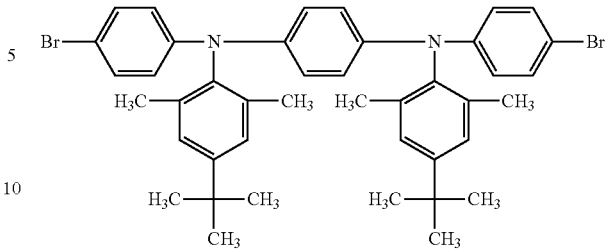

(Compound 4)

To the reaction solution there was added dropwise 2M aqueous sodium carbonate (16.3 ml), and the mixture was refluxed for 3 hours and 10 minutes. After the reaction, phenylboric acid (73 mg), dichlorobis(triphenylphosphine)palladium (4.1 mg) and toluene (60 mL) were added and reflux was continued for 15.5 hours. Next, an aqueous sodium diethyldithiacarbamate solution was added and the mixture was stirred at 80° C. for 2 hours. After cooling, the organic layer was washed twice with water (78 ml), twice with a 3 wt % acetic acid aqueous solution (78 ml) and twice with water (78 ml), and the obtained solution was added dropwise to methanol (1500 mL) and filtered to obtain a precipitate.

The precipitate was dissolved in toluene (190 mL) and passed through an alumina column and a silica gel column in that order for purification. The obtained solution was added dropwise to methanol (930 ml) and stirred, and then the resulting precipitate was filtered and dried to obtain 3.61 g of polymer compound 1. The polystyrene-equivalent number-average molecular weight of polymer compound 1 was $1.0 \times 10^5$, and the polystyrene-equivalent weight-average molecular weight was $2.3 \times 10^5$.

Polymer compound 1 is a random copolymer comprising a constitutional unit represented by the following formula (1a) and a constitutional unit represented by the following formula (1b) in a molar ratio of 95:5, as the theoretical value calculated from the amounts of charged starting materials.

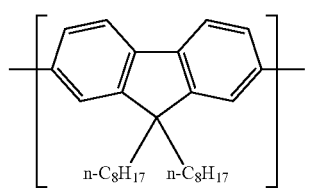

(1a)

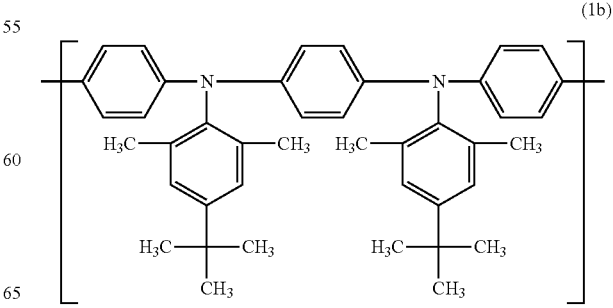

(1b)

Example 1

Synthesis of Polymer Compound 2

After combining compound 1 (1.5181 g, 1.98 mmol), compound 3 (0.9872 g, 1.80 mmol), compound 4 (0.1477 g, 0.20 mmol), dichlorobis(triphenylphosphine)palladium (1.4 mg) and toluene (47 ml) under an inert atmosphere, the mixture was heated to 105° C.

A 20 wt % tetraethylammonium hydroxide aqueous solution (7 ml) was added dropwise to the reaction solution, which was then refluxed for 2 hours. After the reaction, phenylboric acid (24 mg) and dichlorobis(triphenylphosphine) palladium (1.4 mg) were added and reflux was continued for 19 hours. Next, an aqueous sodium diethyldithiacarbamate solution was added and the mixture was stirred at 80° C. for 2 hours. After cooling, washing was performed twice with water (26 ml), twice with a 3 wt % acetic acid aqueous solution (26 ml) and twice with water (26 ml), and the obtained solution was added dropwise to methanol (310 mL) and filtered to obtain a precipitate.

The precipitate was dissolved in toluene (62 mL) and passed through an alumina column and a silica gel column in that order for purification. The obtained solution was added dropwise to methanol (310 ml) and stirred, and then the resulting precipitate was filtered and dried to obtain 1.37 g of polymer compound 2. The polystyrene-equivalent number-average molecular weight of polymer compound 2 was $1.8 \times 10^5$, and the polystyrene-equivalent weight-average molecular weight was $4.3 \times 10^5$.

Polymer compound 2 is a random copolymer comprising a constitutional unit represented by the following formula (2a), a constitutional unit represented by the following formula (2b) and a constitutional unit represented by the following formula (2c) in a molar ratio of 50:45:5, as the theoretical value calculated from the amounts of the charged starting materials.

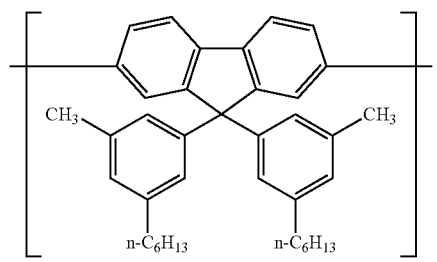
(2a)

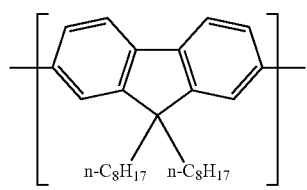
(2b)

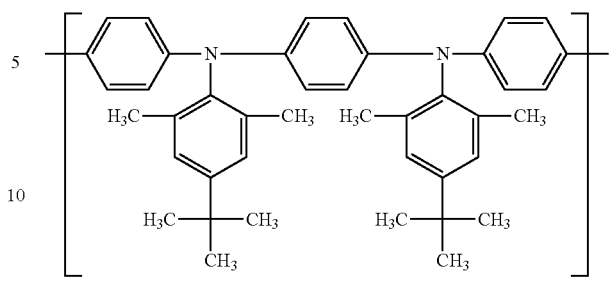
(2c)

Synthesis Example 9

Synthesis of Polymer Compound 3

After combining compound 5 represented by the following formula (1.983 g, 3.98 mmol), compound 6 represented by the following formula (1.561 g, 3.40 mmol), compound 7 represented by the following formula (0.258 g, 0.60 mmol), dichlorobis(triphenylphosphine)palladium (2.8 mg) and toluene (44 ml) under an inert atmosphere, the mixture was heated to 105° C.

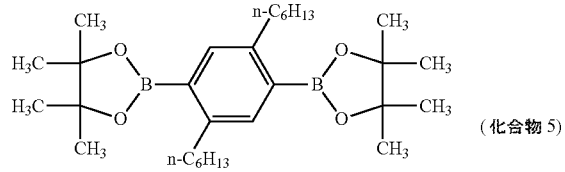
(化合物 5)

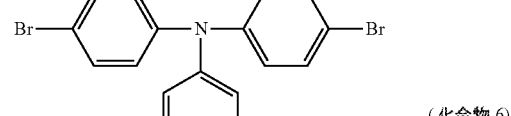
(化合物 6)

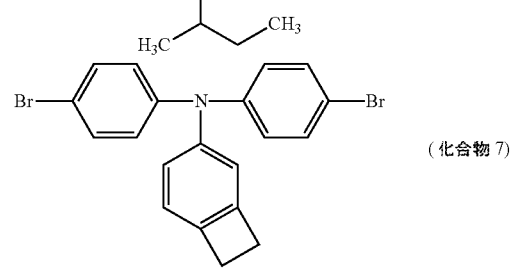
(化合物 7)

A 20 wt % tetraethylammonium hydroxide aqueous solution (13.3 ml) was added dropwise to the reaction solution, which was then refluxed for 12 hours. After the reaction, phenylboric acid (49 mg), dichlorobis(triphenylphosphine) palladium (2.8 mg) and toluene (44 mL) were added and reflux was continued for 17 hours. Next, an aqueous sodium diethyldithiacarbamate solution was added and the mixture was stirred at 80° C. for 2 hours. After cooling, washing was performed twice with water (52 ml), twice with a 3 wt % acetic acid aqueous solution (52 ml) and twice with water (52 ml), and the obtained solution was added dropwise to methanol (620 mL) and filtered to obtain a precipitate.

The precipitate was dissolved in toluene (124 mL) and passed through an alumina column and a silica gel column in that order for purification. The obtained solution was added dropwise to methanol (620 ml) and stirred, and then the resulting precipitate was filtered and dried to obtain 1.94 g of polymer compound 3. The polystyrene-equivalent number-average molecular weight of polymer compound 3 was $4.4 \times 10^4$, and the polystyrene-equivalent weight-average molecular weight was $1.1 \times 10^5$.

Polymer compound 3 is a random copolymer comprising a constitutional unit represented by the following formula (3a), a constitutional unit represented by the following formula (3b) and a constitutional unit represented by the following formula (3c) in a molar ratio of 49.9:42.6:7.5, as the theoretical value calculated from the amounts of the charged starting materials.

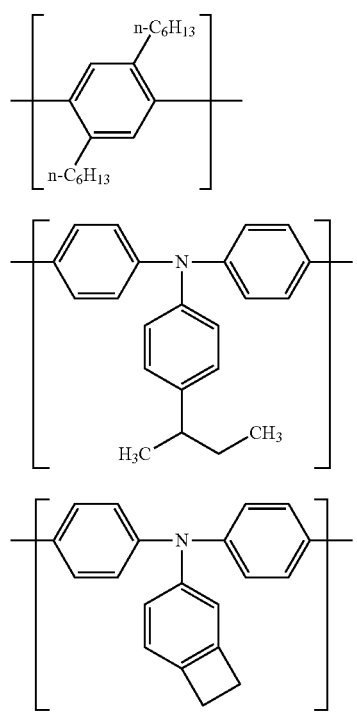

Comparative Example 2

Fabrication and Evaluation of Light-Emitting Device 1

<Formation of Hole Injection Layer>

A composition for formation of a hole injection layer was coated onto a glass panel on which an ITO anode had been formed, and a coating film with a film thickness of 60 nm was obtained by spin coating method. The coating film-formed substrate was heated at 200° C. for 10 minutes, and after insolubilizing the coating film, it was allowed to naturally cool to room temperature to obtain a hole injection layer. The composition used for formation of the hole injection layer was a PEDOT:PSS aqueous solution (poly(3,4-ethylenedioxythiophene):polystyrenesulfonic acid, product name: Baytron), available from Starck-V Tech.

<Formation of Hole Transport Layer>

Polymer compound 3 and xylene were combined to a polymer compound 3 concentration of 0.7 wt %, to obtain a composition for formation of a hole transport layer. The hole injection layer was coated with the composition for formation of a hole transport layer by spin coating method, to obtain a coating film with a thickness of 20 nm. The coating film-formed substrate was heated at 180° C. for 60 minutes, and after insolubilizing the coating film, it was allowed to naturally cool to room temperature to obtain a hole transport layer.

<Formation of Light-Emitting Layer>

Polymer compound 1 and xylene were combined to a polymer compound 1 concentration of 1.3 wt %, to obtain a composition for formation of a light-emitting layer. The hole transport layer of the obtained substrate, which comprised an anode, hole injection layer and hole transport layer, was coated with the composition for formation of a light-emitting layer by spin coating method to obtain a coating film with a thickness of 60 nm. The coating film-formed substrate was heated at 130° C. for 20 minutes, and after evaporating off the solvent, it was allowed to naturally cool to room temperature to obtain a light-emitting layer.

<Formation of Cathode>

The light-emitting layer of the obtained substrate, which comprised an anode, hole injection layer, hole transport layer and light-emitting layer, was subjected to vacuum vapor deposition method to continuously form a barium layer with a thickness of 5 nm and then an aluminum layer with a thickness of 80 nm, thereby forming a cathode.

<Sealing>

The obtained substrate having such a multilayer structure was removed from the vacuum vapor deposition apparatus and was sealed with sealing glass and a two-pack mixture epoxy resin under a nitrogen atmosphere, to obtain light-emitting device 1.

<Evaluation>

Blue electroluminescence (EL) was observed when a voltage was applied to the light-emitting device 1. The maximum current efficiency of the light-emitting device 1 was 7.3 cd/A, and the maximum external quantum yield was 6.8%. Also, the luminance half-life, which is the time from the initial luminance of 3400 cd/m$^2$ to half-luminance, was 1.7 hours.

Example 2

Fabrication and Evaluation of Light-Emitting Device 2

<Fabrication of Light-Emitting Device 2>

Light-emitting device 2 was fabricated in the same manner as Comparative Example 2, except that polymer compound 2 was used instead of polymer compound 1 in Comparative Example 2.

<Evaluation>

Blue electroluminescence (EL) was observed when a voltage was applied to the light-emitting device 2. The maximum current efficiency of light-emitting device 2 was 9.3 cd/A, and the maximum external quantum yield was 8.3%. A voltage was applied for the same number of emitted photons as Comparative Example 2, and the luminance half-life, as the time from the initial luminance of 3500 cd/m$^2$ to half-luminance, was measured to be 4.2 hours.

Synthesis Example 10

Synthesis of Polymer Compound 4

After mixing compound 3-1 (3.863 g, 7.283 mmol), compound 6 (3.177 g, 6.919 mmol) and compound 7 (0.1563 g, 0.364 mmol), trioctylmethylammonium chloride (trade name: Aliquat336 (product of Aldrich Co.), 3.1 mL), dichlorobis(triphenylphosphine)palladium (4.9 mg) and toluene (50 ml) under an inert atmosphere, the mixture was heated to 105° C.

Next, aqueous sodium carbonate (2.0 M, 14 mL) was added to the reaction solution, which was refluxed for 16.5 hours. Phenylboric acid (0.5 g) was added and reflux was continued for 7 hours. Water (50 mL) was added to the organic layer obtained by removing the aqueous layer, the mixture was stirred and allowed to stand, and the separated aqueous layer was removed. Sodium diethyldithiocarbamate (0.75 g) and water (50 mL) were added to the obtained organic layer, and the mixture was stirred at 85° C. for 16 hours. The obtained reaction mixture was allowed to stand, the separated aqueous layer was removed, the remaining organic layer was rinsed 3 times with water (100 mL), and the obtained solution was passed through a silica gel and basic alumina column. The obtained solution was added dropwise to methanol and stirred, and then the resulting precipitate was filtered and dried to obtain 4.2 g of polymer compound 4. The polystyrene-equivalent number-average molecular weight of polymer compound 4 was $4.4 \times 10^4$, and the polystyrene-equivalent weight-average molecular weight was $1.2 \times 10^5$.

Polymer compound 4 is a random copolymer comprising a constitutional unit represented by the following formula (4a), a constitutional unit represented by the following formula (4b) and a constitutional unit represented by the following formula (4c) in a molar ratio of 50.0:42.5:7.5, as the theoretical value calculated from the amounts of the charged starting materials.

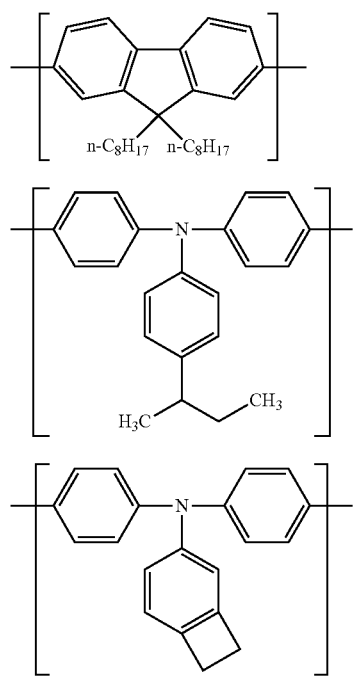

Comparative Example 3

Fabrication and Evaluation of Light-Emitting Device 3

<Fabrication of Light-Emitting Device 3>
Light-emitting device 3 was fabricated in the same manner as Comparative Example 2, except that polymer compound 4 was used instead of polymer compound 3 in Comparative Example 2.

<Evaluation>
Blue electroluminescence (EL) was observed when a voltage was applied to the light-emitting device 3. The maximum current efficiency of light-emitting device 3 was 7.4 cd/A, and the maximum external quantum yield was 5.2%. Also, the luminance half-life, which is the time from the initial luminance of 4500 cd/m$^2$ to half-luminance, was measured to be 6.6 hours.

Example 3

Fabrication of Light-Emitting Device 4

<Fabrication of Light-Emitting Device 4>
Light-emitting device 4 was fabricated in the same manner as Comparative Example 2, except that polymer compound 2 was used instead of polymer compound 1 and polymer compound 4 was used instead of polymer compound 3 in Comparative Example 2.

<Evaluation>
Blue electroluminescence (EL) was observed when a voltage was applied to the light-emitting device 4. The maximum current efficiency of light-emitting device 4 was 8.2 cd/A, and the maximum external quantum yield was 5.8%. A voltage was applied for the same number of emitted photons as Comparative Example 3, and the luminance half-life, as the time from the initial luminance of 4500 cd/m$^2$ to half-luminance, was measured to be 52.6 hours.

Example 4

Synthesis of Polymer Compound 5

After combining compound 2 (2.6798 g, 2.95 mmol), compound 3 (1.4808 g, 2.70 mmol), compound 4 (0.2215 g, 0.30 mmol), dichlorobis(triphenylphosphine)palladium (2.16 mg) and toluene (70 ml) under an inert atmosphere, the mixture was heated to 105° C.

A 20 wt % tetraethylammonium hydroxide aqueous solution (10 ml) was added dropwise to the reaction solution, which was then refluxed for 3 hours. After the reaction, phenylboric acid (36.5 mg) and dichlorobis(triphenylphosphine) palladium (2.11 mg) were added and reflux was continued for 23 hours. Next, an aqueous sodium diethyldithiacarbamate solution was added and the mixture was stirred at 80° C. for 2 hours. After cooling, washing was performed twice with water (40 ml), twice with a 3 wt % acetic acid aqueous solution (40 nil) and twice with water (40 ml), and the obtained solution was added dropwise to methanol (500 mL) and filtered to obtain a precipitate.

The precipitate was dissolved in toluene (100 mL) and passed through an alumina column and a silica gel column in that order for purification. The obtained solution was added dropwise to methanol (500 ml) and stirred, and then the resulting precipitate was filtered and dried to obtain 2.45 g of polymer compound 5. The polystyrene-equivalent number-average molecular weight of polymer compound 5 was $8.3 \times 10^4$, and the polystyrene-equivalent weight-average molecular weight was $2.3 \times 10^5$.

Polymer compound 5 is a random copolymer comprising a constitutional unit represented by the following formula (5a), a constitutional unit represented by the following formula (5b) and a constitutional unit represented by the following formula (5c) in a molar ratio of 50:45:5, as the theoretical value calculated from the amounts of the charged starting materials.

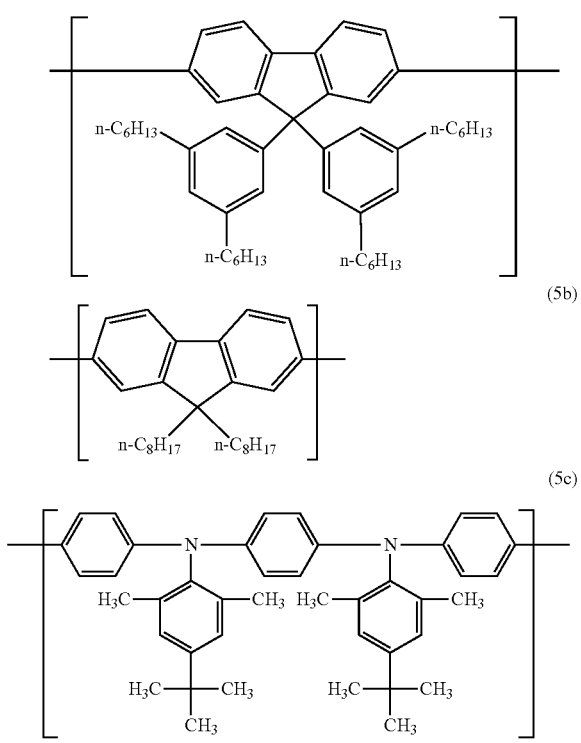

(5a)

(5b)

(5c)

Comparative Example 4

Fabrication and Evaluation of Light-Emitting Device 5

<Fabrication of Light-Emitting Device 5>

Light-emitting device 5 was fabricated in the same manner as Comparative Example 2, except that the thickness of the hole injection layer was 50 nm instead of 60 nm in Comparative Example 2, and polymer compound 4 was used instead of polymer compound 3.

<Evaluation>

Blue electroluminescence (EL) was observed when a voltage was applied to the light-emitting device 5. The maximum current efficiency of light-emitting device 5 was 6.5 cd/A, and the maximum external quantum yield was 4.6%. Also, the luminance half-life, which is the time from the initial luminance of 4030 cd/m² to half-luminance, was measured to be 8.8 hours.

Example 5

Fabrication and Evaluation of Light-Emitting Device 6

<Fabrication of Light-Emitting Device 6>

Light-emitting device 6 was fabricated in the same manner as Comparative Example 2, except that the thickness of the hole injection layer was 50 nm instead of 60 nm in Comparative Example 2, polymer compound 5 was used instead of polymer compound 1, and polymer compound 4 was used instead of polymer compound 3.

<Evaluation>

Blue electroluminescence (EL) was observed when a voltage was applied to the light-emitting device 6. The maximum current efficiency of light-emitting device 6 was 8.4 cd/A, and the maximum external quantum yield was 6.3%. A voltage was applied for the same number of emitted photons as Comparative Example 4, and the luminance half-life, as the time from the initial luminance of 3755 cd/m² to half-luminance, was measured to be 21.1 hours.

Comparative Example 5

Synthesis of Polymer Compound 6

After combining compound 3-2 represented by the following formula (1.9065 g, 2.97 mmol), compound 3 (1.4808 g, 2.70 mmol), compound 8 represented by the following formula (0.1420 g, 0.30 mmol), dichlorobis(triphenylphosphine)palladium (2.11 mg) and toluene (71 ml) under an inert atmosphere, the mixture was heated to 105° C.

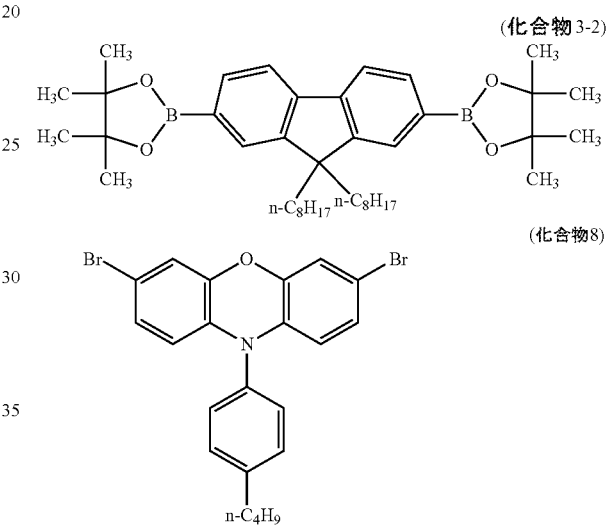

(化合物 3-2)

(化合物 8)

A 20 wt % tetraethylammonium hydroxide aqueous solution (10 ml) was added dropwise to the reaction solution, which was then refluxed for 3 hours. After the reaction, phenylboric acid (37 mg) and dichlorobis(triphenylphosphine)palladium (2.11 mg) were added and reflux was continued for 17 hours. Next, an aqueous sodium diethyldithiacarbamate solution was added and the mixture was stirred at 80° C. for 2 hours. After cooling, washing was performed twice with water (39 ml), twice with a 3 wt % acetic acid aqueous solution (39 ml) and twice with water (39 ml), and the obtained solution was added dropwise to methanol (500 mL) and filtered to obtain a precipitate.

The precipitate was dissolved in toluene (94 mL) and passed through an alumina column and a silica gel column in that order for purification. The obtained solution was added dropwise to methanol (325 ml) and stirred, and then the resulting precipitate was filtered and dried to obtain 1.77 g of polymer compound 6. The polystyrene-equivalent number-average molecular weight of polymer compound 6 was $1.1 \times 10^5$, and the polystyrene-equivalent weight-average molecular weight was $3.5 \times 10^5$.

Polymer compound 6 is a random copolymer comprising a constitutional unit represented by the following formula (6a) and a constitutional unit represented by the following formula (6b) in a molar ratio of 95:5, as the theoretical value calculated from the amounts of charged starting materials.

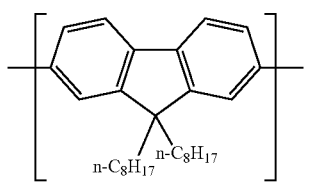
(6a)

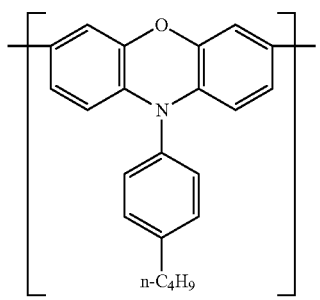
(6b)

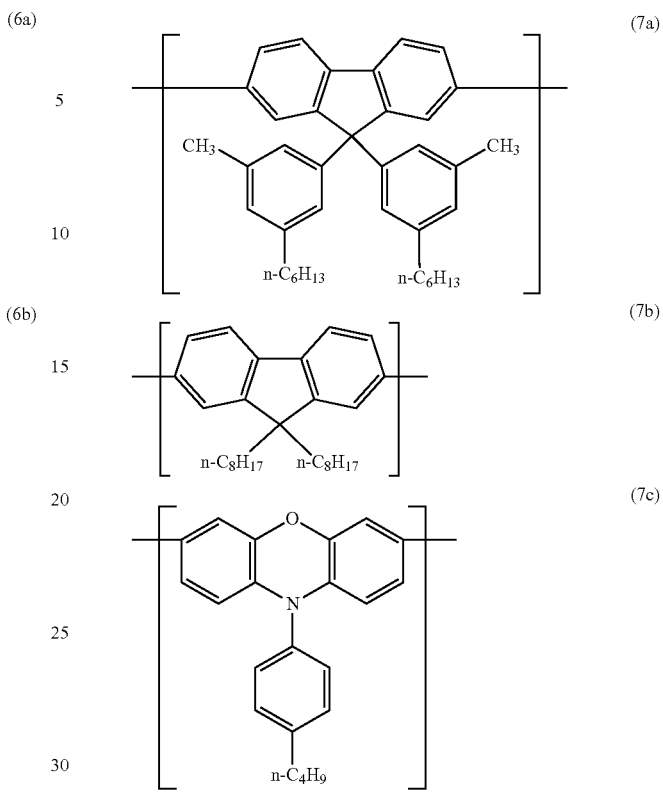

Example 6

Synthesis of Polymer Compound 7

After combining compound 1 (1.5181 g, 1.98 mmol), compound 3 (0.9872 g, 1.80 mmol), compound 8 (0.0946 g, 0.20 mmol), dichlorobis(triphenylphosphine)palladium (1.3 mg) and toluene (47 ml) under an inert atmosphere, the mixture was heated to 105° C.

A 20 wt % tetraethylammonium hydroxide aqueous solution (8 ml) was added dropwise to the reaction solution, which was then refluxed for 1 hour and 45 minutes. After the reaction, phenylboric acid (25 mg) and dichlorobis(triphenylphosphine)palladium (1.2 mg) were added and reflux was continued for 19 hours. Next, an aqueous sodium diethyldithiacarbamate solution was added and the mixture was stirred at 80° C. for 2 hours. After cooling, washing was performed twice with water (26 ml), twice with a 3 wt % acetic acid aqueous solution (26 ml) and twice with water (26 ml), and the obtained solution was added dropwise to methanol (310 mL) and filtered to obtain a precipitate.

The precipitate was dissolved in toluene (62 mL) and passed through an alumina column and a silica gel column in that order for purification. The obtained solution was added dropwise to methanol (310 ml) and stirred, and then the resulting precipitate was filtered and dried to obtain 1.53 g of polymer compound 7. The polystyrene-equivalent number-average molecular weight of polymer compound 7 was $1.9 \times 10^5$, and the polystyrene-equivalent weight-average molecular weight was $5.1 \times 10^5$.

Polymer compound 7 is a random copolymer comprising a constitutional unit represented by the following formula (7a), a constitutional unit represented by the following formula (7b) and a constitutional unit represented by the following formula (7c) in a molar ratio of 50:45:5, as the theoretical value calculated from the amounts of the charged starting materials.

Comparative Example 6

Fabrication and Evaluation of Light-Emitting Device 7

<Fabrication of Light-Emitting Device 7>
Light-emitting device 7 was fabricated in the same manner as Comparative Example 2, except that the thickness of the hole injection layer was 50 nm instead of 60 nm in Comparative Example 2, polymer compound 6 was used instead of polymer compound 1 and polymer compound 4 was used instead of polymer compound 3.

<Evaluation>
Blue electroluminescence (EL) was observed when a voltage was applied to the light-emitting device 7. The maximum current efficiency of light-emitting device 7 was 6.4 cd/A, and the maximum external quantum yield was 4.8%. Also, the luminance half-life, which is the time from the initial luminance of 3800 cd/m$^2$ to half-luminance, was measured to be 9.3 hours.

Example 7

Fabrication and Evaluation of Light-Emitting Device 8

<Fabrication of Light-Emitting Device 8>
Light-emitting device 8 was fabricated in the same manner as Comparative Example 2, except that the thickness of the hole injection layer was 50 nm instead of 60 nm in Comparative Example 2, polymer compound 7 was used instead of polymer compound 1, and polymer compound 4 was used instead of polymer compound 3.

<Evaluation>

Blue electroluminescence (EL) was observed when a voltage was applied to the light-emitting device 8. The maximum current efficiency of light-emitting device 8 was 11.3 cd/A, and the maximum external quantum yield was 7.3%. A voltage was applied for the same number of emitted photons as Comparative Example 6, and the luminance half-life, as the time from the initial luminance of 4455 cd/m² to half-luminance, was measured to be 72.0 hours.

Example 8

Fabrication and Evaluation of Light-Emitting Device 9

<Fabrication of Light-Emitting Device 9>

Light-emitting device 9 was fabricated in the same manner as Comparative Example 2, except that polymer compound 7 was used instead of polymer compound 1 and polymer compound 4 was used instead of polymer compound 3 in Comparative Example 2.

<Evaluation>

Blue electroluminescence (EL) was observed when a voltage was applied to the light-emitting device 9. The maximum current efficiency of light-emitting device 9 was 10.9 cd/A, and the maximum external quantum yield was 7.0%. Also, the luminance half-life, which is the time from the initial luminance of 5810 cd/m² to half-luminance, was measured to be 38.1 hours.

Comparative Example 7

Synthesis of Polymer Compound 8

After combining compound 3-2 (1.9181 g, 2.99 mmol), compound 3 (0.4112 g, 0.75 mmol), compound 9 represented by the following formula (1.6395 g, 1.80 mmol), compound 10 represented by the following formula (0.2422 g, 0.46 mmol), dichlorobis(triphenylphosphine)palladium (2.1 mg) and toluene (70 ml) under an inert atmosphere, the mixture was heated to 105° C.

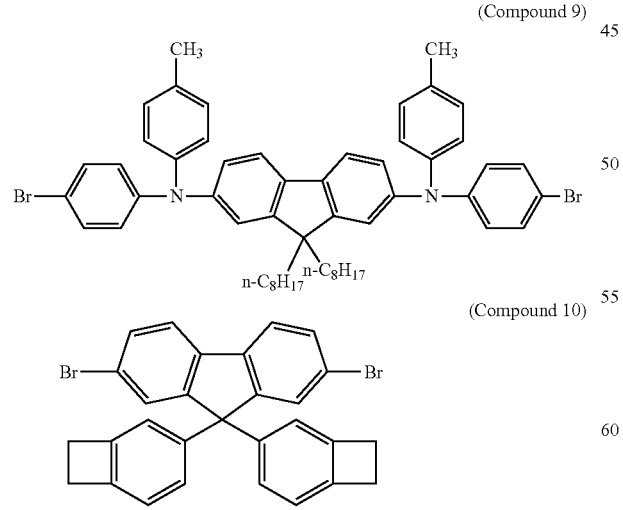

A 20 wt % tetraethylammonium hydroxide aqueous solution (10 ml) was added dropwise to the reaction solution, which was then refluxed for 8 hours. After the reaction, phenylboric acid (36.7 mg) and dichlorobis(triphenylphosphine)palladium (2.2 mg) were added and reflux was continued for 16 hours. Next, an aqueous sodium diethyldithiacarbamate solution was added and the mixture was stirred at 80° C. for 2 hours. After cooling, washing was performed twice with water (40 ml), twice with a 3 wt % acetic acid aqueous solution (40 ml) and twice with water (40 ml), and the obtained solution was added dropwise to methanol (600 mL) and filtered to obtain a precipitate.

The precipitate was dissolved in toluene (100 mL) and passed through an alumina column and a silica gel column in that order for purification. The obtained solution was added dropwise to methanol (450 ml) and stirred, and then the resulting precipitate was filtered and dried to obtain 2.47 g of polymer compound 8. The polystyrene-equivalent number-average molecular weight of polymer compound 8 was $5.4 \times 10^4$, and the polystyrene-equivalent weight-average molecular weight was $2.1 \times 10^5$.

Polymer compound 8 is a random copolymer comprising a constitutional unit represented by the following formula (8a), a constitutional unit represented by the following formula (8b) and a constitutional unit represented by the following formula (8c) in a molar ratio of 62.5:30:7.5, as the theoretical value calculated from the amounts of the charged starting materials.

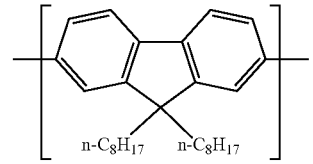

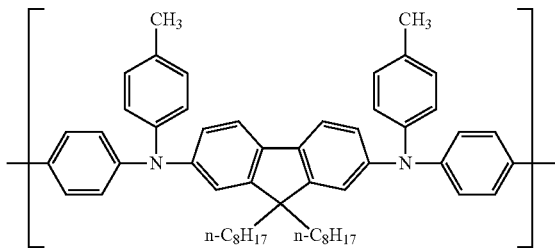

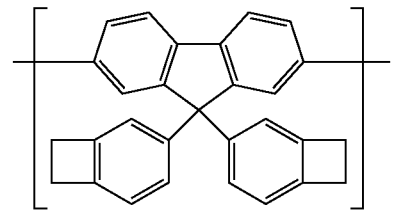

Example 9

Synthesis of Polymer Compound 9

After combining compound 2 (2.6882 g, 2.96 mmol), compound 3 (0.4245 g, 0.75 mmol), compound 9 (1.6396 g, 1.80 mmol), compound 10 (0.2377 g, 0.45 mmol), dichlorobis(triphenylphosphine)palladium (2.1 mg) and toluene (62 ml) under an inert atmosphere, the mixture was heated to 105° C.

A 20 wt % tetraethylammonium hydroxide aqueous solution (10 ml) was added dropwise to the reaction solution, which was then refluxed for 4.5 hours. After the reaction, phenylboric acid (36.8 mg) and dichlorobis(triphenylphosphine)palladium (2.1 mg) were added and reflux was continued for 16.5 hours. Next, an aqueous sodium diethyldithiacarbamate solution was added and the mixture was stirred at 80° C. for 2 hours. After cooling, washing was performed twice with water (40 ml), twice with a 3 wt % acetic acid aqueous solution (40 ml) and twice with water (40 ml), and the obtained solution was added dropwise to methanol (500 mL) and filtered to obtain a precipitate.

The precipitate was dissolved in toluene (100 mL) and passed through an alumina column and a silica gel column in that order for purification. The obtained solution was added dropwise to methanol (500 ml) and stirred, and then the resulting precipitate was filtered and dried to obtain 3.12 g of polymer compound 9. The polystyrene-equivalent number-average molecular weight of polymer compound 9 was $7.8 \times 10^4$, and the polystyrene-equivalent weight-average molecular weight was $2.6 \times 10^5$.

Polymer compound 9 is a random copolymer comprising a constitutional unit represented by the following formula (9a), a constitutional unit represented by the following formula (9b), a constitutional unit represented by the following formula (9c) and a constitutional unit represented by the following formula (9d), in a molar ratio of 50:12.5:30:7.5, as the theoretical value calculated from the charged starting materials.

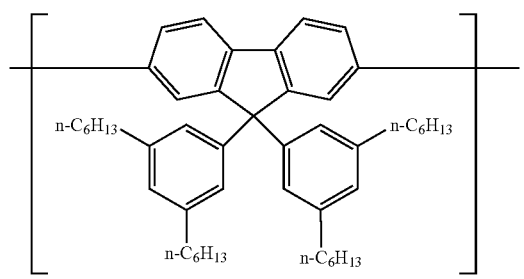

(9a)

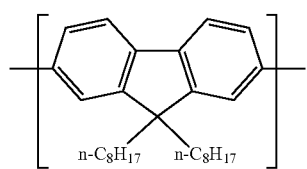

(9b)

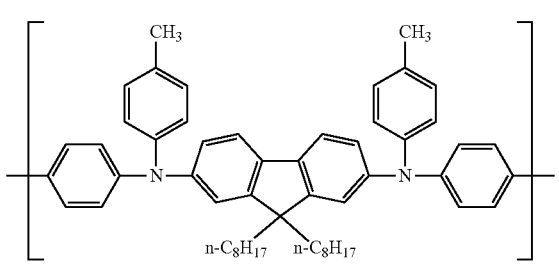

(9c)

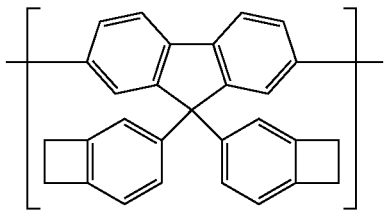

(9d)

Example 10

Synthesis of Polymer Compound 10

After combining compound 2 (7.2119 g, 7.95 mmol), compound 3 (1.0970 g, 2.00 mmol), compound 11 represented by the following formula (3.5455 g, 4.80 mmol), compound 10 (0.6340 g, 1.20 mmol), dichlorobis(triphenylphosphine)palladium (5.7 mg) and toluene (190 ml) under an inert atmosphere, the mixture was heated to 105° C.

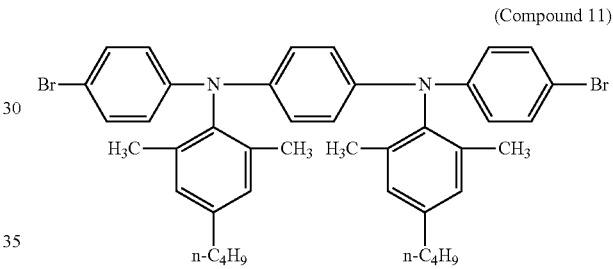

(Compound 11)

A 20 wt % tetraethylammonium hydroxide aqueous solution (27 ml) was added dropwise to the reaction solution, which was then refluxed for 3 hours. After the reaction, phenylboric acid (97.6 mg) and dichlorobis(triphenylphosphine) palladium (5.7 mg) were added and reflux was continued for 15 hours. Next, an aqueous sodium diethyldithiacarbamate solution was added and the mixture was stirred at 80° C. for 2 hours. After cooling, washing was performed twice with water (104 ml), twice with a 3 wt % acetic acid aqueous solution (104 ml) and twice with water (104 ml), and the obtained solution was added dropwise to methanol (1243 mL) and filtered to obtain a precipitate.

The precipitate was dissolved in toluene (351 mL) and passed through an alumina column and a silica gel column in that order for purification. The obtained solution was added dropwise to methanol (1243 ml) and stirred, and then the resulting precipitate was filtered and dried to obtain 6.42 g of polymer compound 10. The polystyrene-equivalent number-average molecular weight of polymer compound 10 was $8.5 \times 10^4$, and the polystyrene-equivalent weight-average molecular weight was $2.9 \times 10^5$.

Polymer compound 10 is a random copolymer comprising a constitutional unit represented by the following formula (10a), a constitutional unit represented by the following formula (10b), a constitutional unit represented by the following formula (10c) and a constitutional unit represented by the following formula (10d), in a molar ratio of 50:12.5:30:7.5, as the theoretical value calculated from the charged starting materials.

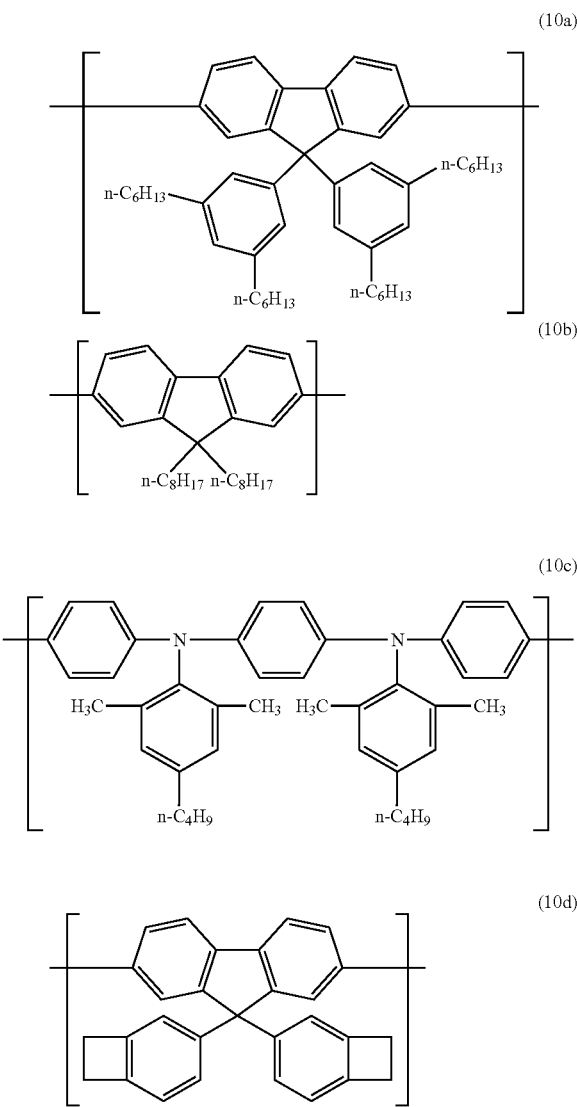

(10a)
(10b)
(10c)
(10d)

Example 11

Fabrication and Evaluation of Light-Emitting Device 10

<Fabrication of Light-Emitting Device 10>

Light-emitting device 10 was fabricated in the same manner as Comparative Example 2, except that the thickness of the hole injection layer was 50 nm instead of 60 nm in Comparative Example 2, polymer compound 2 was used instead of polymer compound 1 and polymer compound 8 was used instead of polymer compound 3.

<Evaluation>

Blue electroluminescence (EL) was observed when a voltage was applied to the light-emitting device 10. The maximum current efficiency of light-emitting device 10 was 6.4 cd/A, and the maximum external quantum yield was 5.2%. Also, the luminance life, as the time from the initial luminance of 3460 cd/m$^2$ to 55% luminance, was measured to be 72.5 hours.

Example 12

Fabrication and Evaluation of Light-Emitting Device 11

<Fabrication of Light-Emitting Device 11>

Light-emitting device 11 was fabricated in the same manner as Comparative Example 2, except that the thickness of the hole injection layer was 50 nm instead of 60 nm in Comparative Example 2, polymer compound 2 was used instead of polymer compound 1 and polymer compound 9 was used instead of polymer compound 3.

<Evaluation>

Blue electroluminescence (EL) was observed when a voltage was applied to the light-emitting device 11. The maximum current efficiency of light-emitting device 11 was 6.1 cd/A, and the maximum external quantum yield was 5.2%. A voltage was applied for the same number of emitted photons as Comparative Example 11, and the luminance life, as the time from the initial luminance of 3320 cd/m$^2$ to 55% luminance, was measured to be 86.5 hours.

Example 13

Fabrication and Evaluation of Light-Emitting Device 12

<Fabrication of Light-Emitting Device 12>

Light-emitting device 12 was fabricated in the same manner as Comparative Example 2, except that the thickness of the hole injection layer was 50 nm instead of 60 nm in Comparative Example 2, polymer compound 2 was used instead of polymer compound 1 and polymer compound 10 was used instead of polymer compound 3.

<Evaluation>

Blue electroluminescence (EL) was observed when a voltage was applied to the light-emitting device 12. The maximum current efficiency of light-emitting device 12 was 6.4 cd/A, and the maximum external quantum yield was 5.5%. A voltage was applied for the same number of emitted photons as Comparative Example 11, and the luminance life, as the time from the initial luminance of 3290 cd/m$^2$ to 55% luminance, was measured to be 148.2 hours.

Example 14

Fabrication and Evaluation of Light-Emitting Device 13

<Formation of Hole Injection Layer>

A composition for formation of a hole injection layer was coated onto a glass panel on which an ITO anode had been formed, and a coating film with a thickness of 50 nm was obtained by spin coating method. The coating film-formed substrate was heated at 200° C. for 10 minutes, and after insolubilizing the coating film, it was allowed to naturally cool to room temperature to obtain a hole injection layer. The composition used for formation of the hole injection layer was a PEDOT:PSS aqueous solution (poly(3,4-ethylenedioxythiophene):polystyrenesulfonic acid, product name: Baytron), available from Starck-V Tech.

<Formation of Hole Transport Layer>

Polymer compound 9 and xylene were combined to a polymer compound 9 concentration of 0.7 wt %, to obtain a composition for formation of a hole transport layer. The hole injection layer was coated with the composition for formation of a hole transport layer by spin coating method, to obtain a coating film with a thickness of 20 nm. The coating film-formed substrate was heated at 180° C. for 60 minutes, and after insolubilizing the coating film, it was allowed to naturally cool to room temperature to obtain a hole transport layer.

<Formation of Light-Emitting Layer>

Polymer compound 1, compound COM-3 represented by the following formula and xylene were combined to a total polymer compound 1/compound COM-3 concentration of 1.3 wt %, to obtain a composition for formation of a light-emitting layer. The mixing was to a weight ratio of 95:5 for polymer compound 1 and compound COM-3. The hole transport layer of the obtained substrate, which comprised an anode, hole injection layer and hole transport layer, was coated with the composition for formation of a light-emitting layer by spin coating method to obtain a coating film with a thickness of 80 nm. The coating film-formed substrate was heated at 130° C. for 20 minutes, and after evaporating off the solvent, it was allowed to naturally cool to room temperature to obtain a light-emitting layer.

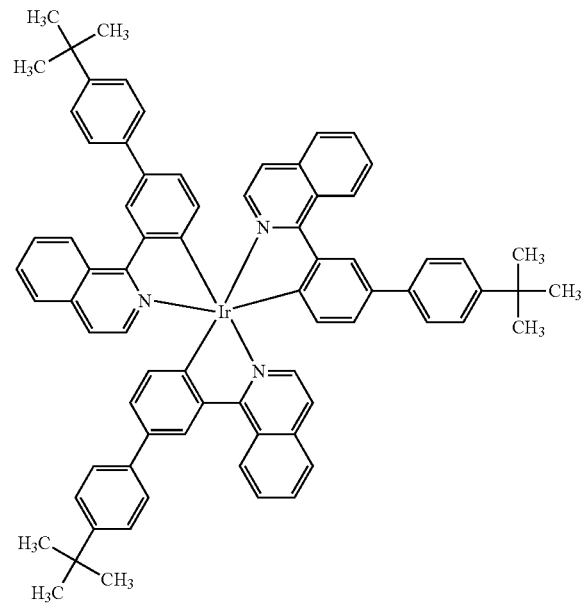

COM-3

<Formation of Cathode>

The light-emitting layer of the obtained substrate, which comprised an anode, hole injection layer, hole transport layer and light-emitting layer, was subjected to vacuum vapor deposition method to continuously form a barium layer with a thickness of 5 nm and then an aluminum layer with a thickness of 80 nm, thereby forming a cathode.

<Sealing>

The obtained substrate having such a multilayer structure was removed from the vacuum vapor deposition apparatus and was sealed with sealing glass and a two-pack mixture epoxy resin under a nitrogen atmosphere, to obtain light-emitting device 13.

<Evaluation>

Red electroluminescence (EL) was observed when a voltage was applied to the light-emitting device 13. The maximum current efficiency of light-emitting device 13 was 7.9 cd/A, and the maximum external quantum yield was 9.4%. Also, the luminance half-life, which is the time from the initial luminance of 12,000 cd/m² to half-luminance, was 13.4 hours.

Example 15

Fabrication and Evaluation of Light-Emitting Device 14

<Fabrication of Light-Emitting Device 14>

Light-emitting device 14 was fabricated in the same manner as Example 14, except that polymer compound 5 was used instead of polymer compound 1 in Example 14.

<Evaluation>

Red electroluminescence (EL) was observed when a voltage was applied to the light-emitting device 14. The maximum current efficiency of light-emitting device 14 was 9.8 cd/A, and the maximum external quantum yield was 11.7%. A voltage was applied for the same number of emitted photons as Example 14, and the luminance half-life, as the time from the initial luminance of 12,000 cd/m² to half-luminance, was 41.9 hours.

EXPLANATION OF SYMBOLS

10: Substrate, 11: anode, 12: hole injection layer, 13: hole transport layer, 14: light-emitting layer, 15: electron transport layer, 16: electron injection layer, 17: cathode, 100, 110: light-emitting devices, 20: substrate, 21: anode, 22: hole injection layer, 23: light-emitting layer, 24: cathode, 25: protective layer, 200: surface light source.

The invention claimed is:

1. A light-emitting device having:
   electrodes consisting of an anode and a cathode, and
   a light emitting layer comprising a polymer compound formed between the electrodes,
   wherein the polymer compound comprises a constitutional unit represented by formula (4), and one or more constitutional units selected from the group consisting of constitutional units represented by formula (6) and constitutional units represented by formula (7);

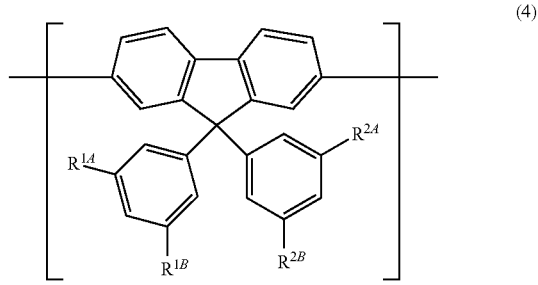

(4)

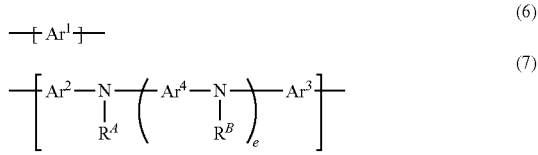

(6)

(7)

in formula (4), $R^{1A}$, $R^{1B}$, $R^{2A}$ and $R^{2B}$ each independently represent a primary unsubstituted alkyl group having 1 to 10 carbon atoms;

in formula (6), $Ar^1$ represents an unsubstituted or substituted arylene group or an unsubstituted or substituted divalent heterocyclic group; this is with the proviso that the constitutional unit represented by formula (6) is a constitutional unit having a different structure from the constitutional unit represented by formula (4);

in formula (7), $Ar^2$, $Ar^3$ and $Ar^4$ each independently represent an unsubstituted or substituted arylene group, an unsubstituted or substituted divalent aromatic heterocyclic group or an unsubstituted or substituted divalent group in which two aromatic rings are linked by a single bond; $R^A$ and $R^B$ each independently represent a hydrogen atom, an unsubstituted or substituted alkyl group, an unsubstituted or substituted aryl group or an unsubstituted or substituted monovalent heterocyclic group; the letter e represents 0 or 1.

2. The light-emitting device according to claim 1, wherein at least one of a combination of $R^{1A}$ and $R^{1B}$ and a combination of $R^{2A}$ and $R^{2B}$ is a combination of mutually differing groups.

3. The light-emitting device according to claim 1, wherein the constitutional unit represented by formula (6) is a constitutional unit represented by formula (8), a constitutional unit represented by formula (9), a constitutional unit represented by formula (10) or a constitutional unit represented by formula (11);

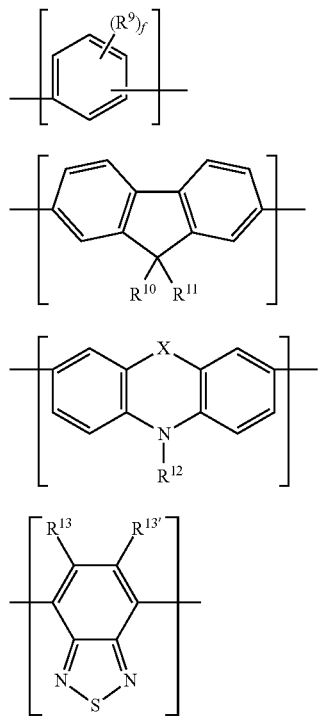

in formula (8), $R^9$ represents an unsubstituted or substituted alkyl group, an unsubstituted or substituted alkoxy group, an unsubstituted or substituted aryl group, an unsubstituted or substituted aryloxy group, an unsubstituted or substituted monovalent heterocyclic group, an unsubstituted or substituted silyl group, a halogen atom, an alkoxycarbonyl group, a carboxyl group or a cyano group; the letter f represents an integer of 0 to 4; when multiple $R^9$ groups are present, they may be the same or different;

in formula (9), $R^{10}$ and $R^{11}$ each independently represent a hydrogen atom, an unsubstituted or substituted alkyl group or an unsubstituted or substituted aryl group; this is with the proviso that the constitutional unit represented by formula (9) is a constitutional unit having a different structure from the constitutional unit represented by formula (4);

in formula (10), $R^{12}$ represents an unsubstituted or substituted alkyl group, an unsubstituted or substituted aryl group or an unsubstituted or substituted monovalent heterocyclic group; X represents a single bond, —O—, —S— or —C($R^c$)$_2$—; $R^c$ represents an unsubstituted or substituted alkyl group or an unsubstituted or substituted aryl group; the two $R^c$ groups may be the same or different;

in formula (11), $R^{13}$ and $R^{13'}$ each independently represent a hydrogen atom, an unsubstituted or substituted alkyl group, an unsubstituted or substituted alkoxy group, an unsubstituted or substituted aryl group, an unsubstituted or substituted aryloxy group, an unsubstituted or substituted monovalent heterocyclic group, an unsubstituted or substituted silyl group, a halogen atom, an alkoxycarbonyl group, a carboxyl group or a cyano group.

4. The light-emitting device according to claim 1, wherein the constitutional unit represented by formula (7) is a constitutional unit represented by formula (14);

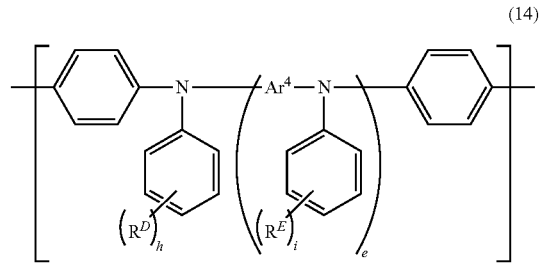

in formula (14), $Ar^4$ and e have the same meanings specified above; $R^D$ and $R^E$ each independently represent an unsubstituted or substituted alkyl group, an unsubstituted or substituted alkoxy group, an unsubstituted or substituted aryl group, an unsubstituted or substituted aryloxy group, an unsubstituted or substituted monovalent heterocyclic group, an unsubstituted or substituted silyl group, a halogen atom, an alkoxycarbonyl group, a carboxyl group or a cyano group; the letters h and i each independently represent an integer of 0 to 5; when multiple groups are present for $R^D$ and $R^E$, they may be the same or different.

5. The light-emitting device according to claim 1, wherein the polymer compound consists of the constitutional unit represented by formula (4), and at least one constitutional unit selected from the group consisting of constitutional units represented by formula (6) and constitutional units represented by formula (7).

6. The light-emitting device according to claim 1, wherein the light-emitting layer comprises a composition comprising the polymer compound and at least one material selected from the group consisting of hole transport materials, electron transport materials and light-emitting materials.

7. The light-emitting device according to claim 6, wherein the light-emitting material is a triplet emitting complex.

\* \* \* \* \*